(12) United States Patent
Boo et al.

(10) Patent No.: US 10,973,191 B1
(45) Date of Patent: Apr. 13, 2021

(54) *PLATYCODON* PLANT NAMED 'RAONJENA'

(71) Applicants: (AGRICULTURAL CORPORATION) AGROLEAD CO., LTD., Jeju-do (KR); Hag Hyun Kim, Cheongju-si (KR)

(72) Inventors: Hee-Ock Boo, Jeju-si (KR); Sung-Hyun Boo, Jeju-si (KR); Hag-Hyun Kim, Cheongju-si (KR); Sun-Hee Woo, Cheongju-si (KR); Soo-Jeong Kwon, Cheongju-si (KR)

(73) Assignees: (AGRICULTURAL CORPORATION) AGROLEAD CO., LTD., Jeju-si (KR); Hag Hyun Kim, Cheongju-si (KR)

( * ) Notice: Subject to any disclaimer, the term of this patent is extended or adjusted under 35 U.S.C. 154(b) by 0 days.

(21) Appl. No.: 16/702,089

(22) Filed: Dec. 3, 2019

(51) Int. Cl.
*A01H 6/26* (2018.01)
*A01H 5/02* (2018.01)

(52) U.S. Cl.
CPC ............... *A01H 6/26* (2018.05); *A01H 5/02* (2013.01)

(58) Field of Classification Search
CPC ........................................................ A01H 6/26
See application file for complete search history.

(56) References Cited

PUBLICATIONS

Ma et al American Journal of Plant Sciences vol. 6, pp. 2844-2849 (Year: 2015).*

* cited by examiner

*Primary Examiner* — David H Kruse
(74) *Attorney, Agent, or Firm* — Sughrue Mion, PLLC

(57) ABSTRACT

The present disclosure relates to a new and distinct cultivar of *Platycodon grandiflorum* named 'Raonjena' with green petals.

1 Claim, 3 Drawing Sheets
(3 of 3 Drawing Sheet(s) Filed in Color)

Specification includes a Sequence Listing.

PLATYCODON PLANT NAMED 'RAONJENA'

STATEMENT REGARDING SPONSORED RESEARCH OR DEVELOPMENT

This study was supported by Korea Institute of Planning and Evaluation for Technology in Food, Agriculture, Forestry (IPET) through Export Promotion Technology Development Program, funded by the Ministry of Agriculture, Food and Rural Affairs (MAFRA) (grant number 116121-03-2-HD030).

TECHNICAL FIELD

The present disclosure relates to a new and distinct cultivar of *Platycodon grandiflorum* named 'Raonjena'. The 'Raonjena' is a *Platycodon grandiflorum* with green flowers. *Platycodon grandiflorum* with green flowers due to mutation was found during superior species breeding tests of *Platycodon grandiflorum* with violet flowers, *Platycodon grandiflorum* with white flowers, and *Platycodon grandiflorum* with pink flowers. The 'Raonjena' is sterile, which means that the 'Raonjena' does not form seeds. Plant bodies of the *Platycodon grandiflorum* obtained by in vitro culture through vitro cutting (vegetative propagation) may be mass-propagated. The mass-propagated *Platycodon grandiflorum* may be ex vitro acclimatized to produce the 'Raonjena'.

BACKGROUND

*Platycodon grandiflorum* is an important traditional medicinal plant found in North East Asia (including China, Japan, and Korea.). The extract and some of the major components of *Platycodon grandiflorum*, such as platycodin D (PD) and platycodin D3, have been found to have diverse pharmacological activities, including anti-inflammatory activity (Ashok et al., 1999; Finkel et al., 2000), anti-allergy activity (Halliwell et al., 2006), the ability to augment immune responses (Halliwell et al., 2007), the ability to stimulate apoptosis in skin cells (Tiwari et al., 2001), anti-obesity and hyperlipidemia effects (Han et al., 2002; Zhao et al., 2008), and a protective effect against oxidative hepatotoxicity (Evans et al., 2001). In addition, the pharmacological properties of *Platycodon grandiflorum* are mainly due to the presence of saponins called platycodin that that may act individually, additively, or in synergy to improve human health (Choi et al., 2010). Plant cell or organ cultures are the attractive source to whole plant for the production of high-value secondary metabolites (Rao & Ravishankar, 2002).

SUMMARY

One stock of *Platycodon grandiflorum* mutation with green flowers was found during mating tests of *Platycodon grandiflorum* with violet flowers, *Platycodon grandiflorum* with white flowers, and *Platycodon grandiflorum* with pink flowers for superior species breeding at Woosong College (171, Dongdaejeon-ro, Dong-gu, Daejeon, Korea). The found *Platycodon grandiflorum* with green flowers was identified to be sterile. Thus, vitro cutting by tissue culture was carried out to obtain plantlets. The plantlets were maintained and propagated in vitro. The in vitro propagated plant bodies of the *Platycodon grandiflorum* with green flowers were acclimatized and then cultivated in an experimental field in Ogeunjang-dong, Sangdang-gu, Cheongju-si, Chungcheongbuk-do, Republic of Korea.

The *Platycodon grandiflorum* with green flowers improved through such process was named 'Raonjena', representative plantlet there of was deposited to and accepted by the Korean Collection for Type Cultures (KCTC) under the Budapest Treaty, and received a deposit number of KCTC14018BP on Nov. 11, 2019.

The 'Raonjena' is sterile. Further, the 'Raonjena' may be produced by mass-propagating plant bodies of the *Platycodon grandiflorum* obtained by in vitro culture through vitro cutting (vegetative propagation) and ex vitro acclimatizing the mass-propagated *Platycodon grandiflorum*.

First, a stem fragment of the 'Raonjena' was sterilized and washed using 70% alcohol and 1% NaOCl. Then, the plant body obtained by culturing the stem with nodes in ½ MS medium was used as a propagation material. The stem fragment of the 'Raonjena' was added to medium composition containing sucrose 5% (w/v); agar 0.6% (w/v); IBA (3-indole butyric acid) 0.0001% (w/v); and ¼ MS (Murashige & Skoog Medium) culture medium remaining quantity, and then pH of the addition was adjusted to 3.8 to 5.8. Then, the addition was cultured for 4 to 6 weeks by irradiating a LED light source for 12 to 24 hours at a temperature of 20 to 30° C.

The cultured 'Raonjena' plant body was washed using running water to remove the medium, then immersed in a disinfectant for several seconds, and then washed using water. Then, the 'Raonjena' plant body was transplanted into bed soil for horticulture, and then grown under conditions of 16 hours lighting and 70% humidity with light of 20 to 25° C. and 40 $\mu mol \cdot m^{-2} \cdot s^{1}$.

Gene analysis was performed to compare the 'Raonjena' with wild-type *Platycodon grandiflorum*. RNA de novo sequencing was performed by extracting total RNAs of the 'Raonjena' and the wild-type *Platycodon grandiflorum* (*Platycodon grandiflorum* with white flowers and *Platycodon grandiflorum* with violet flowers). Then, unigene assembly was performed using Trinity software. The assembled unigenes were annotated using seven databases (NR, NT, Swissprot, KOG, KEGG, GO, and InterPro).

27 specific unigenes were observed in the 'Raonjena' through Venn diagram analysis, which are shown in Table 1. In Gene Ontology analysis, transcription, DNA-templated (GO:0006351), transport (GO:0006810), photosynthesis, light reaction (GO:0019684), ATP synthesis coupled proton transport (GO:0015986), sterol biosynthetic process (GO:0016126), isopentenyl diphosphate biosynthetic process, mevalonate pathway (GO:0019287), mRNA processing (GO:0006397), translation (GO:0006412), reductive pentose-phosphate cycle (GO:0019253), photorespiration (GO:0009853) of the 'Raonjena' were activated more than the wild-type *Platycodon grandiflorum* (*Platycodon grandiflorum* with white flowers and *Platycodon grandiflorum* with violet flowers), and such analysis result is shown in Table 2.

TABLE 1

| gene ID | Nr | Nt |
| --- | --- | --- |
| CL3906.Contig4_All (SEQ ID NO. 1) | YP_009414761.1/5.4e−149/RNA polymerase alpha subunit (chloroplast) [*Platycodon grandiflorus*] >ARR27766.1 RNA polymerase alpha subunit (chloroplast) [*Platycodon grandiflorus*] | "KX352464.1/0.0/ *Platycodon grandiflorus* chloroplast, complete genome" |
| CL3906.Contig6_All (SEQ ID NO. 2) | YP_009414761.1/5.2e−149/RNA polymerase alpha subunit (chloroplast) [*Platycodon grandiflorus*] >ARR27766.1 RNA polymerase alpha subunit (chloroplast) [*Platycodon grandiflorus*] | "KX352464.1/0.0/ *Platycodon grandiflorus* chloroplast, complete genome" |
| CL3906.Contig5_All (SEQ ID NO. 3) | YP_009414761.1/5.3e−149/RNA polymerase alpha subunit (chloroplast) [*Platycodon grandiflorus*] >ARR27766.1 RNA polymerase alpha subunit (chloroplast) [*Platycodon grandiflorus*] | "KX352464.1/0.0/ *Platycodon grandiflorus* chloroplast, complete genome" |
| Unigene21208_All (SEQ ID NO. 4) | YP_009414747.1/1.4e−180/RNA polymerase beta"subunit (chloroplast) [*Platycodon grandiflorus*] >ARR27752.1 RNA polymerase beta"subunit (chloroplast) [*Platycodon grandiflorus*] | "KX352464.1/0.0/ *Platycodon grandiflorus* chloroplast, complete genome" |
| Unigene24626_All (SEQ ID NO. 5) | YP_009414743.1/9.1e−126/NADH dehydrogenase subunit K (chloroplast) [*Platycodon grandiflorus*] >ARR27748.1 NADH dehydrogenase subunit K (chloroplast) [*Platycodon grandiflorus*] | "KX352464.1/0.0/ *Platycodon grandiflorus* chloroplast, complete genome" |
| Unigene3183_All (SEQ ID NO. 6) | YP_009414752.1/1.0e−79/ATP synthase CF1 alpha subunit (chloroplast) [*Platycodon grandiflorus*] >ARR27757.1 ATP synthase CF1 alpha subunit (chloroplast) [*Platycodon grandiflorus*] | "KX352464.1/0.0/ *Platycodon grandiflorus* chloroplast, complete genome" |
| CL11954.Contig2_All (SEQ ID NO. 7) | AGZ15315.1/3.5e−215/mevalonate kinase [*Platycodon grandiflorus*] | "KC439364.1/0.0/ *Platycodon grandiflorus* mevalonate kinase (MK) mRNA, complete cds" |
| Unigene202_All (SEQ ID NO. 8) | "AFR67330.1/9.8e−118/flavonoid-3',5'-hydroxylase [*Platycodon grandiflorus*]" | "JQ403611.1/0.0/ *Platycodon grandiflorus* flavonoid-3',5'-hydroxylase mRNA, complete cds" |
| Unigene12268_All (SEQ ID NO. 9) | ARR27546.1/2.8e−214/maturase (mitochondrion) [*Platycodon grandiflorus*] | "KX063855.1/0.0/ *Diplostephium hartwegii* voucher TEX:Vargas 456 mitochondrion, complete genome" |
| Unigene15281_All (SEQ ID NO. 10) | ARR27546.1/3.9e−152/maturase (mitochondrion) [*Platycodon grandiflorus*] | "KX063855.1/0.0/ *Diplostephium hartwegii* voucher TEX:Vargas 456 mitochondrion, complete genome" |
| CL7827.Contigl_All (SEQ ID NO. 11) | ARR27572.1/protein S3 (mitochondrion) [*Platycodon grandiflorus*] | "KX063855.1/0.0/ *Diplostephium hartwegii* voucher TEX:Vargas 456 mitochondrion, complete genome" |
| CL2802.Contig3_All (SEQ ID NO. 12) | YP_009414724.1/1.5e−67/ ribosomal protein S18 (chloroplast) [*Platycodon grandiflorus*] >ARR27729.1 ribosomal protein S18 (chloroplast) *Platycodon grandiflorus*] | "KX352464.1/0.0/ *Platycodon grandiflorus* chloroplast, complete genome" |

TABLE 1-continued

| gene ID | Nr | Nt |
|---|---|---|
| CL10003.Contig2_All (SEQ ID NO. 13) | YP_009414775.1/0.0e+00/hypothetical chloroplast RF1 (chloroplast) [*Platycodon grandiflorus*] >YP_009414792.1 hypothetical chloroplast RF1 (chloroplast) [*Platycodon grandiflorus*] >ARR27780.1 hypothetical chloroplast RF1 (chloroplast) [*Platycodon grandiflorus*] >ARR2778 | "KX352464.1/0.0/ *Platycodon grandiflorus* chloroplast, complete genome" |
| Unigene25048_All (SEQ ID NO. 14) | "YP_009414741.1/8.3e−288/ ribulose-1,5-bisphosphate carboxylase/oxygenase large subunit (chloroplast) [*Platycodon grandiflorus*] >ARR27746.1 ribulose-1,5-bisphosphate carboxylase/oxygenase large subunit (chloroplast) [*Platycodon grandiflorus*]" | "KX352464.1/0.0/ *Platycodon grandiflorus* chloroplast, complete genome" |
| Unigene1329_All (SEQ ID NO. 15) | ARR27564.1/1.9e−48/NADH dehydrogenase subunit 4 (mitochondrion) [*Platycodon grandiflorus*] | "AK328194.1/0.0/*Solanum lycopersicum* cDNA, clone: LEFL2049D10, HTC in fruit" |
| Unigene17427_All (SEQ ID NO. 16) | YP_009414771.1/4.9e−191/ hypothetical chloroplast RF2 (chloroplast) [*Platycodon grandiflorus*] >YP_009414796.1 hypothetical chloroplast RF2 (chloroplast) [*Platycodon grandiflorus*] >ARR27774.1 hypothetical chloroplast RF2 (chloroplast) [*Platycodon grandiflor* | "KX352464.1/0.0/*Platycodon grandiflorus* chloroplast, complete genome" |
| CL10003.Contig1_All (SEQ ID NO.17) | YP_009414775.1/0.0e+00/hypothetical chloroplast RF1 (chloroplast) [*Platycodon grandiflorus*] >YP_009414792.1 hypothetical chloroplast RF1 (chloroplast) [*Platycodon grandiflorus*] >ARR27780.1 hypothetical chloroplast RF1 (chloroplast) [*Platycodon grandiflorus*] >ARR2778 | "KX352464.1/0.0/*Platycodon grandiflorus* chloroplast, complete genome" |
| Unigene90772_All (SEQ ID NO. 18) | YP_009414771.1/9.5e−262/ hypothetical chloroplast RF2 (chloroplast) [*Platycodon grandiflorus*] >YP_009414796.1 hypothetical chloroplast RF2 (chloroplast) [*Platycodon grandiflorus*] >ARR27774.1 hypothetical chloroplast RF2 (chloroplast) [*Platycodon grandiflor* | "KX352464.1/0.0/*Platycodon grandiflorus* chloroplast, complete genome" |
| Unigene201_All (SEQ ID NO. 19) | "AFR67330.1/1.4e−309/flavonoid-3',5'-hydroxylase [*Platycodon grandiflorus*]" | "JQ403611.1/0.0/*Platycodon grandiflorus* flavonoid-3',5'-hydroxylase mRNA, complete cds" |
| CL2802.Contig2_All (SEQ ID NO. 20) | YP_009414724.1/1.0e−67/ ribosomal protein S18 (chloroplast) [*Platycodon grandiflorus*] >ARR27729.1 ribosomal protein S18 (chloroplast) *Platycodon grandiflorus*] | "KX352464.1/0.0/*Platycodon grandiflorus* chloroplast, complete genome" |
| Unigene11152_All (SEQ ID NO. 21) | YP_009414771.1/1.7e−61/ hypothetical chloroplast RF2 (chloroplast) [*Platycodon grandiflorus*] >YP_009414796.1 hypothetical chloroplast RF2 (chloroplast) [*Platycodon grandiflorus*] >ARR27774.1 hypothetical chloroplast RF2 (chloroplast) [*Platycodon grandifloru* | "KX352464.1/0.0/*Platycodon grandiflorus* chloroplast, complete genome" |
| CL10780.Contig2_All (SEQ ID NO. 22) | YP_009414711.1/1.6e−247/ maturase K (chloroplast) [*Platycodon grandiflorus*] >ARR27719.1 maturase K (chloroplast) [*Platycodon grandiflorus*] | "KX352464.1/0.0/*Platycodon grandiflorus* chloroplast, complete genome" |

TABLE 1-continued

| gene ID | Nr | Nt |
|---|---|---|
| Unigene51089_All (SEQ ID NO. 23) | YP_009414782.1/5.9e−29/ribosomal protein L32 (chloroplast) [*Platycodon grandiflorus*] >ARR27779.1 ribosomal protein L32 (chloroplast) *Platycodon grandiflorus* | "KX352464.1/0.0/*Platycodon grandiflorus* chloroplast, complete genome" |
| CL1361.Contig13_All (SEQ ID NO. 24) | BAX04010.1/2.4e−196/cytochrome P450 72A554 [*Platycodon grandiflorus*] | "LC209202.1/0.0/*Platycodon grandiflorus* CYP72A554 mRNA for cytochrome P450 72A554, complete cds" |
| CL12047.Contig3_All (SEQ ID NO. 25) | "ACC54453.1/8.6e−274/ATP synthase beta subunit, partial (chloroplast) [*Platycodon grandiflorus*]" | "KX352464.1/0.0/*Platycodon grandiflorus* chloroplast, complete genome" |
| CL1361.Contig15_All (SEQ ID NO. 26) | BAX04010.1/3.8e−140/cytochrome P450 72A554 [*Platycodon grandiflorus*] | "LC209202.1/0.0/*Platycodon grandiflorus* CYP72A554 mRNA for cytochrome P450 72A554, complete cds" |
| CL2976.Contig3_All (SEQ ID NO. 27) | AML77394.1/1.6e−227/putative LOV domain-containing protein [*Platycodon grandiflorus*] | "KU699442.1/0.0/*Platycodon grandiflorus* isolate IHPC 2012886 putative LOV domain-containing protein mRNA, complete cds" |

TABLE 2

| gene ID | Gene Ontology |
|---|---|
| CL3906.Contig4_All | biological_process:GO:0006351//transcription, DNA-templated; cellular_component: GO:0009507//chloroplast; molecular_function: GO:0003899//DNA-directed 5'-3' RNA polymerase activity; GO:0003677//DNA binding; GO:0046983//protein dimerization activity; |
| CL3906.Contig6_All | biological_process: GO:0006351//transcription, DNA-templated; cellular_component: GO:0009507//chloroplast; molecular_function: GO:0003899//DNA-directed 5'-3' RNA polymerase activity; GO:0003677//DNA binding; GO:0046983//protein dimerization activity; |
| CL3906.Contig5_All | biological_process: GO:0006351//transcription, DNA-templated; cellular_component: GO:0009507//c hloroplast; molecular_function: GO:0003899//DNA-directed 5'-3' RNA polymerase activity; GO:0003677//DNA binding; GO:0046983//protein dimerization activity; |
| Unigene21208_All | biological_process:GO:0006351//transcription, DNA-templated; cellular_component:GO:0009536//plastid;GO:0009507//chloroplast; molecular_function:GO:0003899//DNA-directed 5'-3 RNA polymerase activity;GO:0003677//DNA binding; |
| Unigene24626_All | biological_process:GO:0006810//transport;GO:0019684//photosynthesis, light reaction; cellular_component:GO:0009535//chloroplast thylakoid membrane;GO:0016021//integral component of membrane; molecular_function:GO:0005506//iron ion binding;GO:0051539//4 iron, 4 sulfur cluster binding;GO:0048038//quinone binding;GO:0008137//NADH dehydrogenase (ubiquinone) activity; |
| Unigene3183_All | biological_process:GO:0015986//ATP synthesis coupled proton transport; cellular_component:GO:0045261//proton-transporting ATP synthase complex, catalytic core F(1);GO:0009536//plastid;GO:0005886//plasma membrane;molecular_function:GO:0005524//ATP binding;GO:0046933//proton-transporting ATP synthase activity, rotational mechanism; |
| CL11954.Contig2_All | biological_process:GO:0016126//sterol biosynthetic process;GO:0019287//isopentenyl diphosphate biosynthetic process, mevalonate pathway; cellular_component:GO:0005737//cytoplasm; molecular_function:GO:0005524//ATP binding;GO:0004496//mevalonate kinase activity; |
| Unigene202_All | cellular_component:GO:0016021//integral component of membrane; molecular_function:GO:0016705//oxidoreductase activity, acting on paired donors, with incorporation or reduction of molecular oxygen;GO:0020037//heme binding;GO:0005506//iron ion binding;GO:0004497//monooxygenase activity; |

TABLE 2-continued

| gene ID | Gene Ontology |
|---|---|
| Unigene12268_All | biological_process:GO:0006397//mRNA processing; cellular_component:GO:0005739//mitochondrion; |
| Unigene15281_All | biological_process:GO:0006397//mRNA processing; cellular_component:GO:0005739//mitochondrion; |
| CL7827.Contig1_All | biological_process:GO:0006412//translation; cellular_component:GO:0005840//ribosome;GO:0005739//mitochondrion; molecular_function:GO:0003723//RNA binding;GO:0003735//structural constituent of ribosome; |
| CL2802.Contig3_All | biological_process:GO:0006412//translation; cellular_component:GO:0005840//ribosome;GO:0009536//plastid;molecular function:GO:0003735//structural constituent of ribosome; |
| CL10003.Contig2_All | biological_process:GO:0006810//transport; cellular_component:GO:0016021//integral component of membrane;GO:0009536//plastid;GO:0005886//plasma membrane; molecular_function:GO:0050136//NADH dehydrogenase (quinone) activity;GO:0048038//quinone binding;GO:0051287//NAD binding; |
| Unigene25048_All | biological_process:GO:0019253//reductive pentose-phosphate cycle;GO:0009853//photorespiration; cellular_component: GO:0009507//chloroplast; molecular_function: GO:0000287//magnesium ion binding;GO:0004497//monooxygenase activity;GO:0016984//ribulose-bisphosphate carboxylase activity; |
| Unigene1329_All | biological_process:GO:0042773//ATP synthesis coupled electron transport; cellular_component:GO:0016021//integral component of membrane;GO:0005739//mitochondrion;molecular_function:GO:000813711N ADH dehydrogenase (ubiquinone) activity; |
| Unigene17427_All | cellular_component:GO:0009570//chloroplast stroma; molecular_function:GO:0005524//ATP binding; |
| CL10003.Contig1_All | cellular_component:GO:0016021//integral component of membrane;GO:0009536//plastid; |
| Unigene90772_All | cellular_component: GO:0016021//integral component of membrane ;GO:0009570l/chloroplast stroma; molecular_function: GO:0005524//ATP binding; |
| Unigene201_All | NA |
| CL2802.Contig2_All | NA |
| Unigene11152_All | NA |
| CL10780.Contig2_All | NA |
| Unigene51089_All | NA |
| CL1361.Contig13_All | NA |
| CL12047.Contig3_All | NA |
| CL1361.Contig15_All | NA |
| CL2976.Contig3_All | NA |

NA: Not detected

The 'Raonjena' contains pharmacological components such as saponin, platicodine, and the like. The pharmacological components contained are compared with the wild-type *Platycodon grandiflorum*, and the comparison result is shown in Table 3.

TABLE 3

|  | *Platycodon grandiflorum* with violet flower | 'Raonjena' |
|---|---|---|
| Deapioplatycodin D | 0.8 mg/g | 1.1 mg/g |
| Deapioplatycodin D3 | 0.5 mg/g | 0.8 mg/g |
| Platycoside B | 1.72 mg/g | 1.9 mg/g |

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying color photographs depict characteristics of the new 'Raonjena' plants as nearly true as possible to make color reproductions. The overall appearance of the 'Raonjena' plants in the photographs is shown in colors that may differ slightly from the color values described in the detailed botanical description.

DETAILED DESCRIPTION

Figure 1:
FIG. 1 shows 'Raonjena', which is cultivated by mass-propagating and ex vitro acclimatizing *Platycodon grandiflorum*.
Figure 2:
FIG. 2 shows 'Raonjena' with bloomed flower.
Figure 3:
FIG. 3 shows green flowers of 'Raonjena' grown outdoors.
Figure 4:
FIG. 4 shows green flowers of 'Raonjena' grown indoors.
Figure 5:
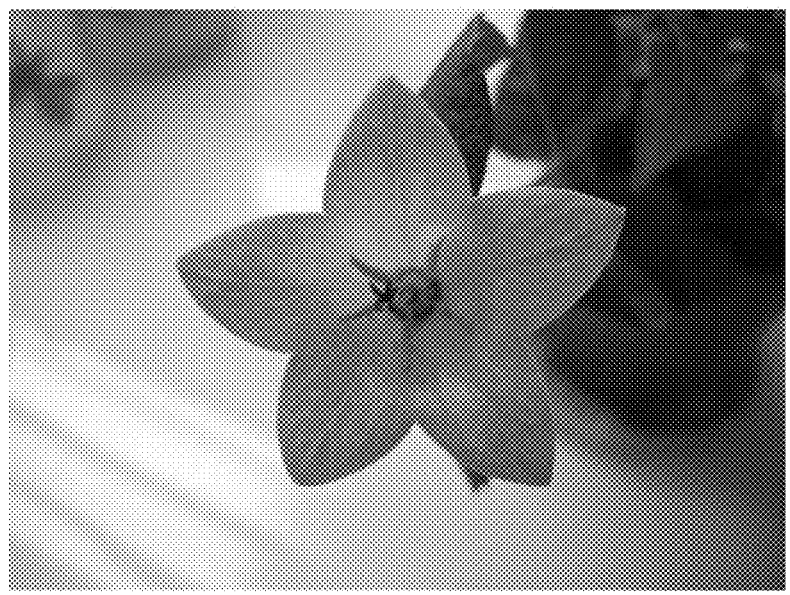
FIG. 5 is a front view of green flowers of 'Raonjena' grown indoors.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The following is a detailed description of the new cultivar of 'Raonjena'.

The plant:

Type (life form and habit).—Perennial root herb.

Classification.—Denomination.—Raonjena

Species.—*Platycodon grandiflorum*.

Origin, form, and growth characteristics:

Origin.—Mutation that occurred during the mating of the *Platycodon grandiflorum* with violet flowers, the *Platycodon grandiflorum* with white flowers, and the *Platycodon grandiflorum* with pink flowers.

Propagation.—The Raonjena is sterile, and cultivated by ex vitro acclimatizing the *Platycodon grandiflorum*, which is obtained by in vitro mass-propagating the plant body, which is in vitro cultured through the vitro cutting (vegerative propagation).

Mature habit.—The Raonjena is the perennial root herb, which grows about 30 to 80 cm tall. Roots thereof are thick, and stems thereof grow straight. When the Raonjena is cut, white juice comes out. The stems are mostly green. Further, middle and lower portions of the node and the stem may be colored purple.

Foliage: Leaves.

Arrangement.—Alternate.

Form.—Single, oval, or long egg-shaped leaf

Leaf (without petiole).—4-7 cm long; 1.5-2.5 cm wide.

Margins.—Serrated leaf (leaf margins have serrations and pointed ends—Serrated margins, tapering to an acuminate apex).

Color.—Upper side—Green, Pantone 356

Color.—Under side—Light green, Pantone 363

Texture.—Smooth, glabrous.

Other leaves characteristics.—Lower leaves are opposite, but upper leaves are alternated or three leaves are verticillated.

Stem: The stem is upright, has no hair, has a diameter of 3 to 4 mm. White latex comes out when the stem is cut. The number of side branches of the stem is 10 to 13.

Color.—Green, Pantone 370

Height.—30-80 cm.

Flowers: Flowers bloom in July to August and bloom for 4 to 6 weeks. The flowers bloom upwards and have a bell shape in which ends thereof spread. The flower has a diameter of 4 to 5 cm, and the end thereof is split into 5 pieces. A calyx is split into 5 pieces, and a lobe is 0.5 to 5 mm long and is triangular lanceolate. A corolla has a bell shape in which ends thereof spread. The corolla has a diameter of 4 to 5 cm. The end of the corolla is split into 5 pieces, and the split end is triangular. The number of stamens is 5, and the number of pistils is 1. An ovary has five loculi, and a stigma is split into five pieces. A filament is 0.6 to 0.8 cm, inflorescence is a raceme, and the flower is hermaphrodite flower.

Petals: A petal blooms upwards and has a bell shape in which ends thereof spread. The petal has a diameter of 4 to 5 cm. Further, the end of the petal is split into 5 pieces. A color of the petal is light green (Pantone 360) or green (Pantone 361).

Sepals: A sepal is split into 5 pieces. The lobe is 0.5 to 5 mm long and is triangular lanceolate.

Roots: A root is columnar and thick. Further, white latex comes out when the stem is cut. The root is a succulent tuberous root with light brown color (Pantone 1365).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A new and distinct cultivar of *Platycodon* plant named 'Raonjena', as shown and described, representative plantlet thereof was deposited under accession number KCTC 14018BP.

* * * * *

SEQUENCE LISTING

```
<160> NUMBER OF SEQ ID NOS: 28

<210> SEQ ID NO 1
<211> LENGTH: 3275
<212> TYPE: DNA
<213> ORGANISM: Artificial Sequence
<220> FEATURE:
<223> OTHER INFORMATION: CL3906.Contig4_All

<400> SEQUENCE: 1
ttaataaaag gctattctct ttgactgaat aatagtccac aacacaagtg aaagttgaag      60
ttcatattga ataacctaaa aaaccaaatt ttctattcca cacaccagta aatacatagt     120
tctgacaaga attcaatcaa agtatgtcta gttccacaat acaatgaaat atctgatata     180
tatctcctcc ttacatagtt ttttcttact cttttctttt ttcttcccaa tatatatttg     240
gtaatcaatt ttcatcgtgt agtacttgca ttaatcccga atattcagtt gaagactttc     300
gatgtcatta ctggccaacc agtttttga tggaactcca gacagaagag ggccgtgtac     360
cagggtcttc ttttcttgat gaaatacgtg aaaaatcatt agaatttcgt gaatgagacg     420
aagattccat tatattcggc tgcttggatg acgatgatgc tccgtcctct aagtaaggca     480
ctatatattg tttcatttcg cttttagaaa cgtccatatg acctcctggt acgcttatga     540 atttcaccttt tccggcttcg tccagtgttt tcaaaccaat ccaatcttct gtgtagagct     600
tcgtctcttg cgcaggcagc acgggatccc aagcccatc gggataatac ccaaaccaag     660
aggtttcttt cggaaccaac acagcatctt tctcacactt atgaagaata tcaagaaaaa     720
```

```
agagtgcatc accaatttaa aattgtatcc gttgggttga aagaaactag aagaattctt    780
cttaccatta taagcaccag attttgcaag ctagaaaacc gttgtttgta agtggagttt    840
ttagtgaatt cgttattgat ctttggcaga aacttgcatc ctttctcata gtcatcaaga    900
gcctcagtta agtactgtac tcactgttgg aattctaatg taatcagctg gccccaagtg    960
ttcctgcacg tagccgctgt aaattgctaa cttcatgata cagtccacca taacgcacaa   1020
gaaaccagaa ccacaaaatg gtacagcagc tatcccggca tgaggacctg atactgatat   1080
gaaattcttc acaggaggtc ctccatcaca gagctcaacc accctcggc caaccaagtt    1140
tccctgggaa agtccaagta tgttataacc ctcgcggagt tcactcattt tcttcacctt   1200
ctcacaggca atctgtgtct gttccgaaaa gggcataaac cacgaatccc acccccatc    1260
tccaatttct atgcagtatc cttgagaatt ggaccatttg cttaaacttt cagtgaaatg   1320
ttttactcct ctatgggtac atttatctgc aacgccatgg aagacaacaa acggtaaggc   1380
atgagtgacg attggcaaca gagtcaaagt agaagtgatc aggattatga acaaggctgg   1440
aattgatgac tttgaagcca tttgactgtg gagaatcaaa caagtttcga caatcagagc   1500
aatggggaaa agttgcaata tggttgggag tctgattcct gcagttttgg gatgttccag   1560
gaagcttttt ggtactttaa tggaggactc accggagttc ttttgagata cacccttgaa   1620
tttggaaatc acaaacccca aaattgctcc cacttgcgca atggcgaaat tcccccttt    1680
tctttgctcg gttgagtttg tgaaatggaa taagagggag tattatggaa ggtgttgtat   1740
ttggggagag atagagtggt gagatttgga tgagagagag atagcagcag cttggaagat   1800
gaacttggaa gaggcgctag ggcgagcacc ggctattttt ttttttgtttt tttgttattt   1860
tgacaaatgg atcaggaagg gtagaggggc gtagaggaac catatgttga ttgtcctcta   1920
aatggaagtt ttcttcttct gtatataaaa agggaataaa caaatcaatc aaattctgag   1980
tggcttcacg aagtgcttct tgggagtcaa aacttccatt tgtccagatt tcaagaaaga   2040
gtatctcttg tttcttattt ccagtcccat aagaatgaat actatgattc acatttcgaa   2100
caggcattaa tacatcccct ataggataac ttccatctat aatcctcttt tctgttgtac   2160
gatatccaca tccatgactc ctttcgattt gtaaaaaaat acacaagtca attggttctg   2220
tcaaggtagc tatatgctgt gtattatcaa tgattttgag aaaatgcggc gcgatgatat   2280
cttgagcggt tacatatccg gggcccttag cacaaacggc tgcctcacaa gttccatata   2340
gatgacttct cactacaatt tcttgcaaat tcaataaaat ttcatgtact gattcttgaa   2400
taccaactat ggtagaatat tcgtgtggta ttttctcaaa ttttgcgcgt gtgatacatg   2460
tcccttctat ttctccaagt aaagctcgtc gcatcgcaat gcctattgtg tccgcttgac   2520
cttttcataag tggagacaga ataaagcgtc cataataaag acgtttactg tctgctcttg   2580
attccaaaca cttccacagt gtccgagtag atactcttac ttttctcga accataataa    2640
tatgatttaa tcagatcttt aaatcgttta tttctcttgt ttctcttgct cttgaaattt   2700
cttccatttt gatttctaca cgcgtctttt gttcggaggt ctacagccat tatgtggcaa   2760
aggagttaca tcccttacaa aagttaatcg tagaccctt tgtaattttt tgtaaataac    2820
tcgtaatgct gcgtctcttc cgagaccgac accttttatc agcactagtg ctcgtttcat   2880
caatactata cgcatagcgt ctcgtgctac ggtttcagca gcaaatggcg accctttcg    2940
tttactccgg aagccgcaaa taccggccga ggacgaagaa atcactcgac cctctacatc   3000
tgtaacagtc acaatggtat tattaaaact tgcttgaaca tgaataaccc ctttgcgtat   3060
```

-continued

```
tctacgtggc ttcttacgtg cacgcttacg ttgaatatat gcacgaaatc cctttagagc    3120
ttttgccata ttttatcatc tcataaatat gagtcagaga tatatggata tatccatttc    3180
atgtcaaaaa agatcccctc ttttatttga atattgggcc ctttcccgag tctgattatc    3240
cttgtctttg tttatgtctt gggttggaac aaatt                               3275

<210> SEQ ID NO 2
<211> LENGTH: 3187
<212> TYPE: DNA
<213> ORGANISM: Artificial Sequence
<220> FEATURE:
<223> OTHER INFORMATION: CL3906.Contig6_All

<400> SEQUENCE: 2
ttaataaaag gctattctct ttgactgaat aatagtccac aacacaagtg aaagttgaag      60
ttcatattga ataacctaaa aaaccaaatt ttctattcca cacaccagta aatacatagt     120
tctgacaaga attcaatcaa agtatgtcta gttccacaat acaatgaaat atctgatata     180
tatctcctcc ttacatagtt tttcttact cttttctttt ttcttcccaa tatatatttg      240
gtaatcaatt ttcatcgtgt agtacttgca ttaatcccga atattcagtt gaagactttc     300
gatgtcatta ctggccaacc agttttttga tggaactcca gacagaagag ggccgtgtac     360
cagggtcttc ttttcttgat gaaatacgtg aaaaatcatt agaatttcgt gaatgagacg     420
aagattccat tatattcggc tgcttggatg acgatgatgc ccgtcctct aagtaaggca      480 ctatatattg tttcatttcg cttttagaaa cgtccatatg acctcctggt acgcttatga     540
atttcacctt tccggcttcg tccagtgttt tcaaaccaat ccaatcttct gtgtagagct     600
tcgtctcttg cgcaggcagc acgggatccc aagccccatc gggataatac ccaaaccaag     660
aggtttcttt cggaaccaac acagcatctt tctcacacat tataagcacc agattttgca     720
agctagaaaa ccgttgtttg taagtggagt tttagtgaa ttcgttattg atctttggca      780
gaaacttgca tcctttctca tagtcatcaa gagcctcagt taagtactgt actcactgtt     840
ggaattctaa tgtaatcagc tggccccaag tgttcctgca cgtagccgct gtaaattgct     900
aacttcatga tacagtccac cataacgcac aagaaaccag aaccacaaaa tggtacagca     960
gctatcccgg catgaggacc tgatactgat atgaaattct tcacaggagg tcctccatca    1020
cagagctcaa ccaccccctcg gccaaccaag tttccctggg aaagtccaag tatgttataa   1080
ccctcgcgga gttcactcat tttcttcacc ttctcacagg caatctgtgt ctgttccgaa    1140
aagggcataa accacgaatc ccacacccca tctccaattt ctatgcagta tccttgagaa    1200
ttggaccatt tgcttaaact ttcagtgaaa tgttttactc ctctatgggt acatttatct    1260
gcaacgccat ggaagacaac aaacggtaag gcatgagtga cgattggcaa cagagtcaaa   1320
gtagaagtga tcaggattat gaacaaggct ggaattgatg actttgaagc catttgactg   1380
tggagaatca aacaagtttc gacaatcaga gcaatgggga aaagttgcaa tatggttggg   1440
agtctgattc ctgcagtttt gggatgttcc aggaagcttt ttggtacttt aatggaggac   1500
tcaccggagt tcttttgaga taacaccttg aatttggaaa tcacaaaccc caaaattgct   1560
cccacttgcg caatggcgaa attccccccct tttcttgct cggttgagtt tgtgaaatgg    1620
aataagaggg agtattatgg aaggtgttgt atttggggag atagagtg gtgagatttg      1680 gatgagagag agatagcagc agcttggaag atgaacttgg aagaggcgct agggcgagca   1740
ccggctattt ttttttttgtt ttttgttat tttgacaaat ggatcaggaa gggtagaggg   1800
gcgtagagga accatatgtt gattgtcctc taaatggaag ttttcttctt ctgtatataa   1860
```

```
aaagggaata acaaatcaa tcaaattctg agtggcttca cgaagtgctt ctttgggagt    1920
caaacttcca tttgtccaga tttcaagaaa gagtatctct tgtttcttat ttccagtccc    1980
ataagaatga atactatgat tcacatttcg aacaggcatt aatacatccc ctataggata    2040
acttccatct ataatcctct tttctgttgt acgatatcca catccatgac tcctttcgat    2100
ttgtaaaaaa atacacaagt caattggttc tgtcaaggta gctatatgct gtgtattatc    2160
aatgattttg agaaaatgcg gcgcgatgat atcttgagcg gttacatatc cggggccctt    2220
agcacaaacg gctgcctcac aagttccata tagatgactt ctcactacaa tttcttgcaa    2280
attcaataaa atttcatgta ctgattcttg aataccaact atggtagaat attcgtgtgg    2340
tattttctca aattttgcgc gtgtgataca tgtcccttct atttctccaa gtaaagctcg    2400
tcgcatcgca atgcctattg tgtccgcttg acctttcata agtggagaca gaataaagcg    2460
tccataataa agacgtttac tgtctgctct tgattccaaa cacttccaca gtgtccgagt    2520
agatactctt acttttctc gaaccataat aatatgattt aatcagatct ttaaatcgtt    2580
tatttctctt gtttctcttg ctcttgaaat ttcttccatt ttgatttcta cacgcgtctt    2640
ttgttcggag gtctacagcc attatgtggc aaaggagtta catcccttac aaaagttaat    2700
cgtagaccct ttttgtaatt tttgtaaata actcgtaatg ctgcgtctct tccgagaccg    2760
acacctttta tcagcactag tgctcgtttc atcaatacta tacgcatagc gtctcgtgct    2820
acggtttcag cagcaaatgg cgacccttt cgtttactcc ggaagccgca ataccggcc    2880 gaggacgaag aaatcactcg accctctaca tctgtaacag tcacaatggt attattaaaa    2940
cttgcttgaa catgaataac cccttttgcgt attctacgtg gcttcttacg tgcacgctta    3000
cgttgaatat atgcacgaaa tcccttaga gcttttgcca tatttatca tctcataaat    3060 atgagtcaga gatatatgga tatatccatt tcatgtcaaa aaagatcccc tcttttattt    3120
gaatattggg ccctttcccg agtctgatta tccttgtctt tgtttatgtc ttgggttgga    3180
acaaatt                                                              3187

<210> SEQ ID NO 3
<211> LENGTH: 3253
<212> TYPE: DNA
<213> ORGANISM: Artificial Sequence
<220> FEATURE:
<223> OTHER INFORMATION: CL3906.Contig5_All

<400> SEQUENCE: 3
ttaataaaag gctattctct ttgactgaat aatagtccac aacacaagtg aaagttgaag      60
ttcatattga ataacctaaa aaaccaaatt ttctattcca cacaccagta aatacatagt     120
tctgacaaga attcaatcaa agtatgtcta gttccacaat acaatgaaat atctgatata     180
tatctcctcc ttacatagtt ttttcttact cttttctttt ttcttcccaa tatatatttg     240
gtaatcaatt ttcatcgtgt agtacttgca ttaatcccga atattcagtt gaagactttc     300
gatgtcatta ctggccaacc agttttttga tggaactcca gacagaagag ggccgtgtac     360
cagggtcttc ttttcttgat gaaatacgtg aaaaatcatt agaatttcgt gaatgagacg     420
aagattccat tatattcggc tgcttggatg acgatgatgc tccgtcctct aagtaaggca     480
ctatatattg tttcatttcg cttttagaaa cgtccatatg acctcctggt acgcttatga     540
atttcacctt tccggcttcg tccagtgttt tcaaaccaat ccaatcttct gtgtagagct     600
tcgtctcttg cgcaggcagc acgggatccc aagccccatc gggataatac ccaaaccaag     660
```

```
aggtttctttt cggaaccaac acagcatctt tctcacactt atgaagaata tcaagaaaaa    720
agagtgcatc accaatttaa aattgtatcc gttgggttga agaaactag aagaattctt      780 cttaccatta taagcaccag attttgcaag ctagaaaacc gttgtttgta agtggagttt    840
ttagtgaatt cgttattgat cttttggcaga aacttgcatc ctttctcata gtcatcaaga   900
gctgttggaa ttctaatgta atcagctggc cccaagtgtt cctgcacgta gccgctgtaa   960
attgctaact tcatgataca gtccaccata acgcacaaga aaccagaacc acaaaatggt   1020
acagcagcta tcccggcatg aggacctgat actgatatga aattcttcac aggaggtcct  1080
ccatcacaga gctcaaccac ccctcggcca accaagtttc cctgggaaag tccaagtatg  1140
ttataaccct cgcggagttc actcattttc ttcaccttct cacaggcaat ctgtgtctgt  1200
tccgaaaagg gcataaacca cgaatcccac accccatctc caatttctat gcagtatcct  1260
tgagaattgg accatttgct aaactttca gtgaaatgtt ttactcctct atgggtacat   1320
ttatctgcaa cgccatggaa gacaacaaac ggtaaggcat gagtgacgat tggcaacaga  1380
gtcaaagtag aagtgatcag gattatgaac aaggctggaa ttgatgactt tgaagccatt  1440
tgactgtgga gaatcaaaca gtttcgaca atcagagcaa tggggaaaag ttgcaatatg   1500
gttgggagtc tgattcctgc agttttggga tgttccagga agcttttggg tactttaatg  1560
gaggactcac cggagttctt ttgagataac accttgaatt tggaaatcac aaaccccaaa  1620
attgctccca cttgcgcaat ggcgaaattc ccccctttc tttgctcggt tgagtttgtg   1680
aaatggaata agagggagta ttatggaagg tgttgtatt ggggagagat agagtggtga    1740
gatttggatg agagagagat agcagcagct tggaagatga acttggaaga ggcgctaggg  1800
cgagcaccgg ctattttttt tttgttttt tgttatttg acaaatggat caggaagggt    1860
agaggggcgt agaggaacca tatgttgatt gtcctctaaa tggaagtttt cttcttctgt  1920
atataaaaag ggaataaaca aatcaatcaa attctgagtg gcttcacgaa gtgcttcttt  1980
gggagtcaaa cttccatttg tccagatttc aagaaagagt atctcttgtt tcttatttcc  2040
agtcccataa gaatgaatac tatgattcac atttcgaaca ggcattaata catcccctat  2100
aggataactt ccatctataa tcctctttc tgttgtacga tatccacatc catgactcct   2160
ttcgatttgt aaaaaaatac acaagtcaat tggttctgtc aaggtagcta tatgctgtgt  2220
attatcaatg attttgagaa aatgcggcgc gatgatatct tgagcggtta catatccggg  2280
gcccttagca caaacggctg cctcacaagt tccatataga tgacttctca ctacaatttc  2340
ttgcaaattc aataaaattt catgtactga ttcttgaata ccaactatgg tagaatattc  2400
gtgtggtatt ttctcaaatt ttgcgcgtgt gatacatgtc ccttctattt ctccaagtaa  2460
agctcgtcgc atcgcaatgc ctattgtgtc cgcttgacct ttcataagtg gagacagaat  2520
aaagcgtcca taataaagac gtttactgtc tgctcttgat tccaaacact tccacagtgt  2580
ccgagtagat actcttactt tttctcgaac cataataata tgatttaatc agatctttaa  2640
atcgtttatt tctcttgttt ctcttgctct tgaaatttct tccatttga tttctacacg    2700 cgtcttttgt tcggaggtct acagccatta tgtggcaaag gagttacatc ccttacaaaa  2760
gttaatcgta gacccttttt gtaattttg taaataactc gtaatgctgc gtctcttccg    2820
agaccgacac cttttatcag cactagtgct cgtttcatca atactatacg catagcgtct  2880
cgtgctacgg tttcagcagc aaatggcgac ccttttcgtt tactccggaa gccgcaaata  2940
ccggccgagg acgaagaaat cactcgaccc tctacatctg taacagtcac aatggtatta  3000
ttaaaacttg cttgaacatg aataacccct ttgcgtattc tacgtggctt cttacgtgca  3060
```

```
cgcttacgtt gaatatatgc acgaaatccc tttagagctt ttgccatatt ttatcatctc    3120
ataaatatga gtcagagata tatggatata tccatttcat gtcaaaaaag atcccctctt    3180
ttatttgaat attgggccct ttcccgagtc tgattatcct tgtctttgtt tatgtcttgg    3240
gttggaacaa att                                                      3253

<210> SEQ ID NO 4
<211> LENGTH: 1043
<212> TYPE: DNA
<213> ORGANISM: Artificial Sequence
<220> FEATURE:
<223> OTHER INFORMATION: Unigene21208_All

<400> SEQUENCE: 4
gaggaagtgc atatcttagc cggatcctct tctataatgg tacgaaacaa tagtattatt      60
ggagtagata cacaaatcac tttaaagaca agaagcagaa taggcgggtt ggtccaagtg     120
gaaagaaaaa aaaaagaat tgaacttaga attttttctg gagatatcca ttttcctgga     180
aagaaagata agctatccgg atatagtggc atcttgatac caccaagaag aggaaaaaaa     240
aattccaagg aatacaaaaa tttgaaaaat tggctctata tccaacagct cacacttcgc     300
aagaaaaagt attttgtttt ggttcgacct gtagtcacat atgaaaaaac gggtgatata     360
aatttagtaa gacttttccc tccggatcta ttccaggaac gggattatgt acaacttcaa     420
attgtcaatt atatctttta tggaaacggc aatccaattc ggggaatttc ggatacaagt     480
attcaattag ttcgaacttg tttagtattg aattgggacc aagacaacaa aagttcttct     540
agcaacgagg cttgtgcttc ctttgttgaa atacggacaa aggatttgat taaagatttt     600
tttaaaatag acttagcaaa atcgccatt tcatatacca gaaaaaggaa tgatctatcg     660
ggttcagggt tgatctctga gagtggagca gatcacacca atatcaatcc cttttctgcc     720
gtttattccg attccacggc aagtcttcaa gaatccctta ccaaaatcag gaactatc       780 catacgttgt tgaatcaaaa taaggaatgc caatccttga taattttgtc agcatccaat     840
tgtttttatt ctcgaatggg tctattcaac gatgtcaaat cttttggtat gaaaaaagaa     900
tcaattaaaa gggacccccc aattccaact aagaattcct tgggcccttt aggaacgtcc     960
caattaataa cactcatcag tttgatctaa acgaatgggc ttttttttctt ggtgaataac    1020 tacaaatgag caaaatgttt ccg                                           1043

<210> SEQ ID NO 5
<211> LENGTH: 2745
<212> TYPE: DNA
<213> ORGANISM: Artificial Sequence
<220> FEATURE:
<223> OTHER INFORMATION: Unigene24626_All

<400> SEQUENCE: 5
ctaaaataaa tatcccaca ccaatattca aaatcttgag atgaaaattt ctatccattc       60
tcttccatat gactccttac tctatggtaa atcactaaga aaaatagaca aaaagacctc     120
ccgagtagat tgtgaaatct atataataac aataataata agcaaacgaa aactatattt     180
aaatttcaat caatttctaa gaatttcaaa ttttctcttt atttgattat tataaattct     240
aaacaaaaaa tgagaatttt ctttagaatt cccttttttta gataaaatcc taggtgagac     300
tgagataaaa agaagaaaat ttggataaga gcaatagtta gttatactaa ctataacaac     360
aaatggaaat atatgtaatg aaataggat ttccgttgat gaatcttgaa acaagacatg      420
```

```
ccctagagta acaaagtaa actagacggt tcgagcaaaa tcaatccttg cttaaactaa      480
aaagttatgg atttcaaatg gaattggcga atccggtata ttttccacct tcataggagt    540
gcgtctatgc ttctgctttta cgaatatgat atttttttggg catttctaat aatatctagt   600
cttattccta ttttgacttt ttttctttcg ggagttttag cccccattaa caaaggacca    660
gagaaacttt ctagttatga atcgggtata gaaccaatag gcgacgcttg gttacaattt    720
agaattcgct attatatgtt tgctctagtt tttgttgttt ttgatgttga aacggttttt    780
ctttatccat gggcaatgag tttcgatgta ttgggtctat ctgtatttct agaagctttt    840
attttcgtgc ttatcttaat tgttggtttg ttttatgcat ggcgaaaggg ggcattggaa    900
tggtcttagc tcctgaatat tgagacaata aaaagaaaaa ggaaaagttg agacagttat    960
gaattccgtt gagtttccct tacttaatcg aacaagccaa aattccgtta tttcaactac   1020
actaaatgat ctttcaaatt ggtcaaggct ctctagtttta tggccgcttc tctacggtac  1080
cagttgttgc ttcatcgaat ttgcttcact aataggttca cgattcgact ttgatcgtta   1140
cggactagta ccgagatcga gtcctagaca agcagaccta atttaacag ccggaacagt    1200 aacaatgaaa atggcccctt ctttagtgag attatatgag caaatgcctg aaccaaaata   1260
tgttatagct atgggagcat gtacaattac cgggggtatg ttcagtaccg attcttatag   1320
tacggttcgg ggagtcgata agctaattcc tgtggatgtc tatttgccgg gctgtccacc   1380
taaaccagaa gccgttatag atgctataac aaaacttcgc aaaaaatat ctcaagaaat    1440 ctatgcagat agaattaggt cttcgcgcac gaatcggtgt tttactacca atcacaagtt   1500
gcgggttggg cggagtattc atactggaaa ttctgatcaa ggattccttt atcacctacc   1560
atctacttca gagataccct cggaaacatt tttaaaatac aaaagtaaaa gttccgtctc   1620
ttcccacgga ttagtgaatt agacagaatt cttctgtaca gaataaaaga gaagaaaaag  1680
tcatggccca atcttcagaa atttcatcgt aaatgtggga aatacttatc aaaaaatgcg   1740
ggagagagaa aaaagatgca gggttatttg tctacttggc tagttaagca tgggctaatt   1800
catagatctt tgggttttga ttaccaagga atagagactt tcaaatcaa atccgaggat    1860 tggcattccc ttgctgtcat tttatatgta tatggttaca attatctacg cttccaatgc   1920
gcctatgatg tagcaccagg cggactgtta gctagtgtgt atcatcttac gagactaaag   1980 tatgcgtag atcaaccaga agaggtatgc ataaaagtat ttgcccccag gagggatcct   2040
acaattccgt ctgttttctg ggtttggaaa agtgtggatt tcaagaacg ggaatcttat    2100 gatatgttag gaattttttta tgagaatcat ccccggttga aacgtatttt aatgccagaa   2160
agttggatag gatggccttt gcgtaaggat tatattgccc ccaattttta tgaaatacaa   2220
gatgctcatt aactgataaa aaactaatct tcatttctac aattctctag attcaaggct   2280
ctgttctaga ttaaacatag gaattgaggt ctcatttgaa ttatgagata ggataagaaa   2340
aaagacaata caattaggga tttattggta ttctcaaatt tgcaagatac ttttttcgga   2400
tgatccaagc caataggatg aaccaaacga gttctgcatc gtgaactttg tattgcgcac  2460
atcacttaga cgggctctag taaagtcatg gaaggaagga atgtagaagg aaatgcaaaa   2520
atagaatcgg aaaatacaa aggaatgaaa ggctatcgaa ttcaatttat ttctgtcgat    2580
atctgaactg aatcttgtct attcgtatcc ttcaactcct ttagactttt gagtctttca   2640
accaacgaat ataacccttc gaataagtat taagattctt tttgaagtag aggataaatg   2700
aaataaaaaa gactagaaaa tagaatctaa taaattagat tcttt                    2745
```

<210> SEQ ID NO 6
<211> LENGTH: 4740
<212> TYPE: DNA
<213> ORGANISM: Artificial Sequence
<220> FEATURE:
<223> OTHER INFORMATION: Unigene3183_All

<400> SEQUENCE: 6

| | | | | | |
|---|---|---|---|---|---|
| atggtcacct | cacagactct | gaggtttgtg | cctgttgata | caaaagtttt | ttcctggaga | 60 |
| aattagggga | aggagtccta | cttcccattt | ttgtgtccca | aaaataaagc | cctgttttta | 120 |
| aattaaagct | ataacatgat | gtttattgtt | gctcctactg | ttgtactcct | cgtcccaaaa | 180 |
| gaaatacacc | ttccacttta | ggtagtccaa | aaagaaagg | tacattccct | ttccaggaaa | 240 |
| gctcttttta | gcaatttgac | ttttttgaaa | ataaattac | atgggcccac | cattgaaaat | 300 |
| tttacctatg | atataactgg | agtggggtcc | actatattga | tgggtacttt | gggaagtcaa | 360 |
| aggattggca | agaaatttct | taacttctgc | aacaagtcat | aatataccct | ttttctgct | 420 |
| gcggagggtt | tatttagtgc | aatttaaagg | aaatatagaa | agcaaaagt | acaatagtaa | 480 |
| aaagtttgac | ttttttaaaca | cgactctttt | ttggggagat | ggggcatttg | ataacaatgc | 540 |
| tttctcaatt | gtattgacct | attcttttcc | actttaaaaa | aaatttgtac | agcacggatt | 600 |
| cccttttcatt | ttcttttcct | ttactatcaa | accccaggaa | ccagctatgc | aataaattta | 660 |
| gttttgagca | agacaagttc | aatggaggaa | aaagatattc | tgataccgaa | ctcactaatt | 720 |
| aactgtttat | aaaaggtctc | aattaagcgt | gcggctagga | cttggtgaca | tgtggtcact | 780 |
| tggtatagtt | agtaaagtgc | atgagcaacg | attataacgg | acaaatatttt | ttatctgccg | 840 |
| atctattcaa | tgctggaatc | cgacctgcta | ttaatgtggg | tctctcggtt | tctcgggtcg | 900 |
| ggtctgcagc | tcaaattaaa | gctatgaaac | aagtagttgg | ccaattaaaa | ttggacttgg | 960 |
| cgcaattgac | agaattagaa | acttttgcac | aatttgcttc | cgatctcgat | aaaggtactc | 1020 |
| agaatcaatt | ggcaagaggt | cgacgattac | gcgaattgct | taaacaatct | caatctaaac | 1080 |
| ctctcgcggt | ggaagaacag | ataatgacta | tttatacggg | aacaaacggt | tatctcgatt | 1140 |
| cattagaaat | tagccaggta | atgaatttc | ttgataaatt | acggaaatat | ttaaaagaaa | 1200 |
| agaaaccgca | gtttcaagaa | atcatatctt | ctaccaagat | cttcaccgag | gaagcagaag | 1260 |
| acatttttaaa | aaaagctatt | caaaaacaga | tggggcttta | gtaacacgca | gcataaaaaa | 1320 |
| ttgctcactc | ttattagcgt | ctcagactca | aatcattcaa | aatcttcttc | ttactccttc | 1380 |
| ttaatatcat | atcaaaatat | attaaaatat | agggaaaatt | tgcgtccaat | aggatttgaa | 1440 |
| cctataccaa | aggtttagaa | gacctctgtc | ctatccatta | gacaatggac | gcttttttc | 1500 |
| gtattttgac | tcgcctcttt | cttctttttt | caaacaagaa | gagaataata | ataggatttt | 1560 |
| ttggagagaa | ttttgagag | aattttggca | attgtatatt | caatgatgaa | tagtggattt | 1620 |
| cttactataa | aaataataga | taaaaatatt | agactagaga | atagaggatc | tagagcgggt | 1680 |
| agcgggaatc | gaacccgcat | cgttagcttg | gaaggctagg | ggttatagtc | gacgtcaatt | 1740 |
| cagcttttt | aacgtctcta | attcaaaacc | gaacatgaaa | ctttggtttc | attcggctcc | 1800 |
| tttatggaag | atagaaaaat | ttctagattt | aagataagat | gtgaatcaac | taaaaaaaaa | 1860 |
| tatatacccca | taccatctat | gtcagctttt | tgtctgaata | cattcaaaac | gactcgcttt | 1920 |
| ctagatgatc | cctctagaag | aaggagatta | taacaatctt | tctagttact | tcgttctcta | 1980 |
| tttctatttg | tttgaaagga | tccgaaaagg | aaaagattt | tctttccacc | gagctaaaat | 2040 |
| aatacgacca | tgtctctagt | aaactaaaga | catcgcatca | tagctagttt | gcttcaattt | 2100 |

```
tttctctaca aatcaaaaca aaagttgaag atttagttac gattagaaat ctactttat    2160
atcttcatcc atggacctct tactcatact cattcaattg gaagtattga tccaattgaa    2220
aaattttgtt tcacaatttc ataatccaat ttttccattt ttaagtggcc tttgaataga    2280
aatcgcgaga atttctattt ttccccaaat gtgttattga gaggtaaagg attaaatccc    2340
cttaagaaat aaagttttg gtcggaatat gaattaaacc gaaataccc ttaactatta    2400
aggagattaa tagaacgaat cacacttta ccactaaact atacccgcta caatgctatt    2460
attatataat aatggggcct tttgtcgaac agaggacttg cgtgtagtca aaaaaaatca    2520
tgaaaattgg agagatacta ttttgcgtcg gggttttcac ttttatgaga ttcggggaag    2580
aggtcaatta ataccaagt tttatttttt ggaagagtgt tgctagatac ggctcaccaa    2640
aatcgttcaa atcacaacaa aaaagcattg tgtaaggttt tattttattt atgccagaaa    2700
ggcggtcaag taactaaaaa aggaagaaaa aataatacga aacggtcctt ttatataatc    2760
aggtagagaa agttttttag taagtatgga aatagtcctt cttctttatt ggtcttgctt    2820
gaatatatat tatttaatct aataatagta agcattttg ttttcaaatt agagaaattt    2880
aaccagaatt cgctggaaca aaaaaaaagc ccggctgagt agtgaccgag ccaggctgta    2940
gaaaaaaggg cccttcgaag aaaatcaaag caaggaggtc ctctttcttt atctttctat    3000
ttctttggat tagatctttt gagtctttac ttgaatctaa aaggaattgc taataaaagt    3060
tttacatatc tttacatatc tatataatct atataataaa gataaagaag gagaaagaac    3120
gactttttg aatccttact tcatttggaa tgcaacatat ataataatta gaattatctt    3180
tttcaattgg gagagatggc tgagtggacg aaagcgtcgg attgctaatc cgttgtacga    3240
gttattcgta ccgagggttc gaacccctct cttccgtttt tcatcgagaa cttaatattt    3300
tcttcttttt ttttttttca aatttcgaaa accctttttc ctatttaaac gtctgaaata    3360
gataaaacat cctaagaaac taaaaaataa agctcgaaaa actaaaaaac cttttttatt    3420
tgattaatta tatattattc ttcacgtcca ggattacggc ctgggtcatt agataggaat    3480
ccaaagatga agagagaaac aaagaagatt accactgtgt aaacgaaaag tttgagagta    3540
agcattacac aatctccaag aacatttttt gaaaaaaaaa acgagaaaag agaatagatc    3600
gtccatttt atagcattct attttgacac caagaaagga agtgctttat agaaatataa    3660
aatcattgga ataaattcaa attaatttga aaaaaaaaaa gcgtctttga ttcccaaaaa    3720
ttattttcat acccacaatt agattattag atattggcgg gggaccctaa ccctataaaa    3780
aatataataa aaaagatat ttaagaccct tcattggaaa aggaaaaggg ccagaatggg    3840
gaaatctgac gagccggatt tgatttatcg tcgctatcca cgaattcaat ggttgaattg    3900
aaggttgata ctgtaaagac ttatttgatc ttatcaattg gtctcatttt tttcgaagaa    3960
atcatgaatt ttctaagata gtattaagta tcttatcgaa aacttacagc ggcttgccaa    4020
acaaggcta aaagaaaaaa aaacacaggt atgattggca taacatctat gattggattc    4080
aaaaaagcat aggcctcggg caatttggcg aagaaaagac tagtcatata aagggcagaa    4140
ttaagacaga tacagctcaa actaaagata ttaagcataa cagacatttt gttcttggag    4200
ataattgcaa tttgattgag ttcttgatat aaggaaaaat gaagaaagta aggtagacaa    4260
aaaatccttc ttttctttg aacctgtcca accaaaaatc caccaattct caaaagagaa    4320
tagaagaaat catatttca tctactattt taattgaatt atatgtaatg atcaataaat    4380
tcagttgaat tctatatcta cacgtgtcaa attcctagca cgaatttaga atctatattt    4440
ttaggttcaa ataaaatcta taaatatctg atatctatag atatagatag gatatcgaac    4500
```

```
ttcgaactac aaaaaaacat taccctcgtt atagagaatt atatagaaaa agatagacaa    4560
aaaatatgag gtgttaacaa ccgggcatgc cccggagtat aatacttgtg aagtcttggc    4620
gcgtggccga gcggtagtga attgttttag aagtgaatta gtcaatatac ttttcatgtc    4680
gaatcaggat caactaggac agaaataaag cattgggttg aactcttctt tggtgtcaag    4740
```

<210> SEQ ID NO 7
<211> LENGTH: 2030
<212> TYPE: DNA
<213> ORGANISM: Artificial Sequence
<220> FEATURE:
<223> OTHER INFORMATION: CL11954.Contig2_All

<400> SEQUENCE: 7

```
aaaccacaat ccaaaagaat gaaatttatg gcacctaatg ccaaatattt gtacattagg      60
aagtagcgcc gtgtgaattc aatcatagac ttgcaccatt ggagcttcag atgagaatga     120
aacttattca aacagaaaga atagataaaa acaacaatga agctagtgta cagagcaata     180
attagaataa catgaagctg gaagcataca tcttctataa tcgattctac aggaatgggc     240
atcttactat gatcatggtg ccgcgcttag agaatattag gatgatgaaa tattaaagca     300
aatctcaaga ccgttgccgc caattccagc aatcttacac tggaatccac atgactctag     360
ctcagcgatc actttatcaa caactgtccc tgataaaagt gtcggtaata gtgtcaacac     420
acagccacct ccacctgctc cagtcaactt agaagccagc ttgtacttca atgttgtccg     480
tagcacagtt tctatagaag catggctgac ccccatgcat tggagcaaac cttgattcat     540
ttccattagc tcttctactt tctcttcctt ctcaactata tcaaggtcgg cagaagaagc     600
tgattggatt atggtagcca gttcattgct gatagaatcc acagcagtga acacagcagt     660
catagcattt ggatgtctga ctgccctctc cgagacacta gcaactaaag cctttgtgtt     720
tctcccaact tttgtgtcag ttatgagcat tttaagtgcc atattggact tgattcgtgc     780
gagaccacca gacttgtact tgatcatgtt gccatatgtg cttactgtgt tgtcaatacc     840
agatggcttc ccatgaatta tcttttcacc ttcgaaagcc catttgttaa ccaattccag     900
ctgactatct tcaaacgtta accagccttc acgactgaag tcctgatttc cagaatccga     960
caaagcaatc agggcagctg caagtgagac acagaatgca gcagatgaac ccaagcctgc    1020
acctaaagga agctcagaat tgactaccac ctttgcaggt ttatacccctt gaacagaggt    1080 gtatagccag agaaaagctg tcactccagc agcaagtcca attttttgcct ctggaatatt    1140 ctgttcttca actagagttg caattagttt gagagtgtct ggtgggcatg aagtgggaga    1200
tgaagcaatg caaccactcg attcaggaaa tgcttcttta attcttccaa ctggccatga    1260
taattctaag ccgatatcct tcagctggag atttagtgta tcgtgattat cggaaggagt    1320
aggaaatcga agggagacgt aagtgtagag atcaatggag gcagcgactg cagcggatcc    1380
atggacgaca gcatgttcgc cggcaagtat gattgttccc ggagctcttg ctctcacctc    1440
catactctaa aattgttgtt tgctattggt ttgacctcgc actaccgtct agaaaattca    1500
ctaacaaatt ttttttttgt atatccggta tcccagaggc ggtgcttggg aactcaccaa    1560
gtccgatact gcttgcgacg gggaaccgtt tgcgtgactt tgccaaagtt ctagatctga    1620
atttcgagtt cgaaccggtt ttgactccga ttcagaatct aaacgagcct agctttcggg    1680
ttaatccgaa tgagttcctg gccgtgaatt tcatgctcca attatataat ttgcttgacg    1740
agacaaacac tggagtggaa acggcgctca aacttgccaa atctctcaat ccaagcattg    1800
```

| | |
|---|---|
| tcacgttagg tgaatacgaa gcaagcttaa accaggtcaa gtttctgacc cggttcaaaa | 1860 |
| acgcactcaa atactactcc aatattttcg tctcactcga acccaacttg acccgagact | 1920 |
| ccccggagcg cctcaaggta gaaagattat tatttgggcg acgcattgcg gcggtgatcg | 1980 |
| gaccggagga accgggaacg agaagagaac gtatggaaga caaagagcaa | 2030 |

```
<210> SEQ ID NO 8
<211> LENGTH: 2257
<212> TYPE: DNA
<213> ORGANISM: Artificial Sequence
<220> FEATURE:
<223> OTHER INFORMATION: Unigene202_All

<400> SEQUENCE: 8
```

| | |
|---|---|
| aatgtaatta agatagttct cgaatcaaat catattataa atgagttctt aacatgtgca | 60 |
| tttaagatac gtattagctt ttatcaaaat gagttggaat tatcgatctt aaaagcacac | 120 |
| ttaatattgc aatctatagt aaatttaaaa aaaacaacaa ccaactcaaa caactagtct | 180 |
| ttaatctcca aacgtggcaa taaaattctt aagcactaaa agatcgactt gaatgggttc | 240 |
| ccggcccagc ctatggctat tggctaggca gtgtaagcac ttggaagcag ccttggagta | 300 |
| acactggccg aaagaggcac agccttttgc aatgcgatcc caaagctctc ttccatgtca | 360 |
| actgcaacga ctccgtcagg taatttccaa tcaaatgagt gaaccaatgt acccaaaatg | 420 |
| tactcaacca ttccgattcc cattctagcc ccggcacaaa tcctccgtcc ggccccgaaa | 480 |
| ggaatcagct cgaaattatt tcctcgagga tcaatgttcg catactttcc actcaaaaat | 540 |
| ctttcggggg tgaaatccaa cgggttttcc cacacgttag ggtctctccc gattgcccat | 600 |
| atgttgacaa taagtctagt gttttttgggt acgtaaaaac cgtctacttg acatgcttcg | 660 |
| cttgaaaccc gagggagatt taagggtgta gaagggtgtt ttctgaatgt ttcttttgcat | 720 |
| atggccttta agtaaggcag tttcggtatg tcggattctt cgagtcttcg gtttctgccg | 780 |
| ataacttgat ccatttcttc ttgtgcccga ttcaggatgc gtgggttgtt caacatctca | 840 |
| gttagtgccc attcaatgat gcttgatgat gtatcagtcc ccgccgtgaa taaatcctag | 900 |
| caaaatcatc attttattta gtagtattaa ttacaagatg atttggtaaa tgtcaatgta | 960 |
| tgcctgatca gcaagtgaga ttgaaaggag gggaaaaaag ttggaaaaac tctgtaaact | 1020 |
| ctcacagcta atgagaaact agctgttcat ttttattttat tttattttttt ctgtttaaat | 1080 |
| tagtgatttg ttcgggtcaa tttgcgcaga agtcaactta aaacactgtt ttggattagt | 1140 |
| ctaatcgaaa aagagtaggc ctcctgtaaa atcgtcttac ggtcttaatt cgtgcggagt | 1200 |
| ctcactctct tacagctcag tccagcaaca tacgataggt cgggtcagga agatccgtct | 1260 |
| tacagaaaat actcgtaaga tggtcttttt aaaaattttg tcatcgaaaa attacctcac | 1320 |
| tggtgctttt ttttttttttt taattattaa ttattttcca aggtatctct agacccaaag | 1380 |
| gccaaaaact aatccctcga tgaatagcac tataagggcg ataaagactc tctctaccaa | 1440 |
| gtgttaacat aacatgtacc aattctttct catcatgtac accaagacat cactagcgct | 1500 |
| ccatacgtaa acctgtcaaa cgcttccgcc gacaatcaga caggatcctc tttagaacac | 1560 |
| ttttaaaat agaggatcct ataagttcac ctccttgttta gctcacattt gtttgttgga | 1620 |
| tacaagaatt aattggagtg gttagtcatt aattggaaaa tggttacaat ttgttttgtt | 1680 |
| ttgaacaaca ttattgtttt tattactatt agtattatta tttgtagctt aacagaaga | 1740 |
| gattgaagtt gaaacttaca actgggcggg ccacgtactc ctataaaatg attaattgac | 1800 |
| tttaggttat tagaataata ccgtatttaa atcttcatta tatctcactc tctatcacac | 1860 |

```
ttcgtgtcac acttaatctt aactttacac gtgtgtttgt tattttaact tgttttcttc   1920
ttataatttt tacaaagaaa tgtgtaaggt tgagattcaa tggaacagag aatgtgatag   1980
ggatgtattg ctttcattgt ccattgagag atgataaata gtaaagataa atttggcaac   2040
ttcattcaaa aaagaatat ttattttaag ccaaaaatat ttcaaaaaaa gggacagtca    2100
tgaatttagg acctagagag taatattttt attaacactt aaaacatcat cttttgccac   2160
aataaattac atgaaactat gagaaatttt ataatgaaaa aagtagaaga ggggaaaatc   2220
tctctctctc tctctctctc tctctctctc tctctct                           2257

<210> SEQ ID NO 9
<211> LENGTH: 1946
<212> TYPE: DNA
<213> ORGANISM: Artificial Sequence
<220> FEATURE:
<223> OTHER INFORMATION: Unigene12268_All

<400> SEQUENCE: 9
ggaaccctgg aaatcaaatg tttgttccga taacgggaaa gtttctccct cttatcttag     60
ttgcggcaaa gactgaaatc ctgaacatag caagcatagc cagaagtgac tttgcagtga    120
aagtcaaatc tacggaaaga aaggatgaat gcggcaccta ggcccaaagg aggctgcttc    180
gctgaatttg gttgcatttt ggaacaattc cttgactctc tttccaatgc cagacccttc    240
atagcccatc caatgaaaga gctgggcggg gaggcgagac tagttatcag gtcagagaaa    300
ggcctcgccc gtaaactggc ccccttaaaa agccattact taataaggat ttcttacgcg    360
cgatatgccg acgacttact actgggaatc gtgggtgccg tagaccttct catagaaata    420
gaaaaaggga tcgcccactt cctacaatcc ggcctgaacc tttggatagg ctccgcagga    480
tcaagaagaa tagctgcacg gagtacggta gaattcctcg gtgcggtcat cgggaagtc     540 cctcagagga cgactcctat acaattcttg cgagagctgg agaagcgtct acgagtaaaa    600
gaccgtatcc atataactgc ttgccaccta cgctccggca tccattccaa gtttaggaac    660
ctaggtaaga ctatcccgat caaagagctg acgaagggga tgagcggaag agggagtcta    720
ctggacgccg ttcaactagc ggacactgtt gtcagagctg gagtaagaaa tccccaagtg    780
agcctattat gggggaccgt aaagcacatc cggcaaggat caagggcgat ctccttcttg    840
cataactcgg gtcggactaa ggtgccatcg gacggtcaag aggcagtctc acgatcggcc    900
atgagtgccc ggaagttcga attctatact cccgcgggtc ggaaggcgaa gggcgaaaga    960
gggggacagt gggcgagatc tatcagcagc gaattcccta tacaaataga ggcgcctatc   1020
aaaaagatag tccgacggct tcgggatcgg ggtctcatta gccgaagaag accctggcca   1080
atccacgtgg cctgcttgac gaacgtcagc gacggagaca tcgtaaattg gtttgcgggc   1140
atcgcgataa gtcttctgtc ctactacagg tgctgcgaca acctttatca agtccgaagg   1200
attgtcgact accagatccg ctggtctgca atattcaccc tggcccacaa gcacaaatcc   1260
tcggcgcgaa atataatcct aaagtactcc aaagacttaa atatagtcaa taaagaaggt   1320
ggtaagaccc ttgcagaatt ccccaacagc atagagcttg ggaagctcgg acccggtcaa   1380
gataggaaga agaaggagca ctcaactact agtccagtct aatagtcctt tttttctatt   1440
agttgcgcta gcttccgtac cagcaagcca gaccaaccct cagccaaagc aatactaagc   1500
gagaaaagat ctttcgcact tattagtcaa gcaagcagaa cctttattga cgttctgaaa   1560
gaaaagaagg aaggctttca ccctacagtg gacttgaatc aaatcaatca atgaatgaaa   1620
```

```
aagaaagcgc ttaccgagaa agagaaagga aggacaagtt ggtttgagga cccccttggtc    1680 aaaggaaaag ggaggtcctg attccgggac ggagccgtat gaggcgagag tctcacgtac    1740
ggttcctttg agaaggctgt gataccacca cctatcaggc ccgacgagcg gtccacggag    1800
ctgcatcctt actcacctgg tctatgcaca ttgctctttc taggaggttg gctgcctatc    1860
ttagatcttc ccattttaaa taagatcccg ggctcgatct ggtttagtat caaggtcatt    1920
ctctttctgt tcctatatat atgggt                                          1946

<210> SEQ ID NO 10
<211> LENGTH: 1451
<212> TYPE: DNA
<213> ORGANISM: Artificial Sequence
<220> FEATURE:
<223> OTHER INFORMATION: Unigene15281_All

<400> SEQUENCE: 10
gggctttgca tctgacattc gttggcccgg gagcccgcgt cccggccttt ttgtgcaata      60 aaccccctccg gccgaagact agtggtaggt ggtccagcgg agcttcgga aaagggtagc    120 ctagtgtgta agcacagcaa tgaaccgcgg cgaaccctca gacgacctat ctaagattag    180
gggggagatc ctcagtagtg gtgacccttt cactcttcca cggactgata catgtaccga    240
atgctcatag gggaaagttg actcctgggt ctggaacctg gggctggct ccgagaaatc     300 ctttctttct cgtccactca gggggtgcg gacacacctg cgcggattac aggtgacagt     360
tacaagaatg gcggggaagt taagagtacc cgacgacatt cagggatgga tgtagaccca    420
tcggtcaggg ataatcattc cggtcctggg agaggtggcg accattctca agaaggaaaa    480
agactgagct gagggaaggc ctaatgactg acttcaagga cgactggaca gccgggagca    540 aaaaagggggc tttgctcccc gttagaatat gaagaaagaa ataagggttg aagtttagac    600
cgctcacact aattctacct atagaaagga tcatgaaaga ggcgatcaga atggtactag    660
aattcattta cgattccgag tttccagaca catcgcactt ccgctcgggt cgaggctgcc    720
actcggccct aagacggatg aaagaagagt ggggaacctc tcgctggttt ttggaattcg    780
acatcaggaa gtcttttcac aacatcgacc gacatcgact catctccatc tttaaggaag    840
agatcgacga ccccaagttc ttttactcca ttcagaaagt cttttccgcc ggacgacttg    900
gaggggctga aagggctct gactccgtcc cacacagtgt attactatcg gccctactag     960
gaaagatcta cctacacaag ctcgatcagg agatagggag gatccaagag aagtacgaaa   1020
ttccgattgt tcagagaatc agattggttc tattaaggac aagtcctatt gatgaccaag   1080
aagactctgg agaagaagga agcttcaacc ctccccaaga cattcaagcc atcattgtgg   1140
gcaggctaaa gagcatccaa cgaaaagcgg ccttttcattc ccttctttcg tcgtggcaca   1200
ctctccccac aagcacccca cggctcaggg gggaccagaa aaggcctttc gttttccccc   1260
attcgtccgc ccttaccgcc tttcttaaca agccctcgag cctactttgc gccgccttcc   1320
taatagaagc cgccgggttg agccctcagg ccgaattcta tggtagagag cgctgtaata   1380
agaattgggc catgagagac tttttttaagt attgtaaaag aaagggcctg ctgatagagc   1440
tgggcgggga g                                                         1451

<210> SEQ ID NO 11
<211> LENGTH: 6970
<212> TYPE: DNA
<213> ORGANISM: Artificial Sequence
<220> FEATURE:
<223> OTHER INFORMATION: CL7827.Contig1_All
```

<400> SEQUENCE: 11

```
ccgcttcttc ccctgattga gcaacaggaa gaaggattga gcgcgttcaa aggcccttgc    60
gcaagaagga aaggattgag gtcagacggt cgaaagccct ttcgccttag ctcattctca   120
gactccatga atagaagtca atgcgcttct gcgcttacgc gcactcgcat gcctgtccct   180
ttctgcagta gtgggacttg ctccgtctag gcttagcgca tgcctgtcac tttaacggtt   240
ttctttttc tttcattttc cttatttcaa gtgcaagatc tttcctttag tacgagatgg    300
cttcacacct cgcggtgctt acacctctcg cctatcgaag ttctcttcaa aaacctcgtc   360
cgagaacttg tatagagaag gatttcccgc gttgcagcag ttcttccata ccaacttagc   420
tacccggcgc tgctattggc ataacaagcg gtacaccata ggttggccca acccagtcct   480
ctcgtactag ggttggcttc tcgcagttct ccctttcaca ccaacggtag ataggaaccg   540
aactgtctca cgacgttcta aacccaactc acgtaccact tgaatcggcg aacaaccgaa   600
cccttgggac cttcttcaac cccaggatgt gatgagtcga catcgaggtg ccaaacgact   660
ccgtcgataa gagctcttgg gagtcatcag cctgttatcc ccggcgtacc tttgatccgt   720
tgagcgagag cccttccaca cgggactccc ggatcactat ggccgacttt cgtctctgtt   780
cgaccagtcg gtctcacagt caggcaggct tataccatta cgctcacgag cagaatctga   840
gcttgagcct accttcgcac acctccggta ctctttagga ggcatccgcc ccagataaac   900
tagccacctc gcactgtccc gcctccgta gatcggtgtg gcggttaggc atccttagac    960
gaaagagtgg tctttcagga ttggtccttg tctgtcaaga cctcccacct atcctacaca  1020
ttcgatcaag gttgtcacta cgaagctata gtgaaggtgc acggggtctt accgtctagc  1080
cgttggtact ccgcatcttc acggagaatt caatttcacc gagtccatgt cggagacagc  1140
ggggcagtcg ttacaccatt cgtgcaggtc gctacttatg cgacaaggaa tttcgctacc  1200
ttaggacagt tagagttact gccgccgttt accgggcttt tcattcaaag caactaagac  1260
ttctccttcc gaccttccag caccgggcag gtgtcagact ctatacatcg tcttacgact  1320
tagcagagtc ctgtgttttt aataaacagt cgctaccccc tggtatgtgc cgctttccta  1380
agaaaaggag agcaccccctt ctcccgaagt tacggggtca ttttgccgag ttccttcgac  1440
atggttctct caaaggccct agtatactct acttgtgaac ctgtgtcggt ttggggtacg  1500
gtcagttcac cgggaggatc gccctcccaa ttcgaagttt tttcctggaa gattcaacct  1560
tcttgactat gacaagagtc gcgactataa agagactcgc aactataggc agggctggtg  1620
cgctctgctc tctcgcgacc tccactctaa tcaaaagact aaaggcgacc gggccagacc  1680
gagaaaaggt gaagatgact caaggtgcat attggggaaa ggagagtgag gggaagggat  1740
gagaccgccc gatcatccaa ttcactccaa gagagaggga tggttctgta gtccatttc   1800
ttcgtcactc tcgtataccc atcggtacgc ccttgcgggc cttccttagg gaccgattca  1860
ctctgcgtag attgactgaa cgcagaaaac ctttcactgg caggctctca tgttttcac   1920
aggatttctc gttactcatg tcagcattct cacttctgat atctccaggt cttgtcacca  1980
aaaaccttcg ccgattgaca gaacgttccg ctactgacac ttgaaaaagg atattcttc   2040
aaggtctcgt cgcttcggtg aatcacttga gccctgatac attttcggtg ccatggagct  2100
agaccagtga gctattacgc tttcttcaaa ggatggctgc ttccaagccc acctcctggt  2160
tgtcatcgct cgatcacttc cttttccact aagtgattgc ttagggacct tagcgtacga  2220
tctgggctgt ttccctctcg actttggatc ttagcaccca aaaagtctgt ctgtacaaag  2280
```

-continued

```
gagaatggcc tgtattcgga gttttccttgg gcttggtaag gttttcttag gccaccctag    2340
cccattgagt gctctacctc gggccatcga cagaatacgc tctactgaaa tagatttcgc    2400
ggaaaaccag ctatatccga tcttggttgg cctttcaccc ctagccacaa gtcatccccg    2460
cattttgcca catacgtggg ttcggtcctc caaggcctgt tagagctctc ttcaacctgc    2520
tcatggctag atcgatcggt tcgggtcaa ataggaagaa ctagaagatt caacctctgg    2580
aaagcgccta cacctaatgg cttaagccgc tcttcccatt tactcgctga cccatcatgc    2640
aaaaggtagg ccggtagact cagtgccctt aactaagaaa gtcaaggagc gaggctgaaa    2700
ccttcgactg attgttcgca tcggatttca ggttctctat tgcactccct aaatagggtt    2760
cttttcacct ttccctcacg gtacttgtgc gctatcggtc attgaggaat acttaggctt    2820
agagggtggt cccctttct cgcgtaaaag cgatcagaat tcgaacaggc cgcgttttac    2880
tgggaaggat cgaagcatgt gaacaaatct acagggctat caccttcttt ggccagatct    2940
tccaaccttt tcacaaagtt cactgcgccc ttgacaaaac taagagaata gtgccgtcaa    3000
gaggctaaat tttccatcat ccaatccaaa aagaaagaga atgaaagctg gcgaaaaaga    3060
aatgaaaact gtcttttcgat gcaaagcccc aatccgctct cgctcgccgc tactaacggg    3120
gtctcggttg atttcccttc ctttagctag tcagatgttt cagttcgcta agtttgaaaa    3180
gtccaaagag cgaagactag ccacggagct tggatacggt ttcccgatag gaaatccatg    3240
gatcacagac gagatctccc catggccttt cgcctctgaa agcgtccttc cttctcaatg    3300
cccgggcatc catccaatgc atgatttcg ttagaaccat gacagaagaa gtctgcttcc    3360
ttctatgtag agctcacttc ctcgattatg taattccaaa agcgcagggc ggggtccgca    3420
cccaggtccg caggagtttg agcatttaag ctctccaggt ggcgagctac gtcaaaactg    3480
ctgtgtgatg gaggaaggga taagttatgt aactgaaagc aatgatcgat caagggttct    3540
cccttgttaa gcaagagctc atggctatcg actggatccg ctttgagact ttctaagcca    3600
aagaattcat aggggctgta tcgacaggct caatttccct cttcgtcggc ttaccaaata    3660
agcacgccaa aaatgctttt catggcataa agcatgccct cagagccccc cgctaacgca    3720
gcatcagtgg tgctacgact ttttaaggga agaaggttgg ttaccggcta tactaagacc    3780
gcttttcccc cgaaaagaga tgacgaaggc catgatagag atgtgcagac agggctaagg    3840
cagtaatctc taaggagatt gggatgagct ttgatgaata aaagacgaat tggtcgaaag    3900
agggatagat gaagcaaatc aaaggaattt tcagacaaag aagagaaaaa aggaagacta    3960
tagtggctag gaaagctccg gctattctat tgaaaatgga aaaggtcgaa gtaagctgcg    4020
gcttataaat aggaagatga ggagataagg gtcgaaggag aggcatgata gacgcttttg    4080
gatctttctt cgctcttctc gcggagcgga ataccggaaa aaaaggatag ataactatgg    4140
gcaggaaggg ggtcagtact tggtccctct cccttagcct cttccactt ccgtcgttca    4200 ggaagaaaaa cttcgcctaa ttcttttgaa tcccttccct cttcccccc cactaactaa    4260 gacggttagg accactgaac aaacttggtt gacaaacata gttatgcgc tgctaatgta    4320 gcggcttgtc gagcatttga aaagtcaca ccatccattt caaataggat ttgtcccgtg    4380
gacacacgag caatccaacc cgtaggattt ccttttcctc ttcccattct gacttcagtt    4440
ggtttcgcgg taatagggag atctgcgaaa actcttaccc atatctttcc atttcttcgg    4500
aattgtccgc tcatagaacg atggaagtgt cctactatag cgcgacgtgc tgcttcaatg    4560
gctcgatatg aaagacgacc agctctacaa cttgaatgc catatcttcc aaaagcaagt    4620
tgtgtaccat ctgctttgca agccctacta gatctgcctt tacgagattt cttatatttc    4680
```

```
gtacgtttcg gatatagcac gtcctctttc tttttgacta tatgaaatcc acactttgac    4740
acctaagatt ccgtaacgag tagatacttc tgcagaagca taatctattt tctggtgaaa    4800
tacattacaa gatgtttttc tatactttcc gcatttcgtt ctagctattt ctgccccttc    4860
taatcgacct gaacaagata tacgatcccc ctccacgccc tttttcattc ctaatggaat    4920
atctttcact atttgacaaa aaatggaacg aaatgatctg cttttcttcc tcagttgaaa    4980
agagatatct tgagcaatca gagaagcgct ttgataaaga gatttgatct tgaccgagta    5040
aattaaggta ttagttgccg ttctattaga caagaaggat cgagattttc tcacttcgtt    5100
caaataagag ttgtacccgt acggaattct tctctttctc agtatgatct ccatcatcat    5160
ctctattccc tttctcaatt ctcctatacc acctaggtct atgaatttct ctatcaatct    5220
tctctttacc ttatccttag ttatgagatt ccagtttgcc cttaattgac gtaggactag    5280
ttcccgggca tagtcaaaaa gaaggttctt atcgacccca agcccatccc ttagaaagaa    5340
aaaggtagca ccgaagaaag gaaagaggga gatgcttctt ttttttcttc ccagatgatt    5400
cgcttcgcga atgaagtgag taaaggtcaa cctctttttg tcttcggtca cagagctggt    5460
cgcaaaaata gcgaaacgta ttctcttatc taagcctctt ccctgtgcat taagtccgcc    5520
catcgtagat ggttcaacca cgcccggtgc cacgaaatga ttgagaactg cgacgggatc    5580
gaaatgcatt tcttctttc tattcaataa gtattgcatg accgaataat tcaaggaagg    5640
gcgcactgcg gagacggtcc ttctaagtct atacctcgtc gggcggctgt cgtaggcgga    5700 ctttttttc ttaaagaagt tgaataactt cctttttctt aaagacttgt cctttttcat    5760
cagtatcagg aaggatacgt catttatatg cctggcgtat ttcgggtgct tgaccccgct    5820
ggcccgaagt aatttagaaa gattcttctt gatccggtct ccttccggcc ttcttttctt    5880
gtccatctta ggcgggattc cgcgcctgat cgactccact ctttttccctg ccccccggcc    5940 tctcacttcc tttccttctt cttttgtacc ctcccttgaa tgaagacagc tgatcggccc    6000
gactttacga aatgtacacc accagcccct cactttcttt ctgagtctgg atcttgcgcg    6060
tcttttccgt cttttccgtc cttttgtcg atggggaaga aagaaatgaa tgaatttttct    6120 tttgggaaag tgtataataa tacacctacc gagacgaaag ccaaaggtcc gtctcgtagg    6180
tggacgtatc gaagcgaaat aagatctcag attgacatct tgatagacta atttaccata    6240
ataataatca ctgaaccaac ttgaatctga actacgattc tgatcaagtc ttaccgaaat    6300
tggatttcct tttcgtgcca tatgcgctta aaccttattt agatttcctt tgagattccc    6360
ggtccaataa tgctatctcg aaggtcgctc ttcccgggt ggaagaagaa gaagaggagg    6420
tctcgcagga tgccatttgg gctgcagcag acgctgaaca aaatgagtgg caaaacctcc    6480
tttcgtccaa ggagtggcag tcaacagatc gccatttcgc gatctgcgaa caaaaggtgg    6540
ccgccatttt tgagaaaagt cttttcaaact agttgtaggg aaaccttagc ctgaacataa    6600 cggggggaaga gggattaacg tcgacttctt cgacatgcac cgcttcgact caaataaaga    6660
gagattaaat catctcaagg cggtctttga atgtgtcgga aaccctcgaa gtcagatctg    6720
gcgtgaaatc cagggataga ttgaaagcta aagggctgg gacgaagcct gttgagaatg    6780
aaagacagaa agactcacta aatccagggc actcctacta gttgtaaaaa agaaatctg    6840 taccaggtaa agagaaccte cactccaacc ttgggaaaag aggttttca atccaatatt    6900 acacatatcc ataaacatct atccttccgt cataaggcat aaagaaagaa agcgactcca    6960
acttcctttt                                                          6970
```

<210> SEQ ID NO 12
<211> LENGTH: 10526
<212> TYPE: DNA
<213> ORGANISM: Artificial Sequence
<220> FEATURE:
<223> OTHER INFORMATION: >CL2802.Contig3_All

<400> SEQUENCE: 12

| | | | | | |
|---|---|---|---|---|---|
| atgatcatta | cgctttaagc | gggttattct | attccacctc | ttagaaagaa | cttaaattaa | 60 |
| aatacttaat | agcatgatcc | ttttctattt | tttagataga | ttaaattttc | gtaagagatt | 120 |
| cttgtacaca | aaaagaatct | ggccaattta | gaatattcgg | gtagagggcc | ccttagatag | 180 |
| cgaaagtgat | tccaaatagg | aattatggca | gcgcggctgt | ctagactgtt | taaaagacga | 240 |
| aattgaaaag | ggatacgatg | atgccgagag | agtctccgat | cgactgatag | aggggcgcgt | 300 |
| ctgacttcac | cccgattcga | agttccgctt | tgggttgcgt | tcgtttggtc | tctggagact | 360 |
| tcgctgaaac | tctacgaatt | tttcttggac | cttgccctaa | gtaacgagag | cgacataatg | 420 |
| acgcgacttc | gagaaattga | tcacaagaca | gcttcggctc | ccttccaagg | tgaatttgta | 480 |
| tgccccttca | gagataccct | ttataaagga | gaggatcgcc | ctaaagtccg | tcgcgcaggg | 540 |
| gcgctttgcg | ctttaccaaa | tatttgaccg | aagggtatcg | ccaagattcg | ggacgacata | 600 |
| attgttttc | taatcaaggt | atataatcaa | atgaatcttg | agtaactttg | aattcttgtg | 660 |
| gtatatgttt | accgcgtgga | attaaagcaa | aaagggtaa | aaaaaaaaa | aagaaatac | 720 |
| acgtatgaat | agttggttta | cattatgaaa | gaaatatgtt | atattagcta | gttagatttc | 780 |
| taagactttg | accttattca | ttctgccttt | ttttatgaat | ttttgataat | tcattttttt | 840 |
| ttaagaataa | aacctttgtt | acgtttccac | atcaaagtaa | atatagtact | attttttcta | 900 |
| tcgtttaatg | cctgttggtg | ttccaaaagt | acctttccta | attcctaaaa | aaaataatga | 960 |
| caaagacgaa | gataaagacg | aagatataga | caaagaagaa | gaggtatctt | ggcttgactt | 1020 |
| atacgaccga | ctttatcgaa | tcagaacact | ttttctattc | caagaactta | cgcaggaggt | 1080 |
| cacgaataac | attaccggcc | ttatggtata | tctgaatctc | gacgataata | ccctagagca | 1140 |
| attttttattc | ataaactcta | ctggtggaaa | aatggtgaat | ggactagctg | tgtatgacac | 1200 |
| gagtcaagca | gtagacccag | atgtacatac | actatgcgtg | ggattagccg | cttcaatggc | 1260 |
| agctttgatc | ctgtccggag | gagcactgac | caaacgtata | gcattccctc | acgcttggcg | 1320 |
| ccaatgaggt | tttatttgag | agaaaaaaga | agactatgcc | ttcgccatat | gaaataggaa | 1380 |
| tattaagtaa | taatagcatg | gcactttgaa | ttcgatatat | gaaagttttt | tattgttttt | 1440 |
| ttttcaaagc | attagattat | gtatcgagag | agtagtatga | gataaaaggt | atttctgatt | 1500 |
| tatgagataa | aagtatttc | tgatttatga | gataaaaggt | atttctgatt | tttcttatct | 1560 |
| atcgggagtc | tagttcagcg | tcacaaactt | ttttcacacc | ggaggtctct | taacaatatt | 1620 |
| tatgttatga | aggagtgaaa | aaaaagattc | ttttttttcct | taggttatttt | aatcaaataa | 1680 |
| aaaagcaact | ttgggattgc | ttaatcatag | acaaaaataa | atatataaag | caacggagcc | 1740 |
| atcatagtcc | ttttaactg | ccacgaaagg | aagggtggta | atttgatcat | ttaccaatcg | 1800 |
| gggtctaatc | gatccgatct | ttctctttct | ttgatcgagg | gtaaggatca | attttatgta | 1860 |
| gagccgtatg | caatgcataa | aagatgcctg | tacggttgtt | caattctatc | tttttttcttg | 1920 |
| ttattctttt | atctttcttt | tatcttccct | tcatcatgcg | aaatagaaga | accttttatt | 1980 |
| atattatttt | ttatattcta | gcatcagggt | aatgatccat | caaccaaaag | ttagtataac | 2040 |
| cggggagcct | ttgacccgcg | cggaggatgc | atacatggac | ctagacgaag | taaagatatt | 2100 |

```
acgcagaact gtcctataca attatgcaaa cagatcgccc atgcctctag aggttatagc    2160
tgcagacatg gaaagagata cttttatgtc accaacagag gcccaagctt atggaattat    2220
tgattctatc ggggttgact ggtagttcgt gtaaatctat gatttgagat tagccctatc    2280
aaccgaattt aataggagta atctggttag gattgatcta aaccatccca ttattatgtt    2340
gattcaacat gccaactatt aaacaactta ttcgaaatac aagacagcca atcagaaatg    2400
tcacaaaaac ccccgctctt aagagatgtc ctcaacgtcg aggaacgtgt actaggttgt    2460
atgtgcgact cgttcagatt atgagctaga acaaaggaaa gagaacaatt ttccagtatc    2520
aaagatcagt accggtgaat aggatagaat agaaaaatga actccattta ctatgtaaaa    2580
ctaagaaaat tgatcatatg cctttcattg tgtatgaaat ttatggtttc cattggtgta    2640
actccaatca tctcaattta agaattctcc attggtaaca aatggttatc cattaagcgg    2700
aagaaatctg gattcaaatt taaaaacaga agattgggt ggccctcttg caagaacgga    2760
ctaacagggt cagctaccca gccaaccctc ataattaaat accgttactg tataggtaga    2820
tcttgttgtg aaagacctag ttactggaaa agtcatgggt agagccaaag aatgtgaact    2880
atacaagtta acaataacat tgattaaaga aaattaaagg ctccggtgta tagagaagac    2940
ctcaccgttt aagaaggaac cagagaaacg atggaatcca ctatttcttt ctaatttta    3000 tttcttattc gagtttaaat acccagtaga atataattta ggatttcgag gtgaaatgcc    3060
tagaaaaaag caaaaatcgt ggttgggaag gttatagtag ccaaagccgt tggaattttg    3120
agtttataca ttggaaaaag ccgttttgtt attaatagac taggacagga aaagaataa    3180 ctgaaagaaa ggaaatcatt tagttattcg gaaaagtttg atttttgcat attcaatgac    3240
cagaactagc cggggatata tagctcggag acgtaaaaaa aaaacgctat caaactctcg    3300
gggagggcct tcaaggctta ttcgaactat gactcaacaa gaaataaaag ctttgtcttc    3360
gtctgatcgg gataggaata ggcaaaagag agattttcgt agtttgtgga tcactcgaat    3420
aaattcagta attcgtcaaa gctgggtata ctatagttat agtagattaa tccacgatct    3480
atacaagaga cagttgcttt ttaatcgtaa aatacttgcc caaatagcga tagcaaataa    3540
aaacagtctt tatgtgattt ccaatgagat cctaaaatca gaagtaaatt gggaggaatc    3600
tgccggagta atttaaatgg agttccccgg agaatgaact ccgggaaagg agggtcaaaa    3660
tgaataaaat atgaaaaaat aaagtaagca aagaaatat gaatcaacac attcaatcaa    3720 aaattttag tttgacttcg tacctgattt tttatttgtt tttgtcttat gacacgagaa    3780
tcaactccgg attgtcagat ttttcgaaca aagcatcaat ctgcctttga gttcgggtgt    3840
gaattttgct tcaagtgaag aaagggtaag cctattttt tgtctcgcgc gttcgccttt    3900
tatttctttt cgtctctcac agtcgacttt tctttctttc tgtctggctt tctgcctggc    3960
tttctgcctg gcttatattt cttttctagct ctcgcggtcg gcttgttttt ttcaaatagt    4020
gtctcattat taacaaaagg taacaaagat aaaatcgag cttgttttat agcacgagta    4080
attaatcgtt gttgtttcaa ggtcaattta tttactcgtc tagataatat ttttccttgt    4140
tcactaataa atcgactaat taaactcagg tttcgataat caattcgatc ccccggttgg    4200
attgggggca aacgcctacg aaaagattgc ttggatttaa gaaaagattg cttagattta    4260
agaaaaggtc gctgcttgga tttaagaaaa ggttgcttgg atttagccat ggtttgttta    4320
gtttattcct ttaaaccgag aatcctattt cggttggatc tataaaacga gaatacataa    4380
aaataaatag gatttggttg ttttctattt aaattagctt aaaattaatt ataacattct    4440
```

```
aattatataa ttagactttt cttttcctta ctcctcaagg gagtgctcgg ttcgagctat    4500
ttcgttatct ccccgtgaat cgtatgtttg taacaatatg gacagaattt tcttaattcc    4560
aatcgattag gcgtattgtg ccggttcttt tgagtaatat atctggaaat ccctgttgat    4620
accttattaa caaccttttc aacacaagta gtacattcca aaataatcgt tattcggata    4680
tccttaccct tagccatgaa cctccttggg atttttaatt tactcaatcc ttttcctttc    4740
gatacgaaag gaagacgaag aaagaaaaaa atagacgttc ctcacttgaa atcaaattct    4800
caaaaatttg taatcactct attaaaataa gatataaaga tttataaacg aaattacaaa    4860
tcacagtatt tcaaactata gtccagtatc tcgtttaagt agcttgtata atactcttcc    4920
ctcgacccac attttacatt ctacttacat tcctctatta tttattagag tagtatagaa    4980
ttcgaatttg aatccgagtc ccacagccgt taaaaccact tttattcttt ctctttcctc    5040 ccttttaaa aaagagaaaa gagaaataga gggggagatt ggttagtgac agatatttaa    5100
ttgtatctct aatcttcttt atgcgttccc acgttaataa ctagaatgaa aaaaagggga    5160
atgtcaacgc atctgggaaa aaacgattaa tctctatcaa tagacctgct aaagagccaa    5220
accatagagt acttagtacc ggtgccacgg aaagatatgt ttttagatct cgcattgaaa    5280 aaccccctt atttttgta gtacataaac atatatgatc agatgcatat gtagttaagg    5340
accacttagc attgtactct aatagtagac agaatcccta attcaaatgg aactggacaa    5400
tgatacagca aatcttttc ttaaaacaaa acataaaaac gtccttttct tcccgagccc    5460 ttcccccaaaa tactcatttc attttccaac gggttccgtt ccatctttca tagggatcga    5520 agtatttat tacgattcga tttcgattaa tattttaggt taaatgagac caaaagacg    5580 aaatggacag agaaattgta tagatctata tatatattct atagaagaaa aaacaatgtg    5640
gaaaacaaga caggaattct ctacaatgat acttaggcta attggaggga tgtagcgcag    5700
cttggtagcg cgtttgtttt gggtacaaaa tgtcacgggt tcaaatcctg tcatccctac    5760
gcctacccct acctattcct gttccctaga gcagtaacgg gggattcggt gaaatcgatt    5820
caaattggac gtatagaatc tttcagtctt atgatactat ctagtatata cataaaagat    5880
gtattgagct tacaaaaaga atccaattcc tttctttcca gtcttatctt ttttgataag    5940
acagcgctct tagttcagtt cggtagaacg tgggtctcca aaacccgatg tcgtaggttc    6000
aaatcctaca gagcgcgatt ccgttcttct tagatgtaac tagcttcact accttgaaca    6060
gcaatctgaa tttgacctcc tgaatattaa agacaggagg aggtcaatca gaaaacggga    6120
tcttaatgaa tcaaaggtcc aactgatcgc catgcctgta ttgtaaatat gcagttacaa    6180
ataatccagc caaagtaata ggaattaggc ctaagacgat tccaaataga aaaacttcaa    6240
tcatttcaat ttcttttgaaa ggagaaaaaa gaggtaatat ccatacctaa atattaatct    6300
gaattcccat caatctcaat gactaagaat ttgcaattga tacggtaagt aattatagag    6360
gacacagaat ttcgcagaaa gatttctttg tctaagtttt gtgcagttca aatatcaatt    6420
tcaaataagt cgtattttgc tcagcccgat atataaagct gaggttatag ttaaagccgc    6480
taatagaaaa ccgaaataac tagttatagt aagcatgaag gagctaaatg aaatatggtc    6540
tttttataca tatgtttata aaaaagcact tccctaagtt tctattttga caaaaaaaga    6600
ggagataaac aaaaatacca attgaaagtt tttgattcat ctatcattat agatagatag    6660
acaatactaa aaaagcgaaa gtaacaagca tgtaaaaaga aattggttca tcatctacga    6720
catctaccca ttctgtgctt gcaatcaaca gatttttta ggacctatca actcaactta    6780
gaaacgaata ataagaactg ggttgtgtaa cttcagtaac aattgggatt tccccttttt    6840
```

```
cttttctgac agaacaatca ctccccgaaa gaattctatc ttcctttcgt attattgcaa    6900 ttttgtctt tcttttataa taagattagt ctttattaat atagattaag attaatatga     6960
atctcattca aataatattt atttatatat acaaataaaa tgcagaatct aatgaatgag    7020
tcaggaatat gaataatgaa tccaaaattt ctctgaaatc atgaaaaact gaagtatact    7080
tcggatctaa tcctaccaat tatattgaca acttcaaaaa attgttcata taattgttat    7140
gatagcggtt gagcaagtat gccctcatcg tctagtggtt caggacatct ctctttcaag    7200
gagacaacgg ggattcgact tcccctgggg gtagggtact acgaaaagaa gttgggcagg    7260
gattaccaat acgcctaaaa agaattcttc ctgggtcgat gcccgagcgg ttaatgggga    7320
cggactgtaa attcgttggc aatatgtcta cgctggttca aatccagctc ggcccaacaa    7380
ttcaacaatc gaccatgaga tggtcgaacc cccctcttct ttcgaaatac cggatacggg    7440
ggaataaaaa agaatccaat tttatgctag atcccttatt tccctgggat tgtagttcaa    7500
ttggtcagag caccgccctg tcaaggcgga agctgcgggt tcgagcccg tcagtcccga     7560 cgaatctaat taagtacacc aatccgcctc tcctcttcct gtgaaagagg gtacatggag    7620
cagcatctca ttccccagag attcttttt tttccttct catcaaacat agccgttttg      7680
attacttcaa cgaggactta ttgaaaggag aaagacgtat atcgattagt tattggttgt    7740
ttattattat agttaagtat ttgaagagat actgagtctt cttttgaat tgatccccat     7800 ttatgtaatg gaacaaagtc cgatatcttt ctcgagcgca tatccagaga tggaattcgt    7860
ttcttgtata atacaaaatg aatttaaaaa aatttcccct tctagctctg tttttgtttg    7920
tgcaacctga attactaaat gtgcagttta gtaatcaatt ttattcaaat tggacatata    7980
tgtgtcccag tactaataac cgaggttaaa agaaagataa agatcaagca aggaaccct    8040 tccccctttt tcccaatgga ataaatcagt ttttccttac tatttttttt agggttcctg    8100
tccaagaaaa aacaaagcct aaaactaaaa tcaaataac gaaaatagtg aaaaaggtgg     8160
aaaattccat cttttttcca agactcagct ttatcacact tctttgtctt ccacagaaaa    8220
ttagatcata aaaaagggc gtttagggct tagcttttc cattttggtt gtcttgtttg      8280
ttggcggtgt gtaactaata gaaaggagtg ggtggtaaga tgagacttca tttgatgatt    8340
gtgtaagata ggttatagaa aataaacaac agaaagaat gctatataat gctaaataat     8400
agaggatttt ttgattgggc cgggaatcct atttcgtacc tatttcatat tcggtatgga    8460
taaaagattt cccgatgcta gattattcca gtttcgacaa cgaatttatt tgatagctta    8520
gatattgtta ttcatgatag tgatcggatt caatattgtc gaagggtagt tcattcattg    8580
aagttagagg cgcaagattt attatctcta ggggattaaa tcccgagtta ttgtgaagta    8640
aaaaaacaat gagattatgg aagtaaatat tcttgcattt attgctactg cactgttcat    8700
tttagttcct accgcttttc tacttatcat ttacgtaaaa acagtcagtc aaaataatta    8760
atttgaatga aacttgatct tatcaatggt tgaaaaaata aaataaaagg gattccaatt    8820
ttgcgtctta aatgatgaat aaatgaaatg ggcgggctat aatcggcagt attctatgag    8880
atccgatagt gatagtatgg taagaaagat tcatcgagtt cttcttacc ctactgtact     8940 attattggag tgtataaagt tattacttca taataaagct agaggcttaa tatagatcaa    9000
tctaccatat tatcttcata tcagatatgt agatatatta gtctcaatat tcattttata   9060
tcattttata tatggaattg acatagaacc caattctatt tctttcagac atttatttgt    9120
tccgatcaat cggaaagaat cgtttactc ttatagaatc cattcctcta gaatccaatg     9180
```

```
aaatttgaaa atgaagagat ctttatttta aatagtgcaa aatgctttgc agaatgagat      9240
ttataaaaca attgatagag tttgattcct caactctatc agtagtgctt ctagagaccg      9300
cttcttcccc atactacgag tgaaagagaa aatgtaaaga ctaccattaa agcagcccaa      9360
gcgagactta ctatatccat gtgaattatg cccctatct ctatgataga atcattccat       9420
tattgctcac ttataatagt gaaatccatg gtgcagagtc aaaaagggat tttgaccgaa      9480
gacttttcat gaatcaattc aataaatcca cttctaaaaa attcctctac gatttcttat      9540
cgggaaagac taaacacaag taaaaaacgc aatgacaccg caagggaatg gtatgaatgg      9600
acgttgacgc ctaaaaatta tttcttttg cactttttgt atcaattcta taaacaaaat       9660
aaattatcta tccactctaa tatttttaa atgtccaaac actcagagat tctcgcgagt       9720
ttggatatac aatatccaaa aaaatcttac gccccttttcc accattacta attgaatttg     9780
attcgctgtc ctacccgccg gctattggac tttaagatcc gattattagt attagtagta     9840
gaagggatcg ggaagtcttg atagcccttc gaccattaga atctttcctt aaatccttga     9900
tacaacgatt tacaatcttt tagaaaaccc atgaataggt gtttaaaatc aactaagtag     9960
caacagtccc gtccctttct tttgcttttg ctggggaata attcggcgag ttagatcagt    10020
agaatcgaat aagatatttc gattcttttg gtgatcaggc gacacccaga tttgaactgg    10080
ggaaaaggga tttgcagtcc cccgccttac cgctcggcca tgccgccaaa tgaatacata    10140
aacctatcgc ttttctattg aaaaaaacaa atgtggcttt tctctaaatt tatgaaaaat    10200
ttgaccccctt aactattcac tcctgactgc gaattcatga atggttcttg gatttgaatt    10260
tcgaattatc tttgcctaat gatataagaa aatacaaatt gatatataat caatcagtat    10320
tgagtctttt ccaaaaaaaa ttcttctcaa tttaaattat aacaacaatg agttttatat    10380
atcaaccccca gaacggaaat ttttacacag atagtcaatt ggctatctta tgtatatatg    10440
tttcccatag ggaattatca ggaaattctc gcgcgtcaaa ttttcattct ttaaacggtc    10500
aaagcgagct ctttctcctc aagtag                                          10526

<210> SEQ ID NO 13
<211> LENGTH: 9857
<212> TYPE: DNA
<213> ORGANISM: Artificial Sequence
<220> FEATURE:
<223> OTHER INFORMATION: CL10003.Contig2_All

<400> SEQUENCE: 13
ggcctgtcta attaaaatca actacattat tattgaaccc aaaagagagt atggatggct        60
ctgtagaaaa aaaaattaca atcccaatat caaaataccc tgtagtttat tatgtgagga       120
gacattttga atgacatacc ctgtggtaaa ttatgtgaaa cgcgacattt tgaatgtggc       180
gttatttgga catcggaaaa cacaaaggga caagaacagt acgacaaaaa gattttccag       240
tcctacccat gttttccgac acccaagaaa gcaaaaaatg tgctttaagt ccagttatct       300
ccaacatgac tactttatca ctgaatattc tctcctgaca tgatgccttg atacattgaa       360
atggtatgcc ttgtgtgtag aacaatctct agttgactcc gggtaacaat atcttacagc       420
ttcgatgtgc ttgctggcgg tgatgttttc gccttcctta ttaggccctc ctgggtgact       480
gatgctacaa gctggtgatc aacaatgttc aacataaata aaagtcagct ctaactaatg       540
ttcattcatc aggtagaaat atgaaagaaa aatttgttgt ctgacagccc aacagacgag       600
ggtcctgcca cagcagtgtc tctaaaagta gaaaggaaat gaatttgata gtccagaata       660
cagtttgatt ttgattcccc cttcgaaaaa gtgattattg acgagctaca gcaattgcac       720
```

```
ctattaacgc aactaaaaga attattgaaa tgagttcaaa tggaatacaa aaatctgttg    780
ataaatgaat cccaatttct tgactattat ttatcaaatc ttgctctata atctggtttg    840
attttgtagt ccaaataatc ccgtaccatg acgtatctag aatagtagta attagtgaag    900
caaaaagact tgtacaaacc accgaagtaa ccccatctcc aacggtccaa ggatgaaaat    960
ctttgtaata ttctgaacca ttcaggaaca tcacagcaaa aatgattaaa acatttatgg   1020
ctcctacgta aataaggagc tgcgcagcag ctacaaaatg ggagttcgat agaatataga   1080
ataaggatat acaaacaaga accaatccca aggaaaaggc agaataaatt ggattgggaa   1140
gtaataccac tcccagaccc cctaatataa gaactaatcc cagaaagact aaaagaaaat   1200
catgtattgg tccaggtaaa tccattctat ataaaaaaag agataaataa attgaaatct   1260
ttcataactt tattgacctg tccaggaaaa aagaagtcac tctattttt tatgatagtt   1320 cttaatttt aattgaattc cattttcatg tatgtgaatt gatgtcgata tagctattgg   1380
ctcaatttcc ttctttctcc gaaagagtcg ttttcctat atatttaac tattttgaaa   1440 tccttaatta tagatctaga atatttatat atgtatatat tctagatcta tataatacgg   1500
aaatggattt tgaatccaaa ttaacccacg atcttcacca actaataact agtttggatt   1560
tgtagttatt caccaagaaa aaaagcccat tcgtttagat caaactgatg agtgttatta   1620
attgggactt gctcttaaat caaacatttt gaatttgccc gaaattccaa attgttcgaa   1680
ttgtgtaatc gtcaattact gacattggta accgacccaa agcaatttga ttcaaattca   1740
attcgtgacg atcatacgta gaaagttcat attcttcagt catcgataaa caatttgttg   1800
gacaatactc aacgcaatta ccacaaaata tacagattcc taaatcaata ctgtaattaa   1860
gtaaccgttt ctttctaata tcagtttcca atttccaatc aacaacaggt agatctatag   1920
gacatacacg aacacatacc tcacaagcaa tgcatttatc aaattcaaag tggattcgac   1980
cgcggaaacg ctctgatgtg atcaattttt cgtaggggta ttgaatagtt acaggtaaac   2040
gattcgcgtg tgataaggta atcatgaaac cttgaccaat gtaccttgca gctcgtactg   2100
tttgttgacc ataattcatg aactcagtta ccatagggaa catatcgtga atatctataa   2160
aaaatttgat gcttgtttct ttctcttgtt tgggccaagt catgaatata gaatatcgta   2220
ttcttttaca gtgaaagaag ttggaaagaa gttgttaata atagattacc tagagaaata   2280
ggtaaaagaa atttccatcc aagatttaat agttggtcca ttctcagcct cggtaaagtc   2340
catcttgttg tgatagaaat gaacaagaac aaatatgttt tagctaatgt aataaagata   2400
ccaattagtg ttacaaagac tctacccgct ttttgattt caaaaagccc gggaacggat   2460
atgtgcggaa tagaaagatt ccaacccccc aagtaaagaa ctgttacaaa taatgaagaa   2520
actagtagat ttagatacga agcaacgtaa aataaaccaa atttgatacc cgaatattcg   2580
gtttgataac ctgctactaa ttcttcttct gcttctggta aatcaaaagg taatctctca   2640
cactcggcta gggaagaaat gagaaaaacg agaaagccta taggttgacg ccacaaattc   2700
catccccaaa aaccctgttt tgactgcgct tcaactatat caattgtact tgaactgtta   2760
gataatcgta gtcgacgata acatcactgt ttccatcgct attacaaaac cgtacatgag   2820
attttcatct catacggctc ctcgaaataa atctaaggac ccgttcgcta ttatttattt   2880
ggatatgttt gtaggataga tagaggcaaa atctatcgta aggtccccaa ttagacaatg   2940
gaattctgtc tgctatattt ataataaaaa aaagtgcttc tgaattgatc ttatcttta   3000 ataatttgca ttttctttg ttgagtaata acttaatcct tgaataaaat gtttcttgta   3060
```

```
agaatatcaa tatatatttc aacctagtgt tttcaagtac gaaaaacaac tagacaaaga    3120
tctcggtttt tctagtgcaa ttacatccac tctttctatt ttcttttttt tttcgttcct    3180
attctccttt ctcaaaaaaa ggggacttta aacaaagtta aaggattact tcgttcttga    3240
tagttattta cttaatcggt ggatagaagc atactctgga tcggaatcgt gaggagtact    3300
ccttgatcat ttctaccaat ttaaagcccc aatttgaatt cctttatgc gcagaaaaag     3360 actgttgaat aacttacata atccctatta cgaatccttt gtgtatcttg gtgttcctaa    3420
ctatccactc ttttttttgtc aatccatgtt agggtaatac gtacgctaat agatagtaaa  3480
aaccccatac ggttgatctt ttgaacccgc ttcaagccat gatgactaat caaccaatct    3540
tggggtaaac agcctctaat gcttatgttt acttttactt aactcttgta cataggaaat    3600
gagactcaat cttttactgc aactttataa gccgtttctt tcactcatat aactatctag    3660
tttagttcat caaccctcga atgatgaata aaaaataaaa atatatattc aactcatgac    3720
acttccgtcc tagaaagaaa atagatagg gggtttgtgt cttaacgaat cacacgtaga     3780
gatattgata acacacatag ggttaatggt atttcataac taattgattg agcagcagct    3840
cgtagaccac ctaaaaagga atatttatta tttgagccat atcctgacat aagaagaccg    3900 acggggcaa tacttgaaat agcaagccat aaaaaaacac cgatactgag atcggctaga     3960
acaaggtgat aaccaaaagg aattactaaa taacttagta aaattgatat gactgctatg    4020
ggtggtccga tactgaataa acgagtatct cctctagatg gaagaagatt ctctttgaaa    4080
agtaattttg tcccatctgc tagagcttga agaattccca aaggtccggc gtattcaggg    4140
ccaatacgtt gttgtatccc tgcagatatt tctctttcta accagacaat tactagtaca    4200
cctattgtga ttcctaatag aggagtaaaa atagggacaa gcatccatat gatcccatag    4260
atctctttta aggattccaa tctagaaaaa gaattgatag cttgtacttc tgttgtatca    4320
attatcattt taacgatcaa cttctcccat aatgatatct atactaccta gtatcgtcat    4380
aatatcggcc aatttcattc tttaactaa ctgaggaaga atttgcaaat tgataaaacc     4440
gggtgggcga attttccatc gccaaggaaa aacactctta tctcctatca gaaaaattcc    4500
caattctcct tttggcgctt cgactctgac ataaagttct tgcttcgaca attcaaaagt    4560
cggagaaggt ttttactaa tgaatcgata gtcaaaatca ttccatccgg gatcccttac     4620
tctatcaaag cgtcggattt ctaaattctc atagggcccc cccggaattc cttctagagc    4680
ctgttgaata atttttatag attctgtcat ttcaccgatt cgtactaaat aacgagctaa    4740
tgaatccccc tcttttttgcc attggacttc ccaatcgaat tcgtcgtaac actcataagg   4800 atcaactta cgaagatccc attgtattcc ggaagctcgt agcattggtc ccgacaaacc     4860
ccaatttatt gcttcctcgt cgccaataat gcctactccc tcaacccgtt ctaaaaaaat    4920
aggattccgt gtaataagct tttgatattc agaaatcgct gttaaaaaat aatcgcaaaa    4980
atccaaacat ttatctatcc aaccataagg taaatcagca gcgactcctc cgatacgaaa    5040
aaaattatgc atcattcgca taccggtggc agcttcgaat aggtcatata tcaattctct    5100
ttctcgaaaa atatagaaga aggggtctg tgcgccaata tctgccataa aagggccaag     5160
ccataacaaa tgtgaagcta tacgacttaa ctccaacata ataactctga tatagctggc    5220
ccttttaggt acttgaatat tgcctaactg ttctggtgca tttacagtta ttgcttctgt    5280
gaacatagta gctaaataat cccaacgtgt tacataaggc aaatattgta taattgttcg    5340
gttttctgca attttttcca tccctctgtg taaataaccc aatattggtt cacagtcaat    5400
aacatcttca ccatctagag taacaatgag tcgaagaaca ccatgcattg atgggtggtg    5460
```

```
aggtcccata ttgactatca tgaggtcttt tcttgtagct ggtacagtca taggttttt    5520 cctgattcat tcttccatga attgctgaaa gcgaaaagaa gttcatcaaa atttaagcga    5580
atcaaattca aaatgactct tcaaattaac gagttttttt ctccaactgg tcgattaatt    5640
ctttgaattc tttataatgt actctagttt ttttgttctc caaccggtcg attaattctt    5700
tgagttcttt ataatctact ctagtttttt ttgacaaata agccagcagc cgttgacgtt    5760
ttcccagaat tttaagcaga cctctctgag ataaatagtc ttttttgtgc aatttcaaat    5820
gtgaagtaag tctctgtatc ttattggtga aactgactac ttgaaattca acagaccctc    5880 tgttttttt gttttcctct tgcgaaataa ttgaaatgaa tgcatttttt accataaaag    5940 aattttccc tcccctttt acagatatga attttatcga tcagtaataa taataatgcc    6000
agaaatttga gtctagtata cacaaaaatc ggaattctg gcattattat tactgatttt    6060
atcaattaag caattttgaa tttgattcgg atagtgattc aaaaggatgg tacatttta    6120 cactcacaaa agcgaatagt ttttagtac gaagattctg ttgatttctt tctagatcta    6180
attaatatgt cattcactta gtatcgcagt atcctatgat ggaagccagg gcatatgtgc    6240
atctggttgc ttgcatataa catctatggt acagactatg tattatagga aaatgtacc    6300 atgaccgaat ttttaatcgt ggatacatat atatccttaa catactgaaa cggctgccat    6360
tattggtatc aaaccaatag cgattcatac aagctaaatc ttctaatcga taattaggcc    6420
aaagaaagag ctttagttta atcaattcat ttttatctct agcaaggtgt ttactttcat    6480
ccaaaaattg accccagctt tttatgctgt tctccttgca aaatactgga tttatatcca    6540
caccattcct aaaattgaaa tttaaagaat tgagaattct caattctcta cgacgtctag    6600
acgataaaat catttcagga acaagcaaat caaaattatc cttatcaaca gattttggt    6660 ttccgtatct ttgattagtt tgttgcttac tcttatgaac caatgaaata cctatggctt    6720
gatacataat caattcttcc tgatttgtta tatacaggtt ggagtggtgg ctgaaaagca    6780
ttatcccctg cttccaccat tcttttaaaag ccacacccgg ataatccgag gctactaggt    6840
tcgccggccc cagattgccc attgaaacat agagcaaagc cagtcttctt tttcttgccg    6900
cattttttat gtttttccac atagaataga acttgatagg tttctgcatc gtcggcaccg    6960
tccgaggctc aaggtcctct tcgaaaatcg gatacatgag ctcagacgaa atcaaagcca    7020
ctctcggctt cgagcgacgc cggtattttt tttcttttt caggaaccgt ttttcataat    7080
gttctgtcat aacttcttcg atgtttttac taacattttt tgttcctgtc ctaacatttt    7140
ctttaacaat gtctttttct ttcctaacaa tttctttttcc tttcctaaca ttttctttaa    7200
caatgtcttt ttctttccta acaatttctt ttgctttact aagaagttct ttttctttcc    7260
taacaatttc ttttccttc ctaacatttt ctttccttt cctaacaagt tttttgctt    7320 gacgaacaag ttcttcttct atcctaacaa tgagtttttc tttcctaaca atttcgtttg    7380
ctttactaac aagttcgttt tgttcctac caagttcttt tacttgacta acaagttctt    7440
ttgctttcct ataagaaaca ttttcttctt ctttactaac agttcttttt tttttactaa    7500
caagttcttc ttcttcacta acaatttctt ttcctttgaa atctgaaaga agtaatttga    7560
ttggtctaac ccacgggttc attttatatg tctccagagg tagcataact tctcggacga    7620
accaatcttt ctcagtgggg ttagtgaaga gttcttcatt cattcccatc caatcaaaaa    7680
agcttttttt gtgttttttg tgattgagct cttggattc tggatccgaa gaaagactat    7740
cataaataag acctctattc tcaattattt gagaattatt agtcccaacc ttcgtatttg    7800
```

```
tattatggtt aggatcgatc ttcatccagg cctcagcctc aaatttgaga atcttacaat    7860
caaaatctaa agattttcta tttacgccct ggtctagata attcttgtct agataatgtt    7920
tgataaaaat ctcctctggt atatcaaata atttgtcttt ctgtgtggtg taattataag    7980
aaatctcttc tttcttattt acttgtaatg gcaattata aatagaggag tccttcttag    8040
tttcagaaca aagaaattta tatgctaaaa gatcatatct atagtttttt tccaacttat    8100
ttttttgatt tgttaatgaa tatacttcag aatcattttg ttttttgtaa tgaagtaatt    8160
ggtcttttc atatgaatct cctttattta aatctttatt ttgaggcgta tggcgttggt    8220
tgactccatt tcgccatttt tgtggcatta atagagacca tctaatctga gagaaattgt    8280
attgataatg acctcttaac cagttttttcc atggattcgt tccaaaattt cgaagtttct    8340
tatgctttaa ttcggaatga aatattcctt ggctttcaaa agaatccttt attgcactct    8400
taacaaaaaa agatgttccg cgatatttaa gaacagatct taacttatca ctaacttggg    8460
tttgtgataa tttgtaaaat acatatgctt gtgacaggga agataaatct ggtaaggaag    8520
aaacaatttt aagaaaaaga ggtgacgccc ctctaaaggt aattcttttt tcatttgttt    8580
cattaatttt ttttatgaaa ttgattctac aaatattaat gatcctacaa atattaatga    8640
tccatagaaa gatatctagg tatattttgt atatttttc aatgaacaat ttttgaaaat    8700
aatgcaattt acttattaat cgaacttttc ttcttttac aattgtccta atatttttg    8760
gtgattctac attttttttt tcttttgtaa ttatttctat tttcttttg attgtgcttg    8820
ttttattaat caaattttg atttttttctt ctgaatttgt caaagctgta gatcgaattt    8880
gactaaatga ttcatgaatt atctcattgc tgattataga atcttttttct tttttagttt    8940
cactcgattc atatactcct ctcaatatta tattttcttt tattttttg aaaagttctt    9000
ctatttttct ttttagaact agaaccgttt tgataagcca ttttatgctt tcttttgagc    9060
cttttagagc tcgaacaatt ttctttttga ttgttttctt gaacttcttc agaaattttc    9120
ttataactgt aaaatcggtc ttttttcattt tttttttttcc gaataatttt tcacgtatac    9180
tatttagttc ttttaaaatg ggcctccaaa aaaggtcaaa ggaagggtcg tatcggatct    9240
caccatagg atggtcagat agtccccaga aagcccttat aaaagcagaa tcggtattgt    9300
ccacgcttct atcagcctct gtgcgccaag gtttcaaata aaaaataccg ctaattttga    9360
cctgaagacc ttcttcgacc caattctccg gaaataattc tccggaggt agagtagcac    9420
cgtcctgggt gcatctaaaa tgcttctctc tcttccagtc ctcgaaatcc tcagaccact    9480
cggtcttttg caataataag aaacggacaa tagttttagc tattatcact gaaggcaatg    9540
caatatattt tctaaacaat gagttaaaaa atattataca agctcttact ccgagcgcat    9600
attctatcat atcatcccat tcttccattg cccgccactg tagaaaatgg tgttcgaagt    9660
cttgcatgtt gctgacttgt gtttttcttt ctttcctgcc tttcctttct ttcctgcctt    9720
tcctgccttt cctgcctttc ctgcctttcc tgccttcct ttcttcctg cctttccttt    9780
ctttcctgcc tttcctgcct ttcctgcctt tcctgccttt cctgcctttc ctgcctttcc    9840
tgcctttcct gcctttc                                                    9857
```

<210> SEQ ID NO 14
<211> LENGTH: 1872
<212> TYPE: DNA
<213> ORGANISM: Artificial Sequence
<220> FEATURE:
<223> OTHER INFORMATION: Unigene25048_All

<400> SEQUENCE: 14

```
aaaaaaaaag tcaaaaataa gaattaggtt gcgccatata tatgaaagag tatataataa      60
tactgtattt ggccaatcaa ataccatggt ctaataatca agtattctga ttagttgata     120
atattactaa atattatgaa atatttgtag tagttgggaa ttttgtgaaa gattcctgta     180
aaaagtttca ttaacgccta attaatgtcg agtagacctt ggtgttgtga gaattattaa     240
ttcatgcgtt gtagggaggg gtttatgtca ccacaaacag agacgaaagc aaatgttgga     300
ttcaaggctg gtgttaaaga ttataaatta acttattata ctcctgacta tgaaaccaaa     360
gatactgata ttttggcagc attccgcgta actcctcaac ccggagttcc ccccgaagaa     420
gccggggccg cagtagctgc cgaatcttct actggtacgt ggacaactgt gtggactgat     480
ggacttacga gccttgatcg ttacaaaggg cgatgctatc acatcgaacc cgttgccgga     540
gaggaaaatc aatatattgc ttatgtagct tacccattag acctttttga agaaggttct     600
gttactaaca tgtttacttc cattgtgggt aatgtgtttg gatttaaagc actgcgtgct     660
ctacgtctgg aagatttgcg aattccgact gcgtatgtga aaactttcca aggcccgcct     720
catggcatcc aagttgaaag agataaattg aacaagtatg gtcgtcccct gttgggatgt     780
acgattaaac ccaaattggg gttatccgct aaaaactacg gtagagcagt ttatgaatgt     840
cttcgcggcg gccttgattt taccaaagat gatgagaacg tgaactccca accatttatg     900
cgttggagag atcgtttctt attttgtgcc gaagcacttt ataaagcaca ggctgaaaca     960
ggtgaaatca agggcattac ttgaatgct actgcgggta catccgaaga aatgatgaaa    1020
agggctgtat ttgccagaga attaggagtt cctattgtaa tgcatgacta cctaacagga    1080
ggattcactg caaatactag cttggctcat tattgccgag ataatggcct acttctgcac    1140
atccaccgcg caatgcatgc agttattgat agacagaaga atcatggtat acactttcgt    1200
gtactagcta aagccttacg tatgtctggt ggagatcata ttcactccgg taccgtagta    1260
ggtaaacttg aaggggaaag agagatcact ttaggctttg ttgatttact acgtgatgat    1320
tttattgaaa aagatcgaag tcgcggtatt tatttcactc aagattgggt ctctctacca    1380
ggtgttttgc ccgtggcttc aggcggtatt cacgtttggc atatgcctgc tctgaccgag    1440
atctttgggg atgattccgt actacagttt ggtggaggaa ctttaggaca tccttgggga    1500
aatgcacccg gtgccgtagc taatcgagta gctctagaag catgtgtaca agcccgtaat    1560
gaggggcgtg atcttgctcg tgagggtaat gaaattatcc gtaaggctgg tgtatggagt    1620
cctgagctat tttccgcgtg tgaggtgtgg aaagagatca agtttgagtt tgccgcaatg    1680
gatactttat aacactccgg tgcatttcca cccgataaat aaccttcggt atcttaagtg    1740
aattgaaact cggcccaatc ttttaataaa aggattgagc cggtcctatt gtatctatt    1800 tctattcaaa taaatatac acattttcta tagataaggt atcgaacttt tgactcccag    1860
gacaaaaaaa cg                                                        1872
```

<210> SEQ ID NO 15  
<211> LENGTH: 303  
<212> TYPE: DNA  
<213> ORGANISM: Artificial Sequence  
<220> FEATURE:  
<223> OTHER INFORMATION: Unigene1329_All

<400> SEQUENCE: 15

```
gggaaattct catcttagta ggagccttcc aaagaaatag cttagtagcc acattagcag      60
cccttggcat gattttaggg gcggcctatt cccttggct atataatcgt gtggtttctg     120
```

```
ggaatttaaa agcagatttc ctccacaaat tctccgatct aaatggtaga gaagttttca    180
tatttatacc ctttcttctt ggagttcttt ggatgggcct ttaccccaaa gtcttcctgg    240
actgcatgca tacatccgta agtaacttag tgcaacatgg gaaatttcat tgagaggaat    300
cag                                                                 303
```

<210> SEQ ID NO 16
<211> LENGTH: 638
<212> TYPE: DNA
<213> ORGANISM: Artificial Sequence
<220> FEATURE:
<223> OTHER INFORMATION: Unigene1330_All

<400> SEQUENCE: 16

```
ggggggggag agattataca atactcctat ctcaaaacga ttattactcc cttcatcctg     60
gataaatatt tttattttct atttgaaatg tctcaattaa tgttcctaaa gacttttgat    120
gtacaaattc tctaattctt ctaaatatac ccctaaagtt tcatttaata tcaacatagc    180
acattctaga gaagggagta atatttgata ttacagccca tttttaatta tgttttataa    240
ttcttgtgtt ttgtcaacca aaaacaatta tccgaaacgg aagaagtaat aaaaatgaat    300
acttatttac taactatgaa caaaaataga cattaattaa ttaataacaa agggagtaat    360
atttgtcttt ttcttttctt attttttttct tgagatgctt cacttgtaaa aaaaaattgt    420
tttaaaactt aaaagtgaat tcaaacaaaa taaaactagt aaagttggag tacttatttt    480
tggagaaaat gtttgatgcc tcaaatgctc atatttgtgt aaaacaactt attagactac    540
aaatatccat tcgaaaaata tactcttact ttctttttg tatatcgcgc acaatagtct    600
catttcaaaa aattaaacta caaatatcct ttttttt                            638
```

<210> SEQ ID NO 17
<211> LENGTH: 1259
<212> TYPE: DNA
<213> ORGANISM: Artificial Sequence
<220> FEATURE:
<223> OTHER INFORMATION: Unigene17427_All

<400> SEQUENCE: 17

```
gttctatact tgatcagata gttctcgacg caccgcagat aatctcccttt cctgggggg     60 taaaattcaa cccgaagaag ttgttaaccg agttcatagt ttgggctcct agaatatggt    120
ccccttgggg ctttctactt gattggatcg aaagggccaa tgacaatgca gtgggatttc    180
cctattggta cagtgtagtt ttggccgagg agatccagtt cgctcttttt aactatgaca    240
tctatcgcct tgcacagaat gttccggatt ttgattttga tttgttttat aaagatgaag    300
atgaagatga aggtgaaagt gaagatccag agtattcttg tcctagtgaa gagaatttta    360
aaaagaagga gaagcctctg tattataaga ttgaaaatac agatgacgat ggctttgaac    420 cttttttcata tgacccctgg ttggaccaga ggaaagctga tgagtttaac gaggcgttct    480
tgcgggttgt ataccacgca cgagagaaac ttagatctgc caaagaacaa gcctttttc    540 gactgggccg attcatttgg gatcctggaa atccactctg tgtcctattc gacgatccgg    600
cccttgcctc tatgttttca catcgagaat tctttgcaaa tgcagatgaa gagaagtggt    660
atgttactat tgaaataaaa tctatgacta aaagctggct tttcgctgag acgcaagaaa    720
agaggttcga gagttgctt catcgccgga gatggcttat aagagccaag agttcattat    780
ctaaatctaa tgaatcgttc cgttcgaata ctctatccga gagttatcag tatttatcaa    840
atctgttcct atctaacgga acactagtgg atcaaatgca aaagacattg gtgagaaaaa    900
```

```
gatggctttt cccggatgac atacaaaaat ttttcaggga acaatatgct actgctgaaa      960
cacggaagaa ttgaaatctt agatcaaaac actatgtatg gatggtatga actgcctaaa     1020
caagaattct tgaacagcga acaaccagtt cagatattca cgcccgagaa gtactggatt     1080
ctctttcgga taggccctga aaggcgaagg aaggctgtaa tgccaacagg cgtatattat     1140
tgaattcccc cgactcgaca gtacccattt ttggaacgtc cagtgccaaa gtcactgaat     1200
aggtaagtcg ccaatcccga aaacggacta tgtaatgtac tttatctgct gggttacgg     1259
```

<210> SEQ ID NO 18
<211> LENGTH: 2724
<212> TYPE: DNA
<213> ORGANISM: Artificial Sequence
<220> FEATURE:
<223> OTHER INFORMATION: CL10003.Contig1_All

<400> SEQUENCE: 18

```
gaagttcttt ttctttccta acaatttctt ttgctttact aagaagttct ttttctttcc       60
taacaatttc ttttgcttta ctaagaagtt cttttttctt tcctaacaat tcttttgctt      120
tactaagaag ttcttttttct ttcctaacat tttcttcgtc ttgactaaga tttttctttc     180
ctttcctaac aagttttttt gcttgacgaa caagttcttc ttctatccta acaatgagtt      240
tttctttcct aacaatttcg tttgctttac taacaagttc gttttgtttc ctaccaagtt      300
cttttacttg actaacaagt tcttttgctt tcctataaga aacattttct tcttctttac      360
taacagttct ttttttttt actaacaagt tcttcttctt cactaacaat ttcttttcct       420
ttgaaatctg aaagaagtaa tttgattggt ctaacccacg ggttcatttt atatgtctcc      480
agaggtagca taacttctcg gacgaaccaa tctttctcag tggggttagt gaagagttct      540
tcattcattc ccatccaatc aaaaaagctt tttttgtgtt tttttgtgat gagctcttgg      600
atttctggat ccgaagaaag actatcataa ataagacctc tattctcaat tatttgagaa      660
ttattagtcc caaccttcgt atttgtatta tggttaggat cgatcttcat ccaggcctca      720
gcctcaaatt tgagaatctt acaatcaaaa tctaaagatt ttctatttac gccctggtct      780
agataattct tgtctagata atgtttgata aaaatctcct ctggtatatc aaataaatttg     840 tctttctgtg tggtgtaatt ataagaaatc tcttctttct tatttacttg taatggcaat      900
ttataaatag aggagtcctt cttagtttca gaacaaagaa atttatatgc taaaagatca      960
tatctatagt ttttttccaa cttattttt tgatttgtta atgaatatac ttcagaatca     1020
ttttgttttt tgtaatgaag taattggtct ttttcatatg aatctccttt atttaaatct     1080
ttattttgag gcgtatggcg ttggttgact ccatttcgcc attttgtgg cattaataga     1140 gaccatctaa tctgagagaa attgtattga taatgacctc ttaaccagtt tttccatgga     1200
ttcgttccaa aatttcgaag tttcttatgc tttaattcgg aatgaaatat tccttggctt     1260 tcaaagaat cctttattgc actcttaaca aaaaagatg ttccgcgata tttaagaaca      1320
gatcttaact tatcactaac ttgggtttgt gataatttgt aaaatacata tgcttgtgac     1380
agggaagata aatctggtaa ggaagaaaac aatttaagaa aaagaggtga cgcccctcta     1440
aaggtaattc ttttttcatt tgtttcatta attttttta tgaaattgat ctacaaata      1500 ttaatgatcc tacaaatatt aatgatccat agaaagatat ctaggtatat tttgtatatt     1560
ttttcaatga acaattttg aaaataatgc aatttactta ttaatcgaac ttttcttctt     1620
tttacaattg tcctaatatt ttttggtgat tctacatttt tttttctttt tgtaattatt     1680
```

```
tctattttct ttttgattgt gcttgtttta ttaatcaaat ttttgatttt ttcttctgaa    1740
tttgtcaaag ctgtagatcg aatttgacta aatgattcat gaattatctc attgctgatt    1800
atagaatctt tttctttttt agtttcactc gattcatata ctcctctcaa tattatattt    1860
tcttttattt ttttgaaaag ttcttctatt tttcttttta gaactagaac cgttttgata    1920
agccatttta tgctttcttt tgagcctttt agagctcgaa caattttctt tttgattgtt    1980
ttcttgaact tcttcagaaa ttttcttata actgtaaaat cggtctttt cattttttt     2040 tttccgaata attttcacg tatactattt agttctttta aaatgggcct ccaaaaaagg     2100
tcaaaggaag ggtcgtatcg gatctcaccc ataggatggt cagatagtcc ccagaaagcc    2160
cttataaaag cagaatcggt attgtccacg cttctatcag cctctgtgcg ccaaggtttc    2220
aaataaaaaa taccgctaat tttgacctga agaccttctt cgacccaatt ctccggaaat    2280
aattctccgg gaggtagagt agcaccgtcc tgggtgcatc taaaatgctt ctctctcttc    2340
cagtcctcga atcctcaga ccactcggtc ttttgcaata ataagaaacg gacaatagtt     2400
ttagctatta tcactgaagg caatgcaata tattttctaa acaatgagtt aaaaaatatt    2460
atacaagctc ttactccgag cgcatattct atcatatcat cccattcttc cattgcccgc    2520
cactgtagaa aatggtgttc gaagtcttgc atgttgctga cttgtgtttt cctttctttc    2580 ctgccttttcc tttctttcct gcctttcctg ccttcctgc cttcctgcc tttcctgcct    2640 ttcctgcctt tcctgccttt cctgccttc ctgccttttcc tgccttttcct gccttttcctg    2700 cctttcctgc ctttcctgcc tttc                                          2724
```

<210> SEQ ID NO 19
<211> LENGTH: 1331
<212> TYPE: DNA
<213> ORGANISM: Artificial Sequence
<220> FEATURE:
<223> OTHER INFORMATION: Unigene90772_All

<400> SEQUENCE: 19

```
acgggttctt aaaaagtgta gcatgcctga atctaaccgg gttttgcggt ggtgtaggaa      60
ctggatcgga aaaagaggt attctagcga attgaaagga tcttctgatc aatccataga     120
agattttgat tccattcgga atgaggattc agaatatcac acatggatca atcacagaga    180
gattcaacaa ctaaagaaa gatcgattct ttgggatcct tcctttctgc aaacggaagg     240
agcagagata gaatcaaacc gattgccgaa acgcccttct gaagattcct caatgtcccg    300
gctattcacg gaacgtgaga agcagataat taatcatctg tttccggaag aaatcgaaga    360
atttcttggg aatcctacaa gatccgttcc ttctttttc tctgacgggt ggtcagaact    420
tcatctgggc tcgaatccga ctgagaggtc cactagagat cataaattgt tgaagaaaga    480
acaagatctt tcttttgtca ggcgagcgga aaataaagaa atggttaatc tattcaagat    540
aattctctat ttacaaaata ccgtctcaat tcatcctatt tcatcagatc cgggatgtga    600
ctcagaagag agatttcaag aaatggcaga tttattcact ctatcaataa ctgagccgga    660
tctggtatat cataagggat ttgccttttc tattgattcc tacggattgg atcaaaaaca    720
attcttgaat gaggtacaga actccaggga tgaatggaaa aataaatctt tattggttct    780
acctcctatt ttttatgaag agaatgaatc tttttatcga aggatcagaa aaaatgggt     840 cccgatctcc tgcggaatg attttggaaga gccaaaacca aaaatagtgc tatttgctag     900
caacaagata atggaggcag tcaatcaata tagattgatc cgaaatctga ttcaactcca    960
atatagtacc tataggtaca taagaaatgt attgaatcga ttcttttta tgaatagatc    1020
```

```
cgatcgcaac ttcgaatatg gaattcaaag ggatcaaata ggaaaggata ctctgaatca   1080
tagaactcta atgaaatata cgatcaacca acatttatcg aatttgaaaa agagtcagaa   1140
gagatggttc aatcctctta ttcttattta tcgaagcgag agatccatga atcgggatcc   1200
tgatgcatat agatacaaat ggtccacttg gatcaagaat ttccaggaac atttcgtttc   1260
tgagcagaag agccgttttc cagttattga atcttcgatg ggttggtttg agattatcgc   1320
cgagttgtct a                                                        1331
```

<210> SEQ ID NO 20
<211> LENGTH: 1939
<212> TYPE: DNA
<213> ORGANISM: Artificial Sequence
<220> FEATURE:
<223> OTHER INFORMATION: Unigene201_All

<400> SEQUENCE: 20

```
aatgtaatta agatagttct cgaatcaaat catattataa atgagttctt aacatgtgca     60
tttaagatac gtattagctt ttatcaaaat gagttggaat tatcgatctt aaaagcacac    120
ttaatattgc aatctatagt aaatttaaaa aaaacaacaa ccaactcaaa caactagtct    180
ttaatctcca aacgtggcaa taaaattctt aagcactaaa agatcgactt gaatgggttc    240
ccggcccagc ctatggctat tggctaggca gtgtaagcac ttggaagcag ccttggagta    300
acactggccg aaagaggcac agccttttgc aatgcgatcc caaagctctc ttccatgtca    360
actgcaacga ctccgtcagg taatttccaa tcaaatgagt gaaccaatgt acccaaaatg    420
tactcaacca ttccgattcc cattctagcc ccggcacaaa tcctccgtcc ggccccgaaa    480
ggaatcagct cgaaattatt tcctcgagga tcaatgttcg catactttcc actcaaaaat    540
ctttcggggg tgaaatccaa cgggttttcc cacacgttag ggtctctccc gattgcccat    600
atgttgacaa taagtctagt gttttgggt acgtaaaaac cgtctacttg acatgcttcg     660
cttgaaaccc gagggagatt taagggtgta aagggtgtt ttctgaatgt ttctttgcat    720
atggccttta agtaaggcag tttcggtatg tcggattctt cgagtcttcg gtttctgccg    780
ataacttgat ccatttcttc ttgtgcccga ttcaggatgc gtgggttgtt caacatctca    840
gttagtgccc attcaatgat gcttgatgat gtatcagtcc ccgccgtgaa taaatccagg    900
agaagtgcct taatgttgat gatactaagc tggctttccc cggagttttc tcggttagcc    960
gccataagta tgtcaagaaa atcaggattg cccctacgct cgtgagccga ttcagtatgt   1020
tctgtaatca tccgcataag caactcatca aacttctttt gtataatctt catgccacgc   1080
cggatgcctt gcaagtccat ccatgctatt gatggtataa aatcacctat attgaacaaa   1140
ccggccatag tcatgagctc cacaaccatg tggtgaaatt cactagcaga ctccaagatg   1200
gacgaggacg atgaggagga atctaatttg ctggtaacaa tattaaatgc gcgcctacta   1260
agtatcactc gtcctatcat gttggctatg gcataagtta acatctccgg caccaccacc   1320
ggcttattat aaccttttga tccactcgag cactcgcaca tagcttgaag catgtgacca   1380
acctcgactg tccgcacatg agcccaatcc tcaagagcct ttgctccaag catgtgcaag   1440
ttacacagct ttcgcaaaag cttccacttt gggccatagt ctgaaaaagc caagtcttgc   1500
gcgttgtacg ccaagtaggt tggtccggcg tcgattggac ggttactgaa attggcatcg   1560
agggttttca agaatgctcg agctgcttct gggttcgagg ccacgaccat gcccacttga   1620
cccagtttta gatacattat cggcccgtat tttcttgcca tgttcgccaa ggcaacatgt   1680
```

| | |
|---|---:|
| ggcatggtac ctaattgagg aagcgcgccg atgatcggcc atcctcttgg gccaggaggg | 1740 |
| agttggccgg gatgagaggg ttttgcaaag gggatcagaa agcggatgaa gaagtgggtt | 1800 |
| agcaaataga ttaaaattgc tgcactaagt tctcggaaga taataattgt gtctatagcc | 1860 |
| atagcttagc ttgttgaatt aaaagaggat catagaggct ctataaaggc tcaaggaata | 1920 |
| atgctagaac cataaaatt | 1939 |

<210> SEQ ID NO 21
<211> LENGTH: 7183
<212> TYPE: DNA
<213> ORGANISM: Artificial Sequence
<220> FEATURE:
<223> OTHER INFORMATION: CL2802.Contig2_All

<400> SEQUENCE: 21

| | |
|---|---:|
| ggcatacttg ctcaaccgct atcataacaa ttatatgaac aattttttga agttgtcaat | 60 |
| ataattggta ggattagatc cgaagtatac ttcagttttt catgatttca gagaaatttt | 120 |
| ggattcatta ttcatattcc tgactcattc attagattct gcatttatt tgtatatata | 180 |
| aataaatatt atttgaatga gattcatatt aatcttaatc tatattaata aagactaatc | 240 |
| ttattataaa agaaagacaa aaattgcaat aatacgaaag gaagatagaa ttctttcggg | 300 |
| gagtgattgt tctgtcagaa aagaaaaagg ggaaatccca attgttactg aagttacaca | 360 |
| acccagttct tattattcgt ttctaagttg agttgatagg tcctaaaaaa atctgttgat | 420 |
| tgcaagcaca gaatgggtag atgtcgtaga tgatgaacca atttctttt acatgcttgt | 480 |
| tactttcgct tttttagtat tgtctatcta tctataatga tagatgaatc aaaaactttc | 540 |
| aattggtatt tttgtttatc tcctctttt ttgtcaaaat agaaacttag ggaagtgctt | 600 |
| ttttataaac atatgtataa aaagaccata tttcatttag ctcctttatg cttactataa | 660 |
| ctagttattt cggttttcta ttagcggctt taactataac ctcagcttta tatatcgggc | 720 |
| tgagcaaaat acgacttatt tgaaattgat atttgaactg cacaaaactt agacaaagaa | 780 |
| atctttctgc gaaattctgt gtcctctata attacttacc gtatcaattg caaattctta | 840 |
| gtcattgaga ttgatgggaa ttcagattaa tatttaggta tggatattac ctcttttttc | 900 |
| tcctttcaaa gaaattgaaa tgattgaagt ttttctattt ggaatcgtct taggcctaat | 960 |
| tcctattact ttggctggat tatttgtaac tgcatattta caatacaggc gcggcgatca | 1020 |
| gttggacctt tgagtcatta acatcgcgtt ttttgattga cctcctccgt tctttaatat | 1080 |
| tcgggaggtc aaattcagat tgatgttgaa gctatttaaa tctaagaaga acggaatcgc | 1140 |
| gctctgtagg atttgaacct acgacatcgg gttttggaga cccacgttct accgaactga | 1200 |
| actaagagcg ctgtcttatc aaaaaagata agactggaaa gaaggaatt ggattctttt | 1260 |
| tgtaagctca atacatcttt tatgtatata ctagatagta tcataagact gaaagattct | 1320 |
| atacgtccaa tttgaatcga tttcaccgaa tcccccgtta ctgctctagg gaacaggaat | 1380 |
| aggtaggggt agggatgaca ggatttgaac ccgtgacatt ttgtacccaa aacaaacgcg | 1440 |
| ctaccaagct gcgctacatc cctccaatta gcctaagtat cattgtagag aattcctgtc | 1500 |
| ttgttttcca cattgttttt tcttctatag aatatatata tagatctata caatttctct | 1560 |
| gtccatttcg tctttttggt ctcatttaac ctaaaatatt aatcgaaatc gaatcgtaat | 1620 |
| aaaatacttc gatccctatg aaagatggaa cggaacccgt tggaaaatga atgagtatt | 1680 |
| ttggggaagg gctcgggaag aaaaggacgt ttttatgttt tgttttaaga aaaagatttg | 1740 |
| ctgtatcatt gtccagttcc atttgaatta gggattctgt ctactattag agtacaatgc | 1800 |

```
taagtggtcc ttaactacat atgcatctga tcatatatgt ttatgtacta caaaaaatga    1860
aggggggtttt tcaatgcgag atctaaaaac atatctttcc gtggcaccgg tactaagtac   1920
tctatggttt ggctctttag caggtctatt gatagagatt aatcgttttt tcccagatgc    1980
gttgacattc cccttttttt cattctagtt attaacgtgg gaacgcataa agaagattag    2040
agatacaatt aaatatctgt cactaaccaa tctcccccctc tatttctctt ttctctttttt  2100
taaaaaggga ggaaagagaa agaataaaag tggttttaac ggctgtggga ctcggattca    2160
aattcgaatt ctatactact ctaataaata atagaggaat gtaagtagaa tgtaaaatgt    2220
gggtcgaggg aagagtatta tacaagctac ttaaacgaga tactggacta tagtttgaaa    2280
tactgtgatt tgtaatttcg tttataaatc tttatatctt attttaatag agtgattaca    2340
aattttgag aatttgattt caagtgagga acgtctattt ttttctttct tcgtcttcct     2400
ttcgtatcga aaggaaaagg attgagtaaa ttaaaaatcc caaggaggtt catggctaag    2460
ggtaaggata tccgaataac gattattttg gaatgtacta cttgtgttga aaaggttgtt    2520
aataaggtat caacagggat ttccagatat attactcaaa agaaccggca caatacgcct    2580
aatcgattgg aattaagaaa attctgtcca tattgttaca aacatacgat tcacggggag    2640
ataacgaaat agctcgaacc gagcactccc ttgaggagta ggaaaagaa aagtctaatt     2700
atataattag aatgttataa ttaatttaa gctaatttaa atagaaaaca accaaatcct     2760
atttatttt atgtattctc gttttataga tccaaccgaa ataggattct cggtttaaag    2820
gaataaacta aacaaaccat ggctaaatcc aagcaacctt ttcttaaatc caagcagcga    2880
cctttcttta aatctaagca atcttttctt aaatccaagc aatcttttcg taggcgtttg    2940
cccccaatcc aaccggggga tcgaattgat tatcgaaacc tgagtttaat tagtcgattt    3000
attagtgaac aaggaaaaat attatctaga cgagtaaata aattgacctt gaaacaacaa    3060
cgattaatta ctcgtgctat aaaacaagct cgtatttat cttttgttacc ttttgttaat    3120
aatgagacac tatttgaaaa aaacaagccg accgcgagag ctagaaagaa atataagcca    3180
ggcagaaagc caggcagaaa gccagacaga aagaaagaaa agtcgactgt gagagacgaa    3240
aagaaataaa aggcgaacgc gcgagacaaa aaaataggct tacccttttct tcacttgaag   3300
caaaattcac acccgaactc aaaggcagat tgatgctttg ttcgaaaaat ctgacaatcc    3360
ggagttgatt ctcgtgtcat aagacaaaaa caaataaaaa atcaggtacg aagtcaaact    3420
aaaaattttt gattgaatgt gttgattcat atttcttttg cttactttat tttttcatat    3480
tttattcatt ttgaccctcc tttcccggag ttcattctcc ggggaactcc atttaaatta    3540
ctccggcaga ttcctcccaa tttacttctg attttaggat ctcattggaa atcacataaa    3600
gactgttttt atttgctatc gctatttggg caagtatttt acgattaaaa agcaactgtc    3660
tcttgtatag atcgtggatt aatctactat aactatagta tacccagctt tgacgaatta    3720
ctgaatttat tcgagtgatc cacaaactac gaaaatctct cttttgccta ttcctatccc    3780
gatcagacga agacaaagct tttatttctt gttgagtcat agttcgaata agccttgaag    3840
gccctccccg agagtttgat agcgtttttt ttttacgtct ccgagctata tatccccggc    3900
tagttctggt cattgaatat gcaaaaatca aacttttccg aataactaaa tgatttcctt    3960
tctttcagtt attcttttttc ctgtcctagt ctattaataa caaaacggct ttttccaatg   4020
tataaactca aaattccaac ggctttggct actataacct tcccaaccac gattttgct     4080
tttttctagg catttcacct cgaaatccta aattatattc tactgggtat ttaaactcga    4140
```

```
ataagaaata aaaattagaa agaaatagtg gattccatcg tttctctggt tccttcttaa    4200
acggtgaggt cttctctata caccggagcc tttaattttc tttaatcaat gttattgtta    4260
acttgtatag ttcacattct ttggctctac ccatgacttt tccagtaact aggtctttca    4320
caacaagatc tacctataca gtaacggtat ttaattatga gggttggctg ggtagctgac    4380
cctgttagtc cgttcttgca agagggccac ccaatctttc tgttttaaa tttgaatcca    4440
gatttcttcc gcttaatgga taaccatttg ttaccaatgg agaattctta aattgagatg    4500
attggagtta caccaatgga aaccataaat ttcatacaca atgaaaggca tatgatcaat    4560
tttcttagtt ttacatagta aatggagttc attttctat tctatcctat tcaccggtac    4620
tgatctttga tactggaaaa ttgttctctt tcctttgttc tagctcataa tctgaacgag    4680
tcgcacatac aacctagtac acgttcctcg acgttgagga catctcttaa gagcgggggt    4740
ttttgtgaca tttctgattg gctgtcttgt atttcgaata agttgtttaa tagttggcat    4800
gttgaatcaa cataataatg ggatggttta gatcaatcct aaccagatta ctcctattaa    4860
attcggttga tagggctaat ctcaaatcat agatttacac gaactaccag tcaacccccga   4920
tagaatcaat aattccataa gcttgggcct ctgttggtga cataaaagta tctctttcca    4980
tgtctgcagc tataacctct agaggcatgg gcgatctgtt tgcataattg tataggacag    5040
ttctgcgtaa tatctttact tcgtctaggt ccatgtatgc atcctccgcg cgggtcaaag    5100
gctcccggt tatactaact tttggttgat ggatcattac cctagcgtga gggaatgcta     5160
tacgtttggt cagtgctcct ccggacagga tcaaagctgc cattgaagcg gctaatccca    5220
cgcatagtgt atgtacatct gggtctactg cttgactcgt gtcatacaca gctagtccat    5280
tcaccatttt tccaccagta gagtttatga ataaaaattg ctctagggta ttatcgtcga    5340
gattcagata taccataagg ccggtaatgt tattcgtgac ctcctgcgta agttcttgga    5400
atagaaaaag tgttctgatt cgataaagtc ggtcgattag gggaaaatta gattccttag    5460
gaaccgtacg ggcgcctttt gacgcatacg gttccaaaat tttgcgaaaa aaaccaatgt    5520
atagattcca aaccccttt cggatttcat agcatgctct tgcggacgtc taattttct     5580
tcgattttc aataaaaacg agttttatt ccataaactt atcgaattaa cttttcattg      5640
atgtattctt tcgtcgagat cgaatcgaaa tcccgatgtc atttcttgt tcctaaatgg     5700
gcctcttgaa tcttaatctt tttaggttga gactctactc cgggtaaaga tctgcccgct    5760
ttcgatttgc atatatagga caaatactcc cattaccact tctttttct caattcatgc     5820
attcccgcaa atgaggtcat catgcatatt actcgattga ttaagagaac agtttaagat    5880
cacttctatt tacaaatctt atataaggag taatggtaga tatattacca attggttttt    5940
tttaaacgga gcctggatac ttcacttgat taatccaacc aagccaacca taaattattc    6000
gagtggataa tagtaatttg aacccccta caaatggatt taattacact tcacgctcca    6060
aattttgat cattcaaaaa atggcgaaat agaggatctc tcgatcgggg agagaacggg    6120
gaaatcccat atgacccaat atatctgaca agtcgcacta taagtcaagc caagataacct   6180
cttcttcttt gtctatatct tcgtctttat cttcgtcttt gtcattattt ttttaggaa     6240
ttagaaaagg tacttttgga acaccaacag gcattaaacg atagaaaaaa tagtactata    6300
tttactttga tgtggaaacg taacaaggt tttattctta aaaaaaatg aattatcaaa      6360
aattcataaa aaaaggcaga atgaataagg tcaaagtctt agaaatctaa ctagctaata    6420
taacatattt ctttcataat gtaaaccaac tattcatacg tgtatttctt ttttttttt     6480
tttaccccctt tttgctttaa ttccacgcgg taaacatata ccacaagaat tcaaagttac   6540
```

```
tcaagattca tttgattata taccttgatt agaaaaacaa ttatgtcgtc ccgaatcttg    6600
gcgataccct tcggtcaaat atttggtaaa gcgcaaagcg cccctgcgcg acggacttta    6660
gggcgatcct ctcctttata aaaggtatct ctgaagggcc atacaaattc accttggaag    6720
ggagccgaag ctgtcttgtg atcaatttct cgaagtcgcg tcattatgtc gctctcgtta    6780
cttagggcaa ggtccaagaa aaattcgtag agtttcagcg aagtctccag agaccaaacg    6840
aacgcaaccc aaagcggaac ttcgaatcgg ggtgaagtca gacggccccc tctatcagtc    6900
gatcggagac tctctcggca tcatcgtatc ccttttcaat ttcgtctttt aaacagtcta    6960
gacagccgcg ctgccataat tcctatttgg aatcactttc gctatctaag gggccctcta    7020
cccgaatatt ctaaattggc cagattcttt ttgtgtacaa gaatctctta cgaaaattta    7080
atctatctaa aaaatagaaa aggatcatgc tattaagtat tttaatttaa gttctttcta    7140
agaggtggaa tagaataacc cgcttaaagc gtaatgatca tac                     7183

<210> SEQ ID NO 22
<211> LENGTH: 766
<212> TYPE: DNA
<213> ORGANISM: Artificial Sequence
<220> FEATURE:
<223> OTHER INFORMATION: Unigene11152_All

<400> SEQUENCE: 22
ggaattcata ggtataggaa gaagccctat caagaaattt gttctttcga ccatatttct      60
agtgttaaga cgatatattt ggaccgatac tacaaagagt attacaccct tgatcgtgaa     120
attgaaaaat cgagcgattt tccttgttaa agagaaaccc ggcggattgc atatgcgtga     180
aagtaggata ctccaaattc ggggatcaaa agtttttaga aacgttcttt ggtccaaaaa     240
aatgtgaatg aaagatctca ctgaattgaa ttggttccat gcagagtcta gagattgaga     300
attcttgatc tctctcaata tctctctcaa ttctaaaata agaatttgaa ttgtagatt      360 catagtagtt tagttctcct aattattggt tttaaaaaaa ggtttaagtt caattaaact    420
aaccctagta cgaggtaaca taaaaaaagg tttaagttca attaaactaa ccctagtacg     480
aggtaagcat ccatggctga atggttaaag cacccaactc ataattggcg aattcgtagg     540
ttcaattcct actggatgca cgtcaatcgg accgtctcta tatgttttt catataatc      600 atatatgtta gattcatatc ttactaggtt agattcatat cttattatat gtaattcata     660
tatgttagat tcatatctta ctaggttaga ttcatatctt attatatgtt tttcatatat    720
gttagattca tatcttacta ggttagattc atatcttatt atatgt                  766

<210> SEQ ID NO 23
<211> LENGTH: 10328
<212> TYPE: DNA
<213> ORGANISM: Artificial Sequence
<220> FEATURE:
<223> OTHER INFORMATION: CL10780.Contig2_All

<400> SEQUENCE: 23
ttttagtttg taggtccggc ttgggccaag tggattggat taggattatt caaacaactt      60
gtcagaggat tattcgacaa atccgtgggc aagtggagat gcaaatctat cgagtgattt     120
tagtttgtag gtccggcttg ggccaagtgg attggattag gattattcaa acaacttgtc     180
agaggattat tcgacaaatc cgtgggcaag tggagatgca atctatcga gtgatttag      240 tttgtaggtc cggcttgcac cttttacgaa aacaaattca taaagaacc gcaagtcagt      300
```

| | |
|---|---|
| ctgataatgt gcggttttat attgccaacg gttggtttat ggcttccctg ctctcaggaa | 360 |
| gtctagatca tcgaataaag gtagaaaata aaggaatagg tctcaaggaa gtccttgtcc | 420 |
| tccagttgac ccatttcgat gtccgattgt tacggcatat ccgtctttta aaagtatctg | 480 |
| tgtcatctag ggctcgggaa tacatagatg attttttaga agatatcatg tggcaactgc | 540 |
| accaggccat aaaaaaggat ataaaaaatg ttattgctcg gggcgataaa cttgagaatt | 600 |
| gttttcaacc ggcttctccg ataacaggtc atactatgct tttggctttt tgtttatatt | 660 |
| gtcgaggcct aaccgagtcc cagacagaag aggaatgttt atgctttctc caaaaagcat | 720 |
| ttaaagaata ttcatgcgaa ttataaatgt aagaaagatc taattcgtaa gaagaaaaaa | 780 |
| ttttattata gcctttctta ttctagcctt acttaataat aatcggccca acaactatac | 840 |
| atcattacat cactcgctaa tgtgataaat tttaaaaaat ttccaaatct gaggtattcg | 900 |
| tggtaaagct ccgtttaaaa cgttacgggc ggaaacaatg tccaacttat agaattgttg | 960 |
| cgattgatgt tcgatctcga cgaaatgggg ccgagtttgc gaaagtagga atttataacc | 1020 |
| cgcgcagcaa gcaaatttct ttaaacaaat ccgcgattct atattttctt gaaatgggtg | 1080 |
| ccaaacctac aaaaacggtt tttcagattt taagaagtt tggagttttg aagtaattgt | 1140 |
| ccccgcatca aatttcaatt cgaaatattt ttatacttca gtaattttt tatcttattt | 1200 |
| caattgaaat ttgattgttt gccttatatt gacaacaagg aattgaacaa atatactcca | 1260 |
| ttattcaact aataggttcc ttgtctatgc tttgaatgaa taatttttata ttgaaaaagt | 1320 |
| gaataagata agggatgatg ggccccttt gggctttcat cccttatctt agattttttg | 1380 |
| tttttttctt ttctcgtcaa atttattgta ttttcgtctg agttattccg ttttattttc | 1440 |
| ctaatcgatt agaaaatgtg ttttagggt ttgattacct cgtctaatca tttattttga | 1500 |
| ttctgattgt atctacattc ttttattta ttcgggttgc taactcaacg gtagagtact | 1560 |
| cggcttttaa gtgcgactag gatcttttac acatttggat gaagtgatgg attcatccat | 1620 |
| accatcggta aagtttggaa gaccacgact gatcctgaaa gggaatgaat ggaaaaaata | 1680 |
| gcatgtcgta tcaatcaaga gttctgagaa tattttattc ttgccagatc ggtataaaac | 1740 |
| gttcttttacc ttattgaaag atagcaaaat gtattcaatt tcaagttggg tcgaatgaat | 1800 |
| aaatggataa agccctgtgg cttcaattaa tttccttaaa ttataaggaa agaaaaagta | 1860 |
| acgagctccc attcttaatt tgaatgatta cccgatctaa ttagacgtta aaaatatatt | 1920 |
| agtggctgat gcgggaaggg cttttcccct gagcggattc cttattattt aatgaatcct | 1980 |
| aaatattatc attctccatt ccacaatgga gatgtatgtg tataagaaac agtatattga | 2040 |
| tcaaaaaatt tccaaaatca aaagagcgat tgggttgaaa aaataaagga tttctaaaca | 2100 |
| tcttaattat cctagaacga atataaacta cttcaattaa atggaaaacg agaggataga | 2160 |
| gaatctgatg ataagtttac ctgtatccga ggtatctatt cctttcttac tataaaaaat | 2220 |
| accttgtttt gactggattg cactatgtat catttgataa ccctaaaaat cctcgacctt | 2280 |
| tggttcaaat agacttaaaa tggaggaatt tcaaactgct ttagagctcg ctagatttca | 2340 |
| acaacacgac ttcttatatc cacttatctt tcaggagtat atttatgcac ttgctcatga | 2400 |
| tcattgttta aatagatcca ttttgttgaa aaatccaggt tatgacaata aattcagctt | 2460 |
| gctaattgtg aaacggttaa ttactcgaat gtctgaccag aattatttca ttgattctcc | 2520 |
| caatgattct aaacaaaagc cgttttgggg acgcaacaaa aatttggatt ctcaaatgat | 2580 |
| atcagaggga ttttcggtca ttatggaaat tccattttct ctacgattgc tatcttcgct | 2640 |
| agaaaagctc gaaaagaaag ggcatggtat agtaaaattc gataatttac gatcaattca | 2700 |

```
ttcaatatttt tcttttttag aggacaaaat ttcgcattta aattatgtgt tagatatact   2760 ataccttac  ccaatccatc tagaaatctt ggttcaagct cttcgctaca ggctaaaaga   2820
tgcttcctct ttgcatttat taagattctt tctccacgag tttcctaata ggaatagtct   2880
tattacttca aagaaagcgg gtccttcttt ttctgaaaga aatcaaagat tcttttttctt  2940 cctatataac tctcatatat gtgaatacga atccgtcttt gtctttctcc gtaaccaatc   3000
ttctcattta cgatcaacat cttttagagc ccttcttgac cgaatctatt tctatggaaa   3060
aatcgagcat cttggagaag tcttgtccag ggcttttcaa gtcaatctct gggtgttcga   3120 ggattcttc  atgcattatg ttaggtatca aggaaaagca attctcgctt caaaaggtac   3180
gtctcttttg atgaataaat ggaaacatta ctttgtaaat ttttggcaat cttatttta    3240 cctgtggtct caactaaaaa ggatccatat aaaccaatta tccaaccatt cccttgattt   3300
tttgggttat tttcaagtg  tgtggcgaaa gacttcaagg gtacgcaatc aaatgctaga   3360
aaagtcattt ctaagcgata atgctattac aaaatttgat actattcttc caattattcc   3420
cctaattgga tcattagcta aatccaaatt ttgtaataga gcaggtcatc ctattagtaa   3480
ggcggtttgg gtcgatttat cagattctga tattattgac cgcttcgggc gtatatccag   3540
aaatctttct cattattata gtggatcctc aaaaaaaaaa gagtttgtct cgaataaagt   3600
atatacttca actttcttgt gctagaactt tagctcgtaa acacaaaagt actgtaaggg   3660
cttttttgaa aagattcggc tcggaattat tggaagaatt cttttacgacg gaagaagagg  3720 ttctttcctt gacctttccg cgagcttctt ctatttcgcg gaggttatat agaacgaggg   3780 tttggtatt  ggatattagt tctatcaatg atttggctaa tcatgactga ttcgttatga   3840
aagcgtgtaa atgaaaattt tatttagaat gaatttaata aagaaaaata atgaagaact   3900
aacaaaattt ttccgtatt  atattctgaa atgttgatgt agtaaggatt aaatcaactg   3960
agtattccac ttccttctaa taaggagcg  gagttttaaa tatatacata gggaaagccg   4020
tgtgcaatga aaaatgcaag cacggcttgg ggagggattt ttacttattt aaaaaggaaa   4080
ttatctactc catccgacta ggtccgggtt cgaatcccgg gcaacccatt gtgatgtcat   4140
attcaaatta tagtttctgt ctctcaatcc ttttttgcag ctcactacat gaataaaaaa   4200
tttagagata gctagatcta tctagatctc ggtagatatg ggttgacacg ggcatgtaag   4260
tcatattata ctgtttacta acaagccttc gttttgatt  tgaaaattcg cgtgcttggg   4320
agtccctgat gattaaataa accaagattt taccatgact gcaattttag agagacgcga   4380
aagcgagagc ctatggggtc gcttctgtaa ctggataacc agcactgaaa accgccttta   4440
cattggatgg tttggtgttt tgatgatccc taccctattg accgcaactt ctgtatttat   4500
tattgccttc attgctgccc ctccagtaga tattgatggt attcgggaac ctgtttctgg   4560
atctctactt tatggaaaca atattatttc aggtgctatt attcctactt ccgcagctat   4620
aggtttgcac ttttatccaa tatgggaagc ggcatccgtt gatgaatggt tatacaatgg   4680
cggtccttat gaactaattg ttctgcactt cttacttggt gtggcttgtt acatgggtcg   4740
tgagtgggag cttagtttcc gtctgggtat gcgaccttgg attgctgttg catactcagc   4800
tcctgttgca gctgcgactg ctgttttttt gatctatcca attggtcaag gaagttttc   4860 agatggtatg cctctaggaa tttctggtac tttcaacttc atgatcgtat tccaggctga   4920
gcacaatatc cttatgcacc catttcatat gctaggcgta gccggtgtat tcggcggctc   4980
cctattcagt gctatgcatg gttccttggt aacctctagt ttgatcaggg aaactacaga   5040
```

```
aaatgaatct gctaatgaag gttacagatt cggtcaagag gaagagactt ataatattgt    5100
agccgctcat ggttattttg gccgattgat tttccaatat gctagtttca ataactcccg    5160
ttctttacat ttcttcctag ctgcttggcc tgtagtaggt atctggttca ctgctttagg    5220
tatcagcact atggctttca acctaaatgg tttcaatttc aatcaatctg tagttgatag    5280
tcaaggccgt gtaattaata cttgggctga tattattaac cgggctaatc ttggtatgga    5340
agttatgcat gaacgtaatg ctcataactt ccctctagac ctagctgcta tcgaagcccc    5400
ggctaaaaat ggctaagatc gtggtctgaa tgtatatgag ttttttgaagc aaaaggagca    5460 ataaccccttt tcttgttcta tcaagagggc gttattggtc tccccggccc cccttatttt    5520
tcttttagtg agtaatattt cacttctacg gaaaagggat tttgggggt tggtttgagt    5580 atcgtgcttt actttcatat ttatttctgt attttttttt gttttttttt ttgaatctat    5640
aatatttgaa tttatatatt tataccctct tctcaatttc ttgtgaagtt attattttca    5700
atgtacaata accgaaagtt tgaatagaat tttatgttta ttatatggaa acatactag    5760 aggggcggat gtagccaagt ggacaaggca gtggattgtg aatccaccat cgcgggttc    5820 aattcccgtc gttcgcccaa gtcaagtttg aatattgggc cctttcccga gtctgattat    5880
ccttgtcttt gtttatgtct tgggttggaa caaattacta tcattcggcc ctgtcggcgt    5940
attaatcgac attttcaca cattttacga acagaggctc ttattttcat atttgccgac    6000
ccttaacttt aattctgaat ctacttttg gaagaaaata attttcttga aattttgcat    6060
ctcgaatcct agtgaatatt gaagttgaaa aaataccgaa ttttttgaat cttgtttttc    6120
gcaaagtcga taaattatac gtcctttcgt ttcatccaac caaaataact tcgaattcaa    6180
gtaaaaattt tattgcatca tcaaaactac ttaaatatct cttttttact ttctattgag    6240
agagcctttg taaatccata caactttcgt tcttacctttt ctttgttccg acccattctt    6300
tgaattcttc catctttttta ttgatttgat ccctttattc aactcagagt aagagattcc    6360
aacaaaagga cttctgttgg aatctccgca taaattgtca aattagatag attttttaacc    6420 tatactagat aatataacat atacatgtct aaaccaacta taagaattca aagtgactca    6480
agatccgttt gcttcaatac ttttattaca aaagggagta ttgcctcctg aacctcttcc    6540
ttttccaccc ccccacgttc gatgactgtt ttattaaaac ctaaagactg cgccttagtg    6600
ataatcggac agtcgtaccc tcgacatgcg cgttcgctat gtctaaaggg gcagataaat    6660
tcaccggatg gaggcggaac cttcttctga tccacttcgc caactgtctt cattatcgag    6720
ttttcggttt ttagataaac ccctgataca aatgtggagt attcctcgga gatctcgttg    6780
acccaacggg tcgcagacga gaccggaatg tcgaatcgag agttttcaaa ctcagatttt    6840
tgtatacgcc cacctgtcat ctgttcatag acctcgctgg cattatcgga accctctccg    6900
attttgtctc ttaactgttt gacacaactt cttttccaca attctttctc ttcgttatct    6960
aaagggccgg gcgccccccgt atgacaaatc agcgagattc ttttttgggtc caaaattcta    7020 gttccgaaag tgaaaaaact cctaagtttc ataataatat tctcccttat agtgtattta    7080
ttaatatcta gtgttctcca gattatattt cctttatttc aaattgtcaa tagatagata    7140
ggaaaagaga tcttttagat ctctttcctt ttttttttaca actctctact tttcgatagc    7200
gtaatcttgt ttttttattac tcaaaatcgt agctagtgta gttgtagcga ttttttttag    7260 tcaattttttt tgagccatac atagcttgta aaagactatt tagaaaacta tagtcaatgg    7320
tgtccctcca tagattcacc tatataagcc gcggctaaag ttgcaaaaat aagagctaga    7380
ataccaaata atccaagagg gataggaacc actaaaggga ctaaagaaac aagaacatta    7440
```

```
ccatatataa cacaaacttt ctccgccgat cttttctaat cgagcctctc ggtctgtcat   7500
tattcctcga gaagtcgaaa ggattacaat ccccatccca cctaaaattc taggaattcg   7560
ttgatagttc gaatagattc ttagaccggg tcgactgatc cgttttaaat ttaaacttt    7620 tatatttcct ttccaattct ttcgtagagt taaaaccaaa aaggatttat tgttttctcg   7680
atgttttctc acattttcga taaaaccttc tcgtacaagg attttaccaa tactttcacc   7740
gatagtacta aatgctattc gaaccactct ttttctagcc atctcagcat ttcgtataga   7800
ggttagcagg tcagcaatag tatcattccc cataatgaat taaaggtctt aatgcctcta   7860
aattttgatc taatcaacat gtttttcttc tttgtttatg actatgaatt ttgaagggta   7920
aaaaaatatg cctgagacac aatctactaa ctgactctta atctatttct ttcaaatagc   7980
ttactataac catattttgg aactatatta tggtctcgtt ttataatagt tcgggggcta   8040
atgaaattat tttcgtaaaa ttgcactgtc tcaattcctc tgcaatcgca ccaaaaaccc   8100
gacttccttt tggatttccc gcttgatcaa tgacaactgc agcattgtca tcatatcgta   8160
ttatcatacc gtcgtcgcgt ttgagttctt tacaagtacg tacaattaca gctctgacca   8220
cttctgatct ttctagcgac attttttggaa ctgcatcttt gatcacagca acaataacgt   8280
caccaatatg agcatatcga cgattgctgg ctcctatgat gcgaatacac atcaattttc   8340
gagccccgct gttatccgct acatttaaat aggtctgagg ttgaatcata tcattttttga  8400 tttgttcttt aaaatgccaa gtaaagggcg aagaaaaat actgtttgtc caaaaaacga    8460
aacctgcacc tgcgattgtt ttttttatcc acacaactta tttcttttgt caaaattta    8520 tctcgaaaga atgaattgag ttcgtatcgg cattttggac gctgctattg aaatagcctt   8580
tctggctata ttttctgtta ctccgctgat ttcataaagt attcgacctc gtttaacaac   8640
agctacccaa tattcaggat ctcctttacc cgaacccata cgcgtttctg cggctcttac   8700
tgtaaccggt ttatctggaa atatgcgtac ccatatcttt ccaccgcggc gtgcatttcg   8760
tatcattgcc cgccgacctg cttctatttg tcgagatgtg atccaagccg gttcaagtgc   8820
ctgaagagca tatttaccga aactaatatg attcctcga taagagattc ccttcattct    8880
tcctctctgt tgtttacgga atctggttct tttggggtta tagttgatgg ttggctttca   8940
attccatctc tactacagaa ccggacgtga gagtttcttc tcatccggct cctcgcgaat   9000
aaaggtattc aaaaatagtg aattttaatg aacttcagat agaatagagt ttaaattaag   9060
atatacatgt agttaataag tataagaaat acaccgaagt atggatttca tttaatccat   9120
gtttatataa aatattgtat tggttttttag aatgttaaaa tgaatctttc ttttgttttt   9180
tatccttata actgaatcga accgtattct cgtgcccaaa tttagcaatc caagaaaatc   9240 aagtttcgc gggcgaatat ttactctttc cattcaactt ctattcggtt gtagaaatag    9300
ttcataactt tttcaaatag atgaataagt ctctggtccc tttcgccatc cagatcgatg   9360
aatcattaga attcgttttc aatagaattt tttagatcca caggttccgt cgttcccatc   9420
gcttcttact taatggttag gtctgaattc tgcaatggag ctcgtaatga aatttcttct   9480
tgagtcaatc ttcttagtct ttattggctc gaagctctta attttttgt tttgttctat    9540 ggccagattc gttttattat ggatcaatcc ggattggtgc tttctgacac tgcattttt    9600 ttttgagatg cctcatagac cttacatatt acaaatggga attagatatc atcaatcttc   9660
ttttttcttc tttctctcac ccttctagtt atccaaatcc ttattttctt tctttattt    9720 ctcttcacaa cttcgaatca gattttttgt ttttctttat ctcaaaagat ttccgttgct   9780
```

```
acaaggatat gattgatttg tcatatcttg actggttctt tggatccaga taatgcaaag    9840
caatgagttg gttattattt ctatagttta gccctaaaaa accaacgagt cacacactaa    9900
gcatagcaat gatatcaaac gttcaattga attttttatta accccctagag aattaagaag    9960 aattaagaat acaaattttt tatttcagtt tttttgattc aacagaaaaa gaaaaaaatg   10020
actttctcgg tttttattcc atcaccgata tagaagggaa gggctaggtt tattattact   10080
cgtctataaa tatccaaatt tttatgccta ataccccaga gatagtttga aatgaatagg   10140
aacaataatc aattttagct cgaatggttt gtaggggaag ccgacccttt tggatcgatt   10200
caacccgggc aatgtctttt ccgtcaagac gtcctgcaat ttgtactcga attcctttta   10260
tatttgtttt ttcattattt gttttttcat tatttgtttt ttcattattt gttttttcat   10320
tatttgtt                                                           10328

<210> SEQ ID NO 24
<211> LENGTH: 1558
<212> TYPE: DNA
<213> ORGANISM: Artificial Sequence
<220> FEATURE:
<223> OTHER INFORMATION: Unigene51089_All

<400> SEQUENCE: 24
gtttcaatta gcgtttccgt tgacggaaat atgacactgg aaatcgtgca actggtgact     60
ttgatcggaa aattgctatt atgagatcta acaaaaaat gagttttcat tatggtctta    120
cagctggagc gcatattatg ttttctggct tttatttgct gaatagacag attgatcgca    180 aaatcataa ctatacttaa taataaaacg ctttgaaaag cccatacacg gcgaagactt    240
tttgttgccg ccggaaaaag aagaaatccc atccctatta agataggaac tggaagtgga    300
aggaaaggta ttatacatgc atattgatat gtctgttcca taaaaaataa aaaaagttttt    360 ttagtcttaa ttaattactt tcaagtcagc ggatcctacc cctttacaaa ggagtcaata    420
aaaaaagata cacgaactta agaaaaaatt tagcatttta tattcttact tattaagaat    480 cttttttgaaa ttgtttaaat attctgcaat caaaggattc atagcgtaag catgggaatt    540
ccactaaaag tctttgattc taatatgaat catgagatta actaatgtaa tcgacttaat    600
aacccgtcat tttcatttta gttgattcca actaagtttt tataaggttg aacgttagat    660
aaaaggatct agcttgtaac ataacagatt aattactaat ctcattcgaa tttaaacagt    720
ttttttggcg tattctttcc tcaagtttgg ctagttaatc aaagaaagat tcaattttttt    780 atcaagctta agttatctttt ttaactactt caatagattt tattacatgt aaaaaagtat    840
aaaatgctga aaatcaacag gatcggtct tttagattct ttttttttag ttctactaag    900
ttgatttcga tgttacaact gattatagaa atatatgaga agaacgata aataaaaatt    960 tcaaattgtt tgttcttaca aggtttgtaa gacataaaaa actgtgtttg aacaaaactt   1020
ttttagtaat ctttttataaa attttcccat atttatttgt tttgttatga agtgactaag   1080
aaaaaaacta gataactgaa tagtcactaa ccattcgttt tgaagactag atgtttttca   1140
cattcaacta taacaatggg aaacctctta atttcgaaat ggcagtccca aaaaaaacgc   1200
acttctatat caaaaaaacg tattcgtaaa aaaatttgga aagggaaggg ctctaggtcg   1260
gcgttaaaag ctttggcatt aggaaaatct ctttctagcg ggaagtcaaa aagttttgtt   1320
ttgcaaaaaa gcggcttcgt aaaggatttt ggaaaaggaa gggctttaga aagctttggc   1380
atcaggaaaa tatctttcta gcgggaatat ataaacaaat aagtgataaa agattggttg   1440
taatgggagg tttaacaaaa tatgtaccaa ttcgcattct ctcgtatttt ggactactca   1500
```

```
atatgaaata gactatgttt tgtgattatg ttggaaaatt tagaattcta caaattct      1558
```

<210> SEQ ID NO 25
<211> LENGTH: 1321
<212> TYPE: DNA
<213> ORGANISM: Artificial Sequence
<220> FEATURE:
<223> OTHER INFORMATION: CL1361.Contig13_All

<400> SEQUENCE: 25

```
gttatgcaca acaaaggagt tcaccaccaa gctagcttga acatatcat agtatcttac      60
catattacta cgtgaacatt atggaaaaca tacgtcacga atatagggcg acaagtgcat    120
attaattcta tgaacaatat tattacaaat cttaagacat tactaaattt tctctataat    180
taagtgagca ccgaattgtg gttgaagagt gatgacggtg tgaggagcat gcgaatagga    240
tgtcgaaagt gcaaggaga agcgttgtag tatcatagcg agagccattt tagcttccaa     300
catagcaaag ttttgaccaa tgcatatcct aggtcccccg ccaaatggga gaaatgaggc    360
ctgccccttt gttacctttg atactccttc tgaaaatctc tctggtttga attcattaga    420
atcatcaccc cacaattcac aatcacggtg caccatcatt ataggcactt ggataaacac    480
tcctgcgggt agagtactat cccctacctt catttcttca aggatcaacc gcctaagtag    540
aacagctggc gggtacaacc tgagaacctc gttcaaaatc atacttataa ttttttaggcg   600
atttaaccca tcatgatctg gtttttatt cgcaaaaacc tgaaaaactt cttctcttgc     660
ttgttcttgc caaagttgat gctgactcaa taaaaccatt gtccatacca acaagttcga    720
agtcgtctcc tgtcctgcaa agtagaaaag tttgcactcc tcaatgactt cctcaatgct    780
caatccaaag ttcttgttgc catgttgctg gatttcctgg tgatttgact ccaataaatat    840
gcccaataag tcgtcattac tagtttctcc tgctttcatt gccttcaatc ttttatcaat    900
aatactcctt actgaggccc tcacttcttt gtcaatctcc ttcatcctct tgttcattt     960
ggttggtaaa aatctcattc ccgggaggta tattgactgt gtagccttta ttatgtgttg   1020
agctagctct gtttgaagtt caaatatcct tcttccctct tcatagctac tgccaaatgc   1080
tgtacgcgaa atcacatcac tagacattgt ctgaagatca ggccacacat ccacctcaca   1140
tgtgccgtcc tcccatttac ttatcatctc tctacagctc aaaataaagg ccggcagcat   1200
atgcttgagc ttctcaacgt ggaaagcagg attgataatt tttctgtgtt tgacccattg   1260
atcaccatca tgacttgcta gaccccttcc aagcaacctg gttaatggat ttcctcccct   1320
a                                                                   1321
```

<210> SEQ ID NO 26
<211> LENGTH: 9000
<212> TYPE: DNA
<213> ORGANISM: Artificial Sequence
<220> FEATURE:
<223> OTHER INFORMATION: CL12047.Contig3_All

<400> SEQUENCE: 26

```
tgaatctaaa tactcagaaa ttccctttg acagtactat atgtaaatcc tagatatcaa      60
aatctgtgga atttttgga aaggatctaa aaaaggaaaa aataggatag acataaatta     120
atcggccgaa ataagaagag cctatgagat agacatatat acatactgaa tcctaaaaag   180
agttcagatt cgaattccct agataaaata gatgggattg gctataatac tagtcaaatg   240
aaagattttc tcaagatttt tttcatctac ttaagatttt gcaaatgggt tagttgaacg    300
```

```
tgaaaattca ctcattgaat aagtaaacaa ttgaattgga ttcgagggga tagtagtaat    360
gaaatcgcgt gctaactccc agttctttgt gaattaatca atcaacttgc tatcggacat    420
ttattttgat atttgaattc gacaattttc gcaaaaattt ggatatttt cagtttattt     480 attattatga gactcaatcc tactacttcc ggttctgggg tttccacgct tgaaaaaaac    540
aagccggggc gtatcggcca aatcattggg ccggtcctag atgtagcttt tccgccgggc    600
aagatgccta atatttataa tgctcttgta gttaaaggtc gagatactct tggtcaacca    660
attcatgtga cttgtgaagt acagcaatta ttaggaaaca atcgagttag ggctgtggcc    720
atgagtgcta cagacggtct catgagagga atggaagtga ttgatctggg agctcctcta    780
agtgttccgg tcggtggggc gactctcgga cgaattttca atgtgcttgg cgagcctatt    840
gataatttgg gtcctgtaga tactcgcaca acatctccta ttcatagatc tgcgcccgcc    900
tttatagagt tagatacaaa attatctatt tttgaaaccg gaattaaagt agtcgatctt    960
ttagcccctt atcgccgtgg aggaaaaatc gggctcttcg ggggagctgg ggtggggaag   1020
acagtactta ttatggaatt gattaataat attgccaaag ctcacggggg tgtatctgta   1080
tttggcggag taggtgaacg tactcgtgaa ggaaatgatc tttacatgga aatgaaagaa   1140
tctggagtaa ttaatgaaca aaattttgca gaatcaaaag tagctttagt ttatggtcag   1200
atgaatgaac cgccgggagc tcgtatgaga gttggtttga ctgccctaac tatggcggaa   1260
tatttccgag atgttaataa acaagacgta cttctcttta tcgacaatat cttccgtttt   1320
gtccaagctg gatctgaagt atccgcctta ttgggtcgaa tgccttctgc tgtgggttat   1380
caacctactc ttagtactga aatgggttct ttacaagaaa gaattacttc gactaaaaag   1440
gggtctataa cgtctattca agcagtttat gtccctgcag acgatttgac cgaccctgct   1500
cctgcgacga catttgcaca tttagatgct actaccgtac tatcaagagg attagccgcc   1560
aaagggatat atcccgcagt agatccttta gattcaacgt caactatgct acaaccccgg   1620
atcgttagtg acgaacatta tgaaattgca caaagtgtta agcaaacgtt acaacgttac   1680
aaagaacttc aggacattat aactatcctt ggattggacg aattatccga gaggatcgt    1740 ttaaccgtag caagagcgcg aaaaattgag cgtttcttat cacaacccct ttttgtagca   1800
gaagtattca ccggttctac gggaaaatat gttggtctag tagaaacaat tcgagggttt   1860
caattgattc tttccggaga attagacggt cttcctgaac aggccttta tatggtaggt    1920 aacatcgatg aagctacggc aaaggctatg aacttagaaa tggagagcaa tttgaagaaa   1980
tgaccttaaa tctttgtgta ctgaccccta atcggattat ttgggattcg gaagtaaaag   2040
aaattatttt atctactgat agtggacaaa ttggcgtatt accaaatcac gcccctattg   2100
ccacagctgt agatataggt attttgagaa tacgccttaa cgaccaatgg ttaacgtgg    2160 ctctgatggg cggttttgct agaataggta ataatgagat cactgttta gtaaatgatg    2220 cggagaagag tagtgacatt gatccacaag aagctcagca aactcttgaa atagcgaaag   2280
ctaatttgag aaaagccgaa ggaaagagac aaataattga ggcaaatcta gctctccgac   2340
gggctaggac acgagtagag gctctcaatg agatttcata actagtttct gtgtccccga   2400
ataattaaaa aggttcgatt tataaaaccc cactttggta gttttgttgg atttcgtcga   2460
ttaaatacaa tcaaatctaa tcaagcagaa tcttattttg gtgcaacgga aaaagaagg    2520 ggataaaatc acctgtttga ttgagcaaat tgctaaaaaa tttctacctc ttagtattga   2580
taaaatatac aatattcggg gggtgcaagc gcctaactat tgattcgata agggcttatt   2640
cgaatctact cgtaccgcat aatctttta ctagataagc caaaatcaga caaatggagt    2700
```

```
tttctttgtt gataacatat cctcactttg ctacatactt aaatctatac taagtgagta    2760
tctaatcgat attatttaag aattaataaa aattccaatt tttgattata ataagatatc    2820
tttataaata ataataacag gaacaaatag taaatcgagg tttctatgac acttctaagt    2880
tttccctccg ttttggtgcc tttagtaggc ctagtatttc cggcaatcgc aatggcttct    2940
ttatttcttt atattcaaaa aaataagatt gtttagaacc gatgggacaa agtctcattc    3000
attttatttt tagacttgta cgataacccc aggtatttat ttatggaata tggtataagc    3060
ggcttcggcc gaaaaactct tatggctaca gaaagacgat atatgagtat gtggatatct    3120
ttaatggggt catacgaagg atatgttatt agtttagatc taatcaattt aatgaattac    3180
tcctaaaggt ttacatcaaa cttgtgctag ttgatgagag tgacttcgga aacaaaaaga    3240
ctaaagtcaa attcatttgg ggtattctct caattcgaag aaaatgcaac cgggttaagt    3300
atgagttggc gatcagaaca tatatggata gaaactataa cggggtctcg aaaaacaagt    3360
aatttctgct ggactgttat cctttttta ggttcattag gattttgtt agttggaact       3420 tccagttatc ttggtagaaa ttggctatct ttatttccgt ctcagcaaat cgtttttttt    3480
ccacaaggga ttgtgatgtc tttctatggg attgcgggtc tttttattag ctcctatttg    3540
tggtgcacaa tttcttggaa tgtaggtagt ggttatgatc gattcgatcg aaaagaagga    3600
ctagtgtgta tctttcgttg gggatttccc ggaaaaaatc gtcgtatttt cctccgactc    3660
cttataaaag atattcagtc cctccgaata gaagttaaag agggtattta tgctcgtcgt    3720
gtcctttata tggatatcag agggcaggga gtgcttccat tgacccatac tgatgagaat    3780
ttgactgcgt gggaaattga acaaaaagct gctgaattgg cctatttctt gcgtgttccc    3840
atcgaagttt tttgagaaat gggaaaaatt ttctcagcag gagggaaaa ctcaagaatc     3900 ttctttttct ataacatatt tcgataacaa aacttaactg agatttcgtc cgaacattca    3960
ttcgagctaa agcaggctta tatgggacaa ggataaaaaa acttttttgg ggttggagtc    4020
tgtctttttt atatgtgtgt aataaacaca actcaattca ataaaaacaa gaagtaagaa    4080
attgaaagaa tggattcatc tcataatcaa ccctttggaa ataaaacccc ccctttccta    4140
cttttatttt ttacatattt ttaataagtc caatatttgt ataaataaaa aatatagaaa    4200
tccagactag ttggaattga aactttagat tcagatagat catatcctgt aaattttac     4260 aatcgacacg ccttatttat ctatttttt gctccgtaat gtccaaacag ttggatgcct     4320
taataaggat tacggataac tagccaattt ctgtcttggt ttgcagcttt ttttgatcat    4380
aacaatattt ttccgaaact tccctcaatt attctattcc cgactcctca tagttagcga    4440
acttttttcg aaatattagc tattttgata gaataataaa aagggagttc tttcgtctca    4500
aaatctgaat aagattcata ttcattactt aattctttcg gccattcctc gaagggaact    4560
acttttgacc aattgagttg aaagatcggc aaacaatatt gttgattctt tgttcattcg    4620
aagtcaaagt ggattcttag tcaatttggg tactcttttcg agattcgaga actaagcccg    4680
aaattacaaa tcaaaagag tgcatagatt cctagcttcg ataccgtgga atagaactcg     4740
tacgtaagag aaagatgcga tggcatagaa tcgctgacgg agatattttc agtaacaact    4800
cacagatgaa aaaatggcaa aaaaaaaagc atttacccct cgtttatatt ttgcatttat    4860 agtattttg cctcagtgtc tttctctctt atttaataaa agtctggaat cttgggttac      4920
taattggtgg aatactgggc aatccgaaac ttttttgaat gatattgaag aaaagagtat    4980
tctagaaaaa gtcatagaat tagacgaact tctcctcttg gacgaaatca tcaaggaata    5040
```

```
ctcggagaca catctacaaa accttcgtat aggaatccac accgaaataa tccaattaat    5100
caagatacat aacgaggatc gtatccatat gactttgcac ttatcaacaa atctaatctc    5160
tttcgttatt ctaagtggtt attctatttt gggtaataaa gaacttgtta ttcttaactc    5220
ttgggctcag gaattcctat ataatttaag tgacacaacc aaagctcttt ctattctttt    5280
attagcggat ttttgtctcg gatttcattc gacccgtggt tgggagctaa taattagctc    5340
tgtctacaaa gattttgggt ttgttcataa tgatctaatt atatcttgtc ttgtttctat    5400
tcttccagtc atgctagata gcatttttaa atattgggtt ttctattatt taaaccgcgt    5460
ctctccgtca cttgtagtga tttatcattc aataagtgaa aaatgatcta tcgatcctat    5520
attaatccaa ttagaatgtt tcttactttg tagttgtaca taagcaaagg aattcaaatt    5580
gtacttcttt tttatatttc taccccatcc gggggattta tcctataata ttattccagt    5640
aaatagcaga attgtggata ggaaactaga ttagtgacct actcaattta ttgtagaaat    5700
tttcggtatc actggaccat gcaaactaga aatacttttt cttggataaa ggagcggatt    5760
gctcgctcca tttccgtatc gctcatgata tatatcataa gccagacatc tatttcaagt    5820
gcatatccca ttttttgcaca gcagggttat gaaaatccac gagaagcgac cgggcgtatt    5880
gtatgcgcca attgccattt agctaataag cccgtggaga ttgaggttcc acaagcggta    5940
cttcccgata ctgtatttga ggcagttgtt cgaattcctt atgatatgca agtgaaacaa    6000
gttcttgcta atggtaaaag ggggctttg aatgtcgggg ctgttcttat tttaccggag    6060
gggtttgaat tagcccctcc caatcgtatt tccccagaaa tgaaagaaaa gataggaaat    6120
ctgtcttttc agagctatcg ccctaataaa aaaatattc ttgtcatagg ccctgttcct    6180
ggtcagaaat atagtgaaat caccttttcct attcttccc cagacccgc tactaagaaa    6240
gatattcact tcttaaaata tcctatatat gtaggtggaa acaggggaag aggtcagatt    6300
tatcccgacg ggaacaagag taacaatact gtttataatg ctacagcaac cggtatagta    6360
agcaaaatca cacgaaaaga aaagggggg tccgaaataa ccatagcgga tgcattggat    6420
ggccgtctag tgcttgatat tatccccct gggccagaac ttctcgtttc agaaggagaa    6480
tctatcaaat ttgatcaacc gttgacgagt aaccctaatg tgggcggatt tggtcaagga    6540
gatgcagaaa tagtacttca agatccatta cgtgtccaag gtcttttgct cttcttggca    6600
gctgttattt tagcgcaagt ctttttggtt attaaaaaga aacaattcga gaaggttcaa    6660
ttgtccgaaa tgaatttcta gactcgcgga tttatcgacg ttcgtaaaaa gaaccaaact    6720
ctttttatag attatctatc tatttctata agatgacagt aattccttgt accacatttc    6780
tagttatagt atctagattg tgaagaaaac tgtttgactt gaccccccctt tcttttgtttt    6840
tttctaaatt ggggtggtgt gactatattc ctatttgtca gattaaaatg tcataaaatg    6900
catcaatatc aatattttt taattcaatt cggctagata ctagacataa gtaacataag    6960
taagcggtaa atggaagaga aaatgagggg aataaataat tctagtaggg attcttcgtc    7020
ttcccagtct tcgacacaag aaaagaaatt ttccacaccc cctttcttgt gtcgaaataa    7080
taatgattct tgattctgtt cgtcaaagat tcccagtctt agtttccatt ttagcaaggt    7140
gtattagaac ttgtttttag attctctcctt attccgtctc tacttattcg ataatattct    7200
aaaatctata aatatctaat aatataagtg gtggacaaag acaaaaagag gggtcaattg    7260
atgagagact aaaataacta gaataaaggt ttattcatat agaaagaatt tgatgaaata    7320
taatataccct atatatataa tatctagaaa gttatcgccg gaatcgagtg attccgtctt    7380
tagtctaact ttcttttttga ttcttttattt gttattctaa cttgacttaa agtattgaga    7440
```

-continued

```
gatactatcg agcaagaggt gttcgaaatc aatttatttt tcaaaaccat catcagaaaa    7500
aatagaatgg agcccaacag cttttgtcat ttcgacgaac aaactcttcg aacgcgtaag    7560
aacgcaacgg cattcccttc tttgtttgtc tggtttgagg cccgttgagt tcttacgctt    7620
tcatgtcgac aactcaattc atacaattac tacaggatg aacccaatcc ggaatatgaa     7680
ccataaaaga aaatacctat taaaccgatc acaagaatac ccgttacagt acctattatc    7740
caaagaggaa tccttccagt agtatcggcc atttacccca cttcctcca aatttgatca     7800 agtggtcatg ctagagacag aaacagtcat ggataatgat gagatgagat ccttccgagt    7860
gggctaagag agaataccc tagccagatt cttctatagt tttcttaatt gaagaaataa     7920
ttggaaaata aaacagcaag tacaaaaatg agtaataacc cccagtagag gctggtacga    7980
ttcaattcaa cattttgttc gttcgggttt gattgtgtca tagctctata attcggatta    8040
gttttatcgt tggatgaact gcattgctga tattgacccc aaaaaaaaaa cggtaggtac    8100
agctaggcca tgaacagcca accatcgcac tgtaaaaatt ggataggttc gatctatggt    8160
cattggggcc tcctaaaaag atctactaaa ttgatcaagt tgttccaaag aatcaaaacg    8220
gccggtgatt actggaattc cttgtcggtt ttctgtgaaa tactcgtttg ccgagggct    8280 tccaaacaca tcgtaagcta aaccagtgct gacgaataac caacccgcaa tgaataggga   8340
aggtatagta atgctatgaa tgacccagta gcgaatactg gtgataatat cagcaaaaga   8400
acgttctcct gtgcttccag acatgccgag ctccacatat tcttgtacag tcaaaaggta   8460
tcgattccgt aaaagatcag atcagtaaat gaacatttac caaaatgcaa tctttgtgag   8520
atcgtccata ttgtaccgag ggcgtcttta gggtctaccg aatcagtata gcgatccttc   8580
ttctgacaca gcaaggcatt ttgaatccgt attggaagga attgctaaaa aatttccttc   8640
ttcctttcct tgttgtttgg cgatgtaaaa taataccca ttcaatagaa aattcctcaa    8700
aatagtctag ttcgctccaa tatggctttg tggggagaaa gggaagatat gataaaatgt   8760
gaatctgata agttgttttc taataatgca tgaaagaggt tatgatcttc ccccaattta   8820
agtggatgcg agatctataa atcttctttt tcgtagttgt agggcggttt ttattggaat   8880
ctttttttca tttgaagaaa ttagttattc gtccagtaac aagtaagagt attaaattgt   8940
attcgctaaa agaaagaaac caaagaatta cctaattgga atcactaatg gtgatacgcg   9000
```

<210> SEQ ID NO 27
<211> LENGTH: 1231
<212> TYPE: DNA
<213> ORGANISM: Artificial Sequence
<220> FEATURE:
<223> OTHER INFORMATION: CL1361.Contig15_All

<400> SEQUENCE: 27

```
ggaggcctca cgatcaatct acattccagg atctagattt ttgccaacta aaaggaacaa     60
gaggatgaag gagattgcca aggttgtgag ggcttcaata aagagtatta ttgataaaag    120
attgaaggca atgaaagctg gagaaactag taatgatgac ttattgggca tattattaga    180
gtcaaattac aaggaaatcc aacaacatgg aaacaagaac tttggaatga gcatcgacga    240
agtcattgag gagtgcaaac ttttctactt tgcaggacag gagactacct cgaatctatt    300
ggtctggtca atgatcttac tgagccagca tcaagtttgg caagctcaag caagagaaga    360
agttcttcaa gtgtttggta ataaacaagc agatcatgac gggttaaacc acctgaaaat    420
tgtaaatatg atttttgaacg aggttctgag gttataccca ccagcagtat cacttgggcg    480
```

```
gatgatttat gaagaaatga agctaggaga ttttactctt ccagaaggag tgataatcca    540
agtgcctata atggtgctgc actatgaccg tgaattatgg ggtgatgatg caaaagaatt    600
caaaccagag agattttcgg aaggagtgtc taaggctaca aaggggcaag cctcatatct    660
cccgtttgga gggggaccta ggatatgcat tggccaaaac tttgctatgt tggaagctaa    720
aatggccgtg gctatgatcc tacaacagtt ctcctttgca ctctcgacat cctattcaca    780
tgctccccac actgtcatca ctcttcaacc ccagtatggc gctcacttaa ttttgcagaa    840
actttagtcg ttctggaatt tggaataatg ttgtacacat aataatgggg tcacgtttca    900
aggtgacgaa ctgttgtagg gatgtatata tttcttgaat gtcataagga tactccctct    960
gtctagagct gaggctcttt ccacagcctt ccctgctttt caacaccagc atatctacgt   1020
ttagtcaagt gtggccttat gagttaattt caagtcttcc tcctcccctt ttctgccgtt   1080
tgacgactgc attagtttat atctgttggt gggtggttcg tcaatcttga tacattaccc   1140
aagctaattt atgtagaaat tgtgggcaag ggatttccac catagtgatg cacaatcctt   1200
ttctgagaaa ggaattcttc tcatactaag c                                  1231

<210> SEQ ID NO 28
<211> LENGTH: 1809
<212> TYPE: DNA
<213> ORGANISM: Artificial Sequence
<220> FEATURE:
<223> OTHER INFORMATION: CL2976.Contig3_All

<400> SEQUENCE: 28
atgaccgagc atattcaag ccaaactcaa gccatttaca gcccctagct agcacttgca     60
cagttgcact atatctgcag gatcttatga tgtacagtct cactaaaggt tacaaagata    120
gataatccac agattcaact tgcattgaaa catcttact atctatttgt ctctaaatga    180
gtttcatttt cgataaaagt tatgatcttt gcgcaatatg aatcgatcta gcttacaacg    240
acaaaacata actgaaagtg gtaatactat atagaggatc caattatata caacagtctg    300
atttatgagt tgttacccca tctattgcgg ccagacgaga tcaccattga aacacttacg    360
ttttcaaaag cacaaatatg tatcacgaac ttatgctaag agttggagct gctggctgcc    420
attgacgaac tcctcacagc aaccttgaca gcaccaacca cactaagctg ccttatatca    480
ggccttaaca tcgtctgttt atcctggctc acataacttg cttctaactg aacctcgaca    540
aagtatgcaa tcttgcctga agcattccga acaggtgaga tgtgaagaaa gttctgaaat    600
ggactctcat cttttctgta atttaagatg catacggtaa atgcttgtcc agtttgcatg    660
ctatccctta tctgggactg agttgataaa tctgtgtcct gcccacttaa aaatctacaa    720
tttcgcccca aaacttcatg tctagcataa cctgtcaatt ccaggaaggc gtcacttgca    780
taaacaatag gcatgtcggg taagtacgga tccgttaata caaagctttg tttgattcta    840
ccaagagata tgtttaaaga tgcaccaagc gggctcatgc cacagcatct ctttccacaa    900
accagtctgc cagttaactc gctatagtgg gtcagcacag acattatgtt gttcatggca    960
gtgatagctc tccgcttctc tatgtcacta gccttgcaag tctcttcagt tattcctcta   1020
tcatcagcca aaaagaatc ctgagctgaa actcgagcca attctgcaac tgtatcagag   1080
cacacctccc tcctacagga accaagcaaa gtctcgcgaa acatgaccc atcatcattc    1140 aaattcaccc cattcctcac aaacccacag ccagaccgcc tcggttttcg tgtaataggc   1200
acttgaactc caacaaaatt aatcaccctc ccatccttct tactaaaaac agggcacata   1260
tgaaacaaca tcgaaaggg agtcccatcc tttctataat tcaatatact aatttgaata   1320
```

```
ttcctttctt ctctaacagc ctccctaatt tccataactg atctcctatt agtcttgatt    1380
ccttgaaata tcctcccatt ctttccaatc acctcgtctc ttgaatacccc tgacattttc   1440 aagaattccc tcgaagcaaa gacaattggg tgaccagaaa tgcaaggatc agttatagtg    1500
aagctatcag gcaattcatc gagcgcttcg cgtacccaaa cagaatactg ttcattaaat    1560
aactgttcga tacaatccat ttgtggttcc atagtaagtg tagtgtaact tcaattcttg    1620
aaatactaca gcttcgcaaa tggaaactaa tcccaatccc atgtggttaa gtggaagaat    1680
tgttgctatc aatcaatcgc tgatggaaca ggaatcgtga agtgaccaaa gaaatcttaa    1740
tcagtagaga gagagagaga gagagagaga gagagctggg ggagctgaga actgagcagc    1800
atcacaaat                                                            1809
```